US012233130B2

(12) United States Patent
Beaudoin

(10) Patent No.: US 12,233,130 B2
(45) Date of Patent: Feb. 25, 2025

(54) COVALENTLY-MODIFIED STEROID ACID-PEPTIDES HAVING ENHANCED STABILITY AND/OR BIOLOGICAL ACTIVITY

(71) Applicant: DEFENCE THERAPEUTICS INC., Vancouver (CA)

(72) Inventor: Simon Beaudoin, Sherbrooke (CA)

(73) Assignee: DEFENCE THERAPEUTICS INC., Vancouver (CA)

( * ) Notice: Subject to any disclaimer, the term of this patent is extended or adjusted under 35 U.S.C. 154(b) by 0 days.

(21) Appl. No.: 18/318,384

(22) Filed: May 16, 2023

(65) Prior Publication Data

US 2024/0207426 A1 Jun. 27, 2024

Related U.S. Application Data

(60) Provisional application No. 63/476,739, filed on Dec. 22, 2022.

(51) Int. Cl.
*A61K 47/68* (2017.01)
*A61K 47/64* (2017.01)

(52) U.S. Cl.
CPC ...... *A61K 47/68033* (2023.08); *A61K 47/645* (2017.08); *A61K 47/6803* (2017.08); *A61K 47/6849* (2017.08); *C12N 2710/10322* (2013.01); *C12N 2710/10333* (2013.01); *C12N 2710/10371* (2013.01)

(58) Field of Classification Search
CPC ... A61K 47/64; A61K 47/6803; A61K 47/554
See application file for complete search history.

(56) References Cited

U.S. PATENT DOCUMENTS

| 5,955,365 | A | 9/1999 | Szoka, Jr. et al. | |
|---|---|---|---|---|
| 7,732,177 | B2 | 6/2010 | Iadonato et al. | |
| 11,291,717 | B1 | 4/2022 | Beaudoin | |
| 2003/0069414 | A1* | 4/2003 | Kirschenheuter | C07H 19/06 536/27.22 |
| 2022/0218820 | A1 | 7/2022 | Beaudoin | |

FOREIGN PATENT DOCUMENTS

| CN | 100588425 | | 2/2010 |
|---|---|---|---|
| EP | 1 046 394 | A2 | 10/2000 |
| EP | 2154145 | B1 | 4/2013 |
| WO | 2017/156630 | A1 | 9/2017 |
| WO | 2018/165752 | A1 | 9/2018 |
| WO | 2020/252298 | A1 | 12/2020 |
| WO | 2022/126239 | A1 | 6/2022 |
| WO | 2022/232945 | A1 | 11/2022 |

OTHER PUBLICATIONS

Lee et al, Cell, 2006, vol. 126, pp. 543-558 (Year: 2006).*
Chen et al, BioTechniques, 2010, vol. 49, pp. 513-518 (Year: 2010).*
McCombs and Owen, The AAPS Journal, 2015, 13 pages (Year: 2015).*
El-Kadiry et al, Molecules, Jun. 13, 2022, vol. 27, 13 pages (Year: 2022).*
Al-Hilal et al., "Functional transformations of bile acid transporters induced by high-affinity macromolecules," Scientific Reports 4:4163, 9 pages (2014).
Anding et al., "Cleaning House: Selective Autophagy of Organelles", Devopmental Cell, 41(1):10-22, (2017).
Anguille et al., "Clinical use of dendritic cells for cancer therapy", Lancet Oncology, 15(7):e257-67, (2014).
Azuar et al., "Cholic Acid-based Delivery System for Vaccine Candidates against Group A *Streptococcus*", ACS Medicinal Chemistry Letters, 10: 1253-1529, (2019).
Beaudoin et al., "ChAcNLS, a novel modification to antibody-conjugates permitting target cellspecific endosomal escape, localization to the nucleus and enhanced total intracellular accumulation," Molecular Pharmaceutics, 13(6): 1915-26, (2016).
Beaudoin et al., "Antibodies with integrated endosome escape and multi directional intracellular trafficking control capabilities for molecular transport and accumulation of a BODIPY based dye", J Nucl Med, vol. 57 No. supplement 2 1215, (2016).
Beaudoin et al., "Initial Evaluation of Antibody-conjugates Modified with Viral-derived Peptides for Increasing Cellular Accumulation and Improving Tumor Targeting", Journal of Visualized Experiments, 133: 55440. doi: 10.3791/55440, (2018).
Beck et al., "Strategies and challenges for the next generation of antibody-drug conjugates", Nature Reviews Drug Discovery, 16: 315-337, (2017).
Chang et al. "Bile acids are essential for porcine enteric calicivirus replication in association with down-regulation of signal transducer and activator of transcription 1", PNAS, vol. 101, No. 23, (2004).
Chugh et al. "Cell-Penetrating Peptides: Nanocarrier for Macro molecule Delivery in Living Cells", IUBMB Life, 62 (3): 183-193, (2010).
De Loos, M. et al. "Design and Application of Self-Assembled Low Molecular Weight Hydrogels", Eur. J. Org. Chem., 3615-3631, (2005).
El-Kadiry et al., "Accum™ Technology: A Novel Conjugable Primer for Onco-Immunotherapy", Molecules, 27(12): 3807, doi: 10.3390/molecules27123807, (2022).
Hanafi et al., "Overview of Bile Acids Signaling and Perspective on the Signal of Ursodeoxycholic Acid, the Most Hydrophilic Bile Acid, in the Heart", Biomolecules, 8(4): 159, (2018).
Kenney and Meng, "Identification and Fine Mapping of Nuclear and Nucleolar Localization Signals within the Human Ribosomal Protein S17", PLoS One Apr. 8, 2015;10(4):e0124396, (2015).

(Continued)

*Primary Examiner* — Karen A. Canella
(74) *Attorney, Agent, or Firm* — F. Brent Nix, Esq.; Johnson, Marcou, Isaacs & Nix, LLC

(57) ABSTRACT

Steroid acid-peptide conjugates covalently modified for improved stability and/or biological activity are described herein. Covalent modifications include the formation of multimeric compounds comprising at least two steroid acid-peptide monomers covalently bound to one another that behave as new chemical entities, as well as protecting one or more free thiol groups present in the steroid acid-peptide conjugates to improve their stability and/or biological activity.

19 Claims, 39 Drawing Sheets

Specification includes a Sequence Listing.

(56) References Cited

OTHER PUBLICATIONS

Kim et al. "Homodimeric SV40 Nls peptide formed by disulfide bond as enhancer for gene delivery", Bioorganic & Medicinal chemistry letters, vol. 22, pp. 5415-5418, (2012).
Kim et al. "The molecular mechanism for nuclear transport and its application", Anat Cell Biol; 50: 77-85, (2017).
Kosugi et al. "Six Classes of Nuclear Localization Signals Specific to Different Binding Grooves of Importin", J. Biol. Chem. 2009, 284: 478-485, (2009).
Lacasse, V. et al., "A Novel Proteomic Method Reveals NLS Tagging of T-DM1 Contravenes Classical Nuclear Transport in a Model of HER2-Positive Breast Cancer", Molecular Therapy: Methods & Clinical Development vol. 19, 99-119, (2020).
Lam and Dean, "Progress and prospects: nuclear import of nonviral vectors", Gene Therapy, 2010, 17, 439-447, (2010).
Leyton er al., "Auger Electron Radioimmunotherapeutic Agent Specific for the CD123+/CD131-Phenotype of the Leukemia Stem Cell Population." The Journal of Nuclear Medicine, vol. 52, No. 9, 1465-1473, (2011).
Linke, T. et al. "Stimulation of Acid Sphingomyelinase Activity by Lysosomal Lipids and Sphingolipid Activator Proteins", Biol. Chem., vol. 382, pp. 283-290, (2001).
Liu et al., "The Renpenning syndrome-associated protein PQBP1 facilitates the nuclear import of splicing factor TXNL4A through the karyopherin 2 receptor", Journal of Biological Chemistry, 295(13): 4093-4100, (2020).
Lu, J. et al., "Types of nuclear localization signals and mechanisms of protein import into the nucleus", Cell Commun Signal 19:60, (2021).
Manoharan et al. "Cholic Acid—Oligonucleotide Conjugates for Antisense Applications", Bioorganic and Medicinal Chemistry Letter, vol. 4, No. 8, 1053-1060, (1994).
Murakami et al., "Bile acids and ceramide overcome the entry restriction for GII.3 human norovirus replication in human intestinal enteroids", Proceedings of the National Academy of Sciences USA. 117(3):1700-1710, (2020).
Ogris et al., "Melittin enables efficient vesicular escape and enhanced nuclear access of nonviral gene delivery vectors", Journal of Biological Chemistry, 276(50): 47550-5, (2001).
Paquette et al., "NLS-Cholic Acid Conjugation to IL-512a-Specific Antibody Improves Cellular Accumulation and In Vivo Tumor-Targeting Properties in a Bladder Cancer Model", Bioconjugate Chemistry. 29: 1352-1363, (2018).
Paquette et al., "ChAcNLSA14, a novel antibody conjugate PET tracer for targeting human IL 5Rα-positive muscle invasive bladder cancer", J Nucl Med, vol. 57 No. supplement 2 52, (2016).
Patel et al., "Next generation approaches for tumor vaccination", Chinese Clinical Oncology. 6(2):19, (2017).
Raouane et al. "Lipid Conjugated Oligonucleotides: A Useful Strategy for Delivery", Bioconjugate Chemisrty, vol. 23, pp. 1091-1104, (2012).
Ray et al. "Quantitative tracking of protein trafficking to the nucleus using cytosolic protein delivery by nanoparticle-stabilized nanocapsules" Bioconjug Chem. Jun. 17, 2015; 26 (6): 1004-1007. doi : 10.1021/acs.bioconjchem.5b00141, (2015).
Sangeetha, N. M. et al., "Properties of Hydrogels Derived from Cationic Analogues of Bile Acid: Remarkably Distinct Flowing Characteristics", J. Phys. Chem. B, 108, 16056-16063, (2004).
Shivanna et al., "The crucial role of bile acids in the entry of porcine enteric calicivirus", Virology 456-457, 268-278, (2014).
Shivanna et al., "Ceramide formation mediated by acid sphingomyelinase facilitates endosomal escape of caliciviruses", Virology, 483, 218-228, (2015).
Smith et al., "Alternative tumour-specific antigens", Nature Review Cancer. 19(8): 465-4, (2019).
Sun et al., "Factors influencing the nuclear targeting ability of nuclear localization signals", Journal of Drug Targeting, 24(10): 927-933, (2016).
Swaan et al., "Enhanced Transepithelial Transport of Peptides by Conjugation to Cholic Acid", 8:520-525, (1997).
Tagliamonte et al., "Antigen-specific vaccines for cancer treatment", Human Vaccines & Immunotherapeutics, 10(11): 3332-3346, (2014).
Tomatsidou, "Evaluation of peptide-mediated nucleic acid delivery", Department of Pharmaceutics, Utrecht Institute of Pharmaceutical Sciences (UIPS), Utrecht University, 2013, pp. 1-33, (2013).
Wang et al., "HMGB1 in inflammation and cancer", Journal of Hematology & Oncology, 13:116, (2020).
Pavlovic, N. et al. (2018) "Bile Acids and Their Derivatives as Potential Modifiers of Drug Release and Pharmacokinetic Profiles" Frontiers in Pharmacology, Nov. 2018, vol. 9, Article 1283, 23 pages.
Raucher, D. et al. (2015) "Cell-penetrating peptides: strategies for anticancer treatment", Trends Mol Med. Sep. 2015;21(9):560-7.
Li et al., "Design, Synthesis and Antitumor Activity of Dimeric Bile Acid-Amino Acid Conjugates", Letters in Organic Chemistry. Sep. 1, 2007 (Sep. 1, 2007), vol. 4, No. 6, pp. 414-418.
Martinez, et al., "Different Bile Acids Exhibit Distinct Biological Effects: The Tumor Promoter Deoxycholic Acid Induces Apoptosis and the Chemopreventive Agent Ursodeoxycholic Acid Inhibits Cell Proliferation", Nutrition and Cancer, 31(2), 111-118, 1998.
Saini et al., "Targeting Vancomycin-Resistant Enterocoeci (VRE) Infections and Van Operon-Mediated Drag Resistance Using Dimeric Cholic-Acid Peptide Conjugates", Journal of Medicinal Chemistry. Nov. 4, 2022 (Nov. 4, 2022), vol. 65, No. 22, pp. 15312-15326.

* cited by examiner

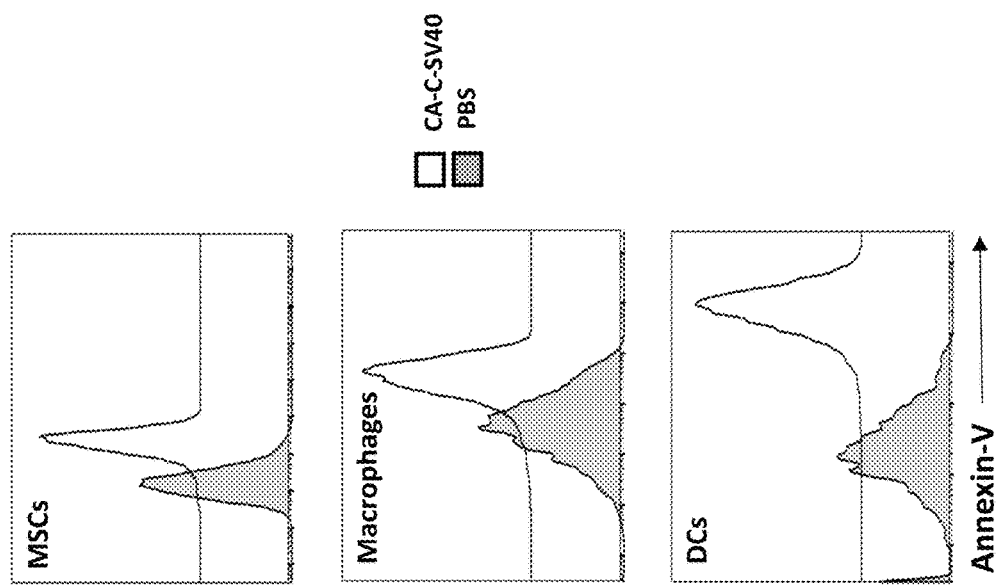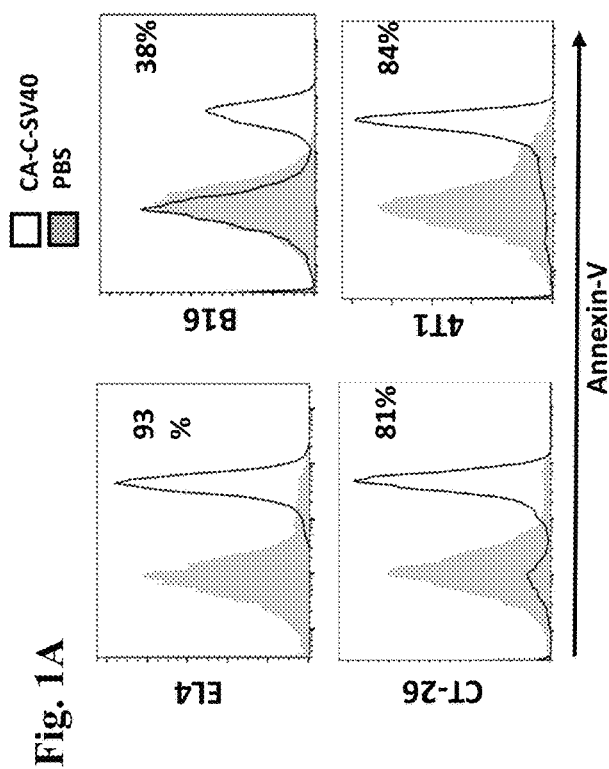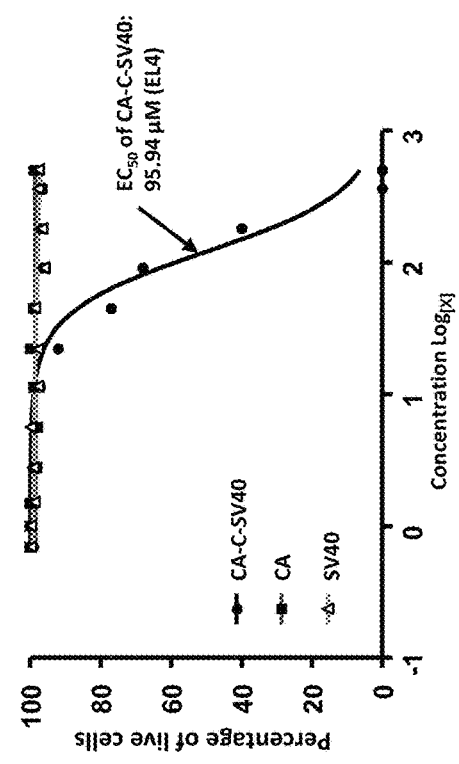
Fig. 1A
Fig. 1B
Fig. 1C

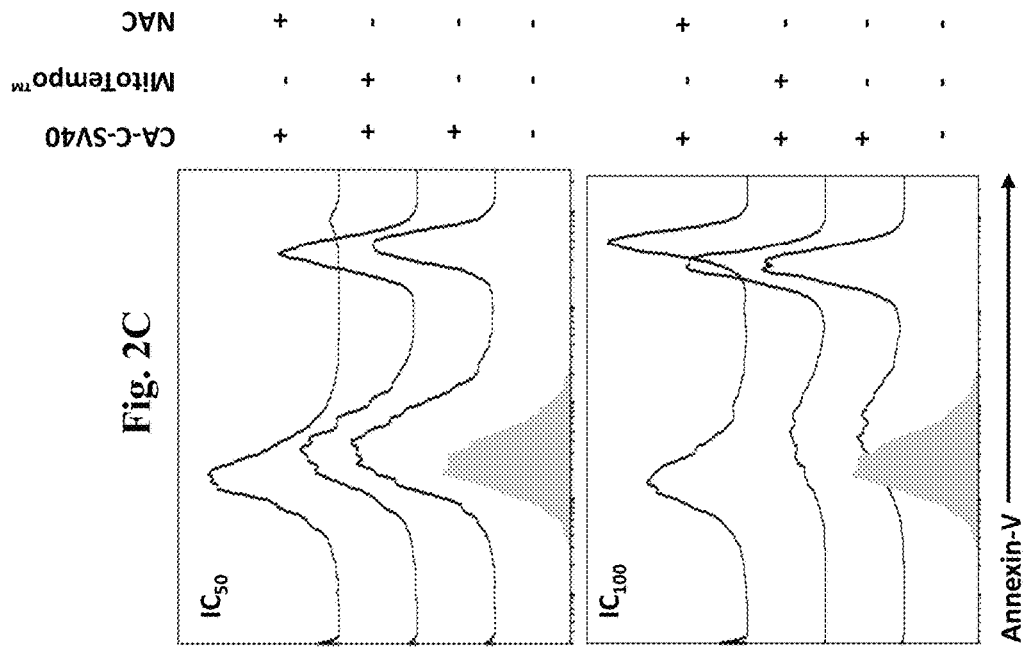
Fig. 2C
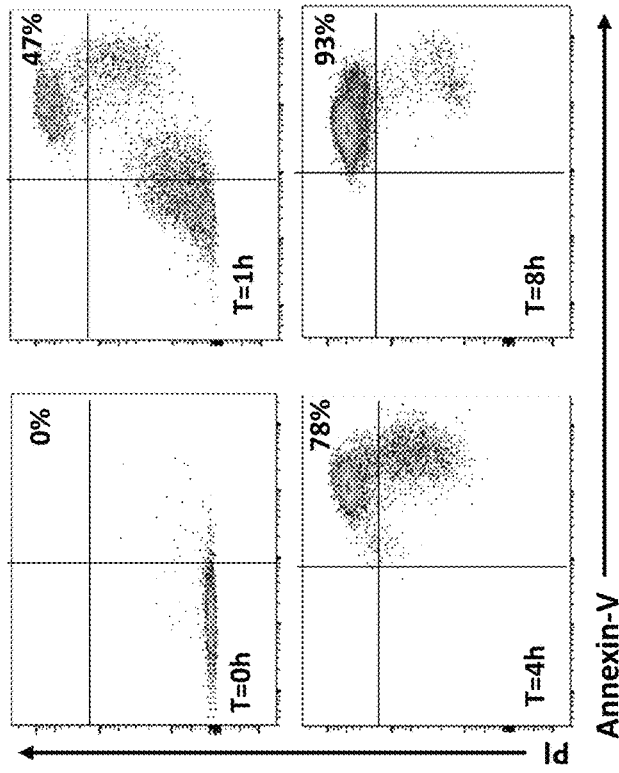
Fig. 2A
Fig. 2B

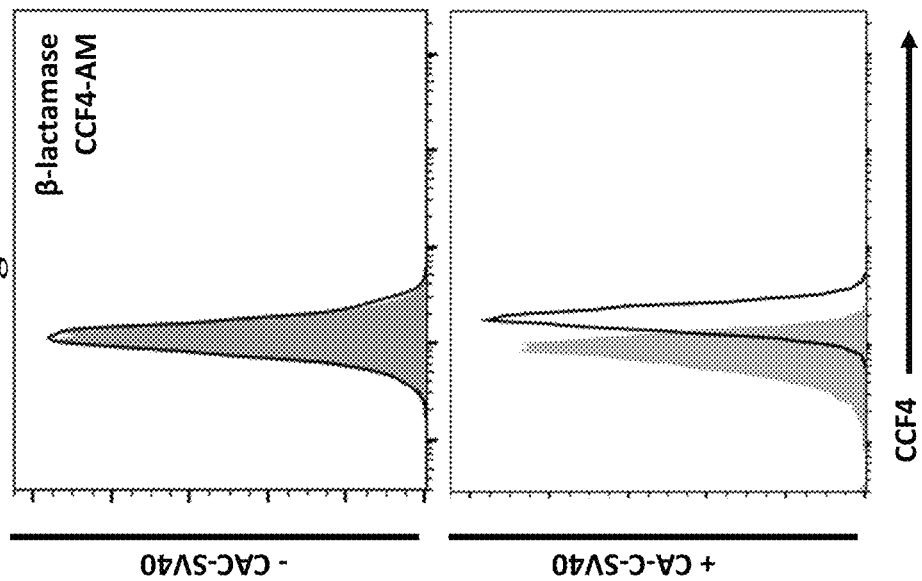
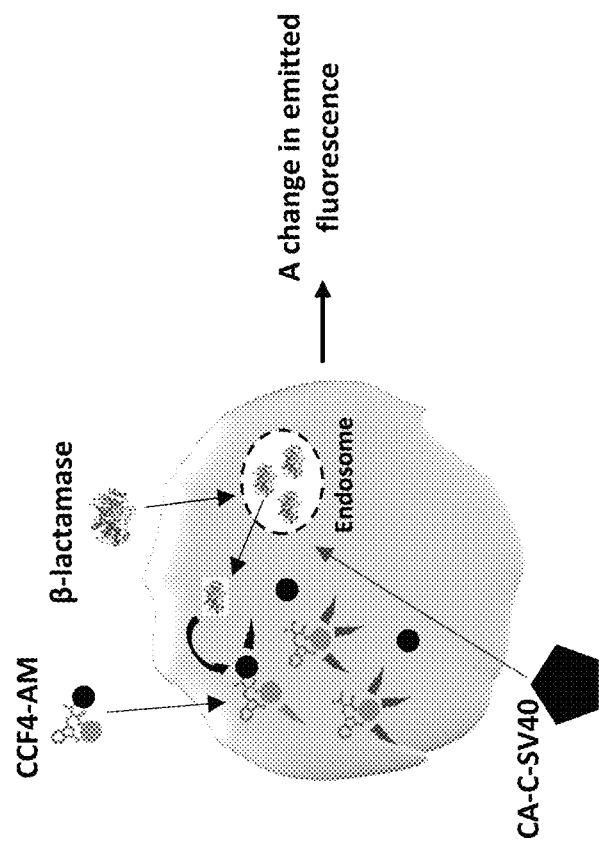

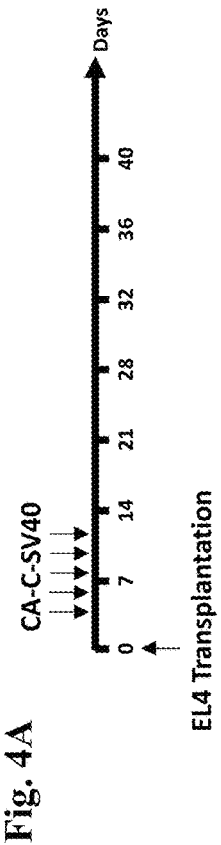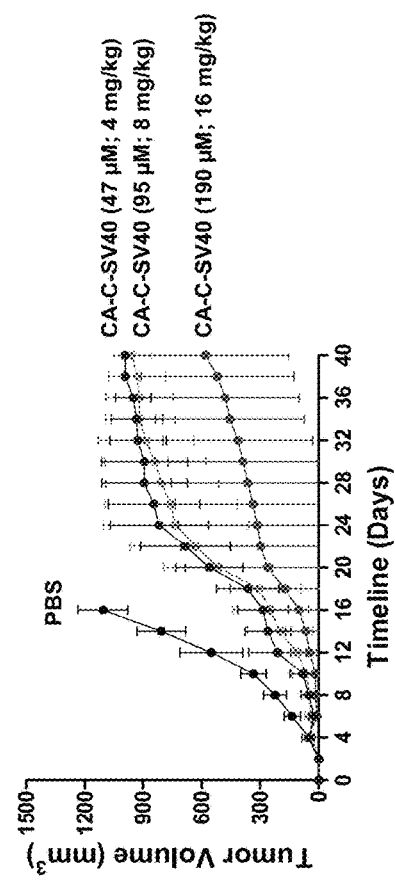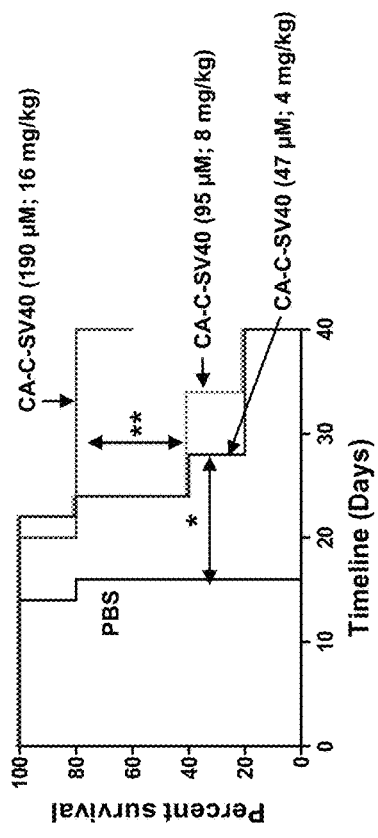
Fig. 4A
Fig. 4B
Fig. 4C

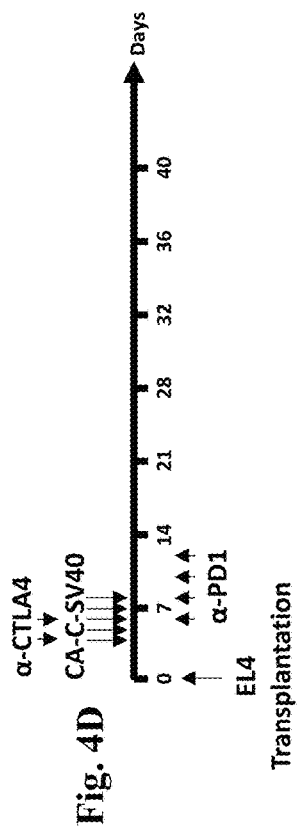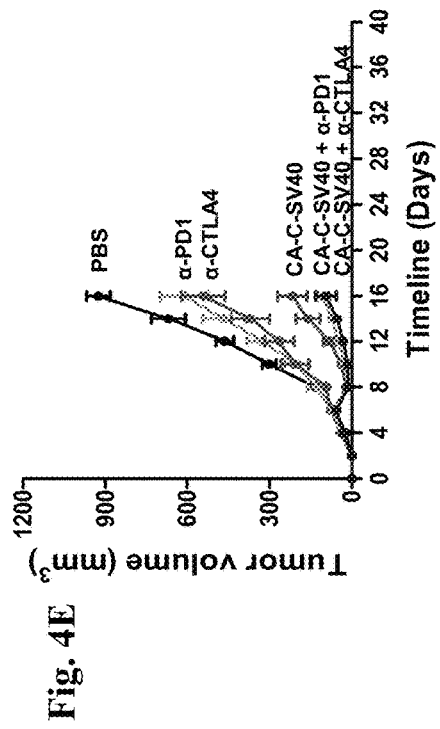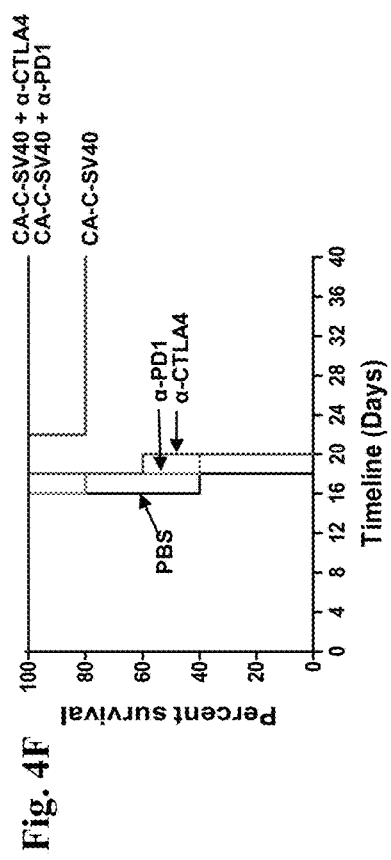

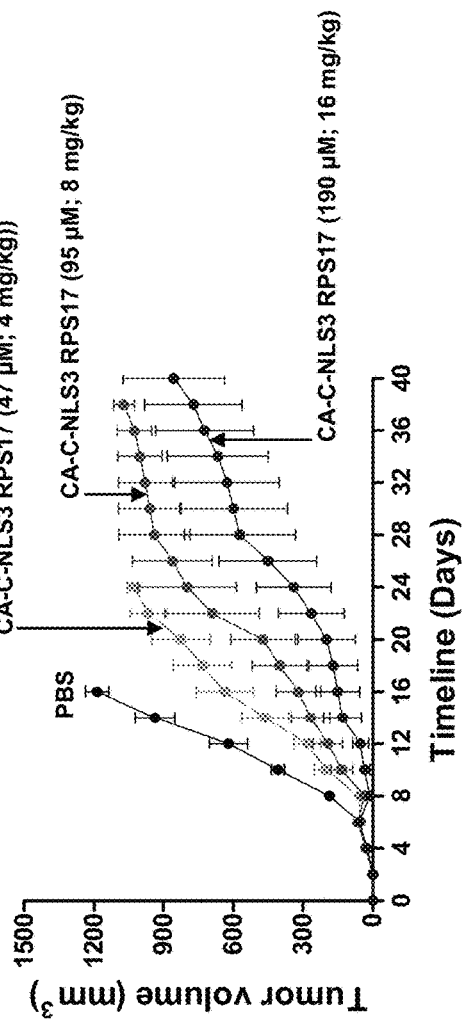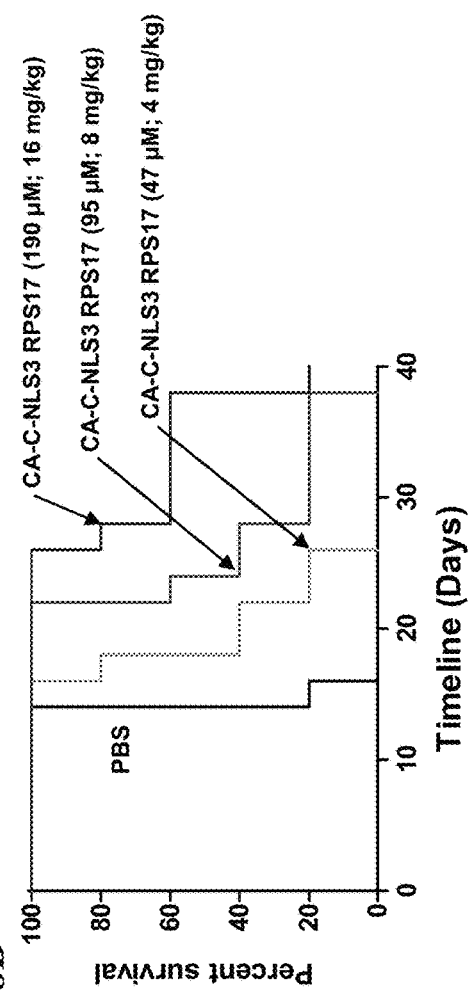
Fig. 8A
Fig. 8B

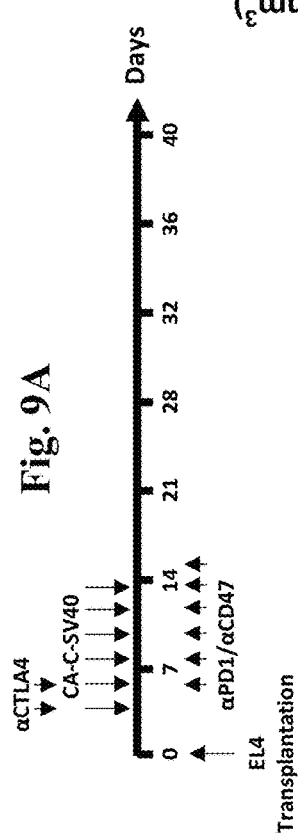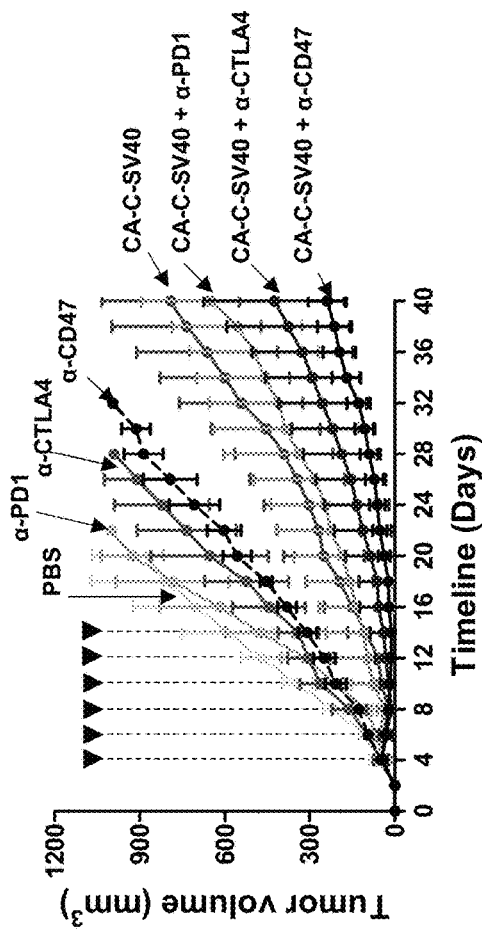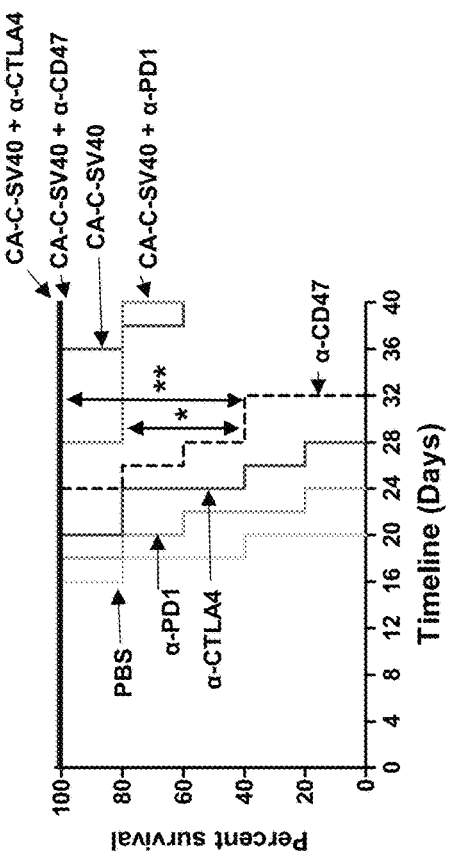

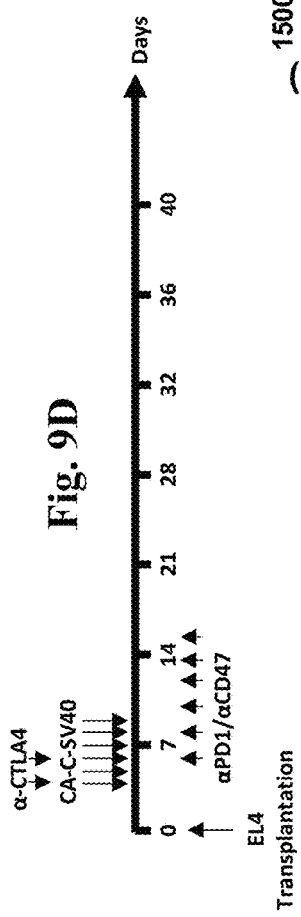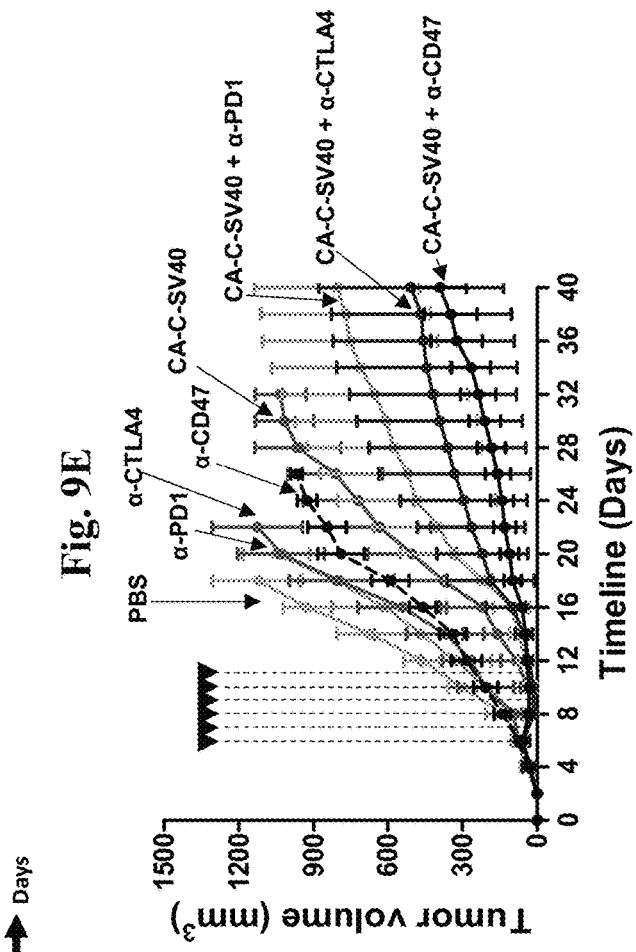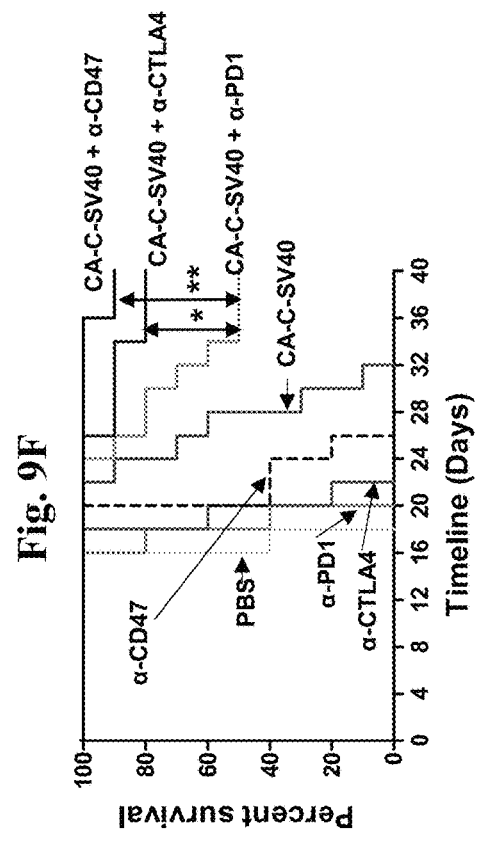
Fig. 9D
Fig. 9E
Fig. 9F

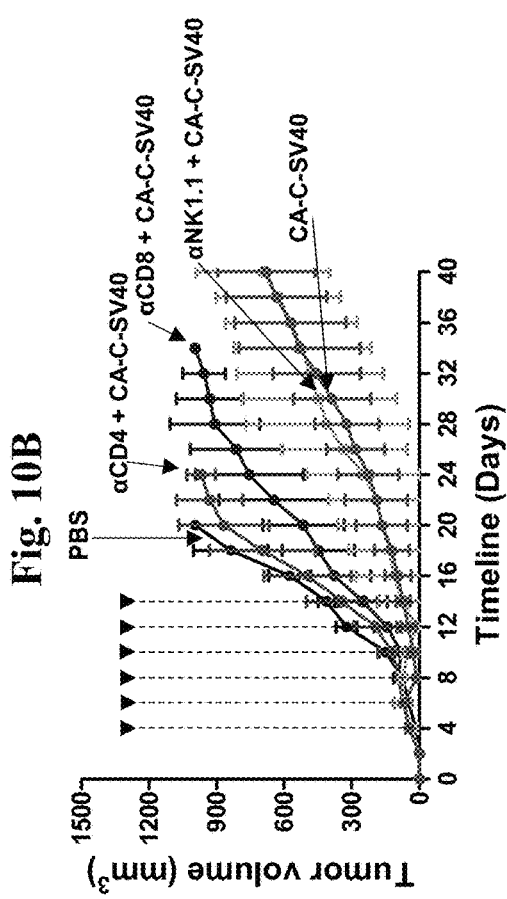
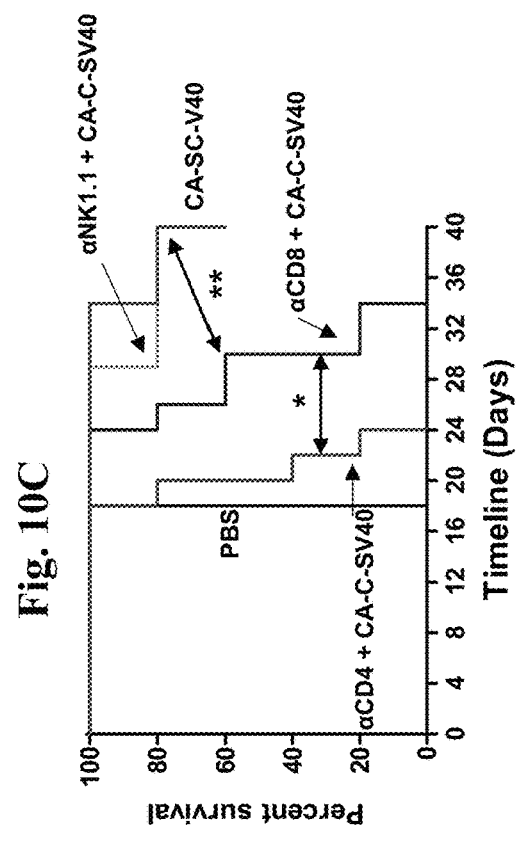
Fig. 10A
Fig. 10B
Fig. 10C

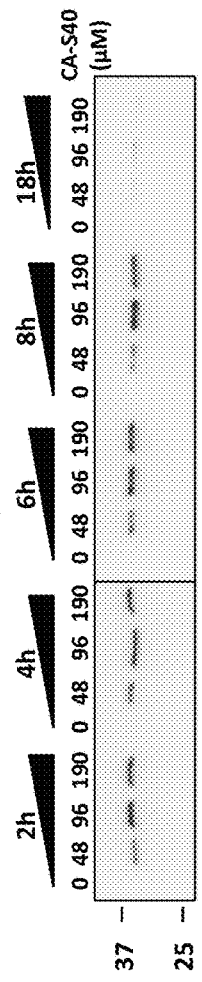
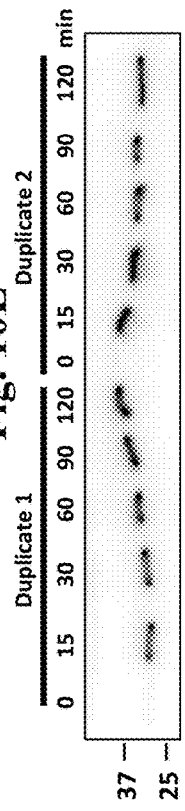
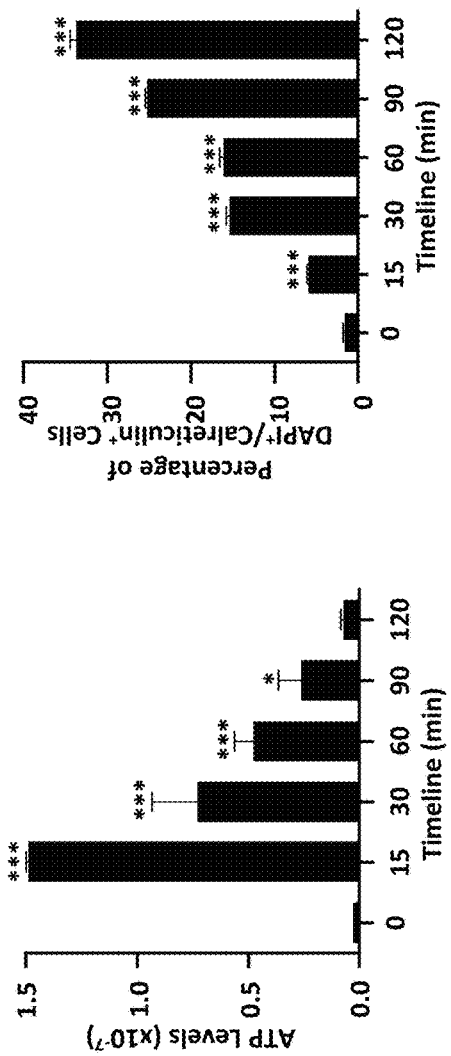
Fig. 10D
Fig. 10E
Fig. 10F
Fig. 10G

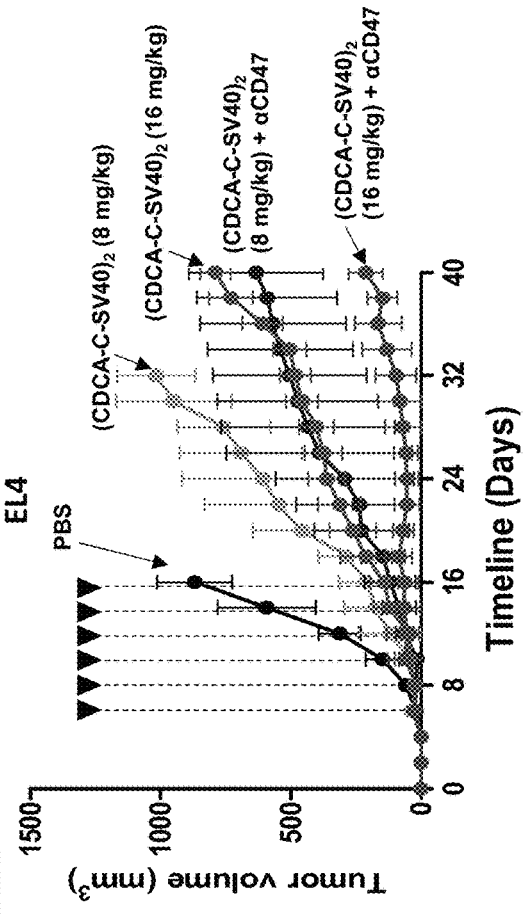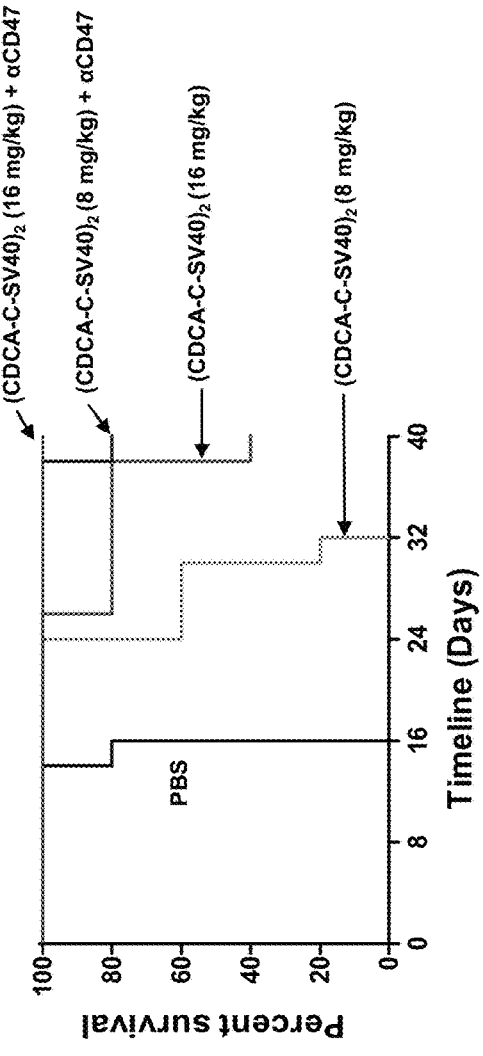
Fig. 12A
Fig. 12B

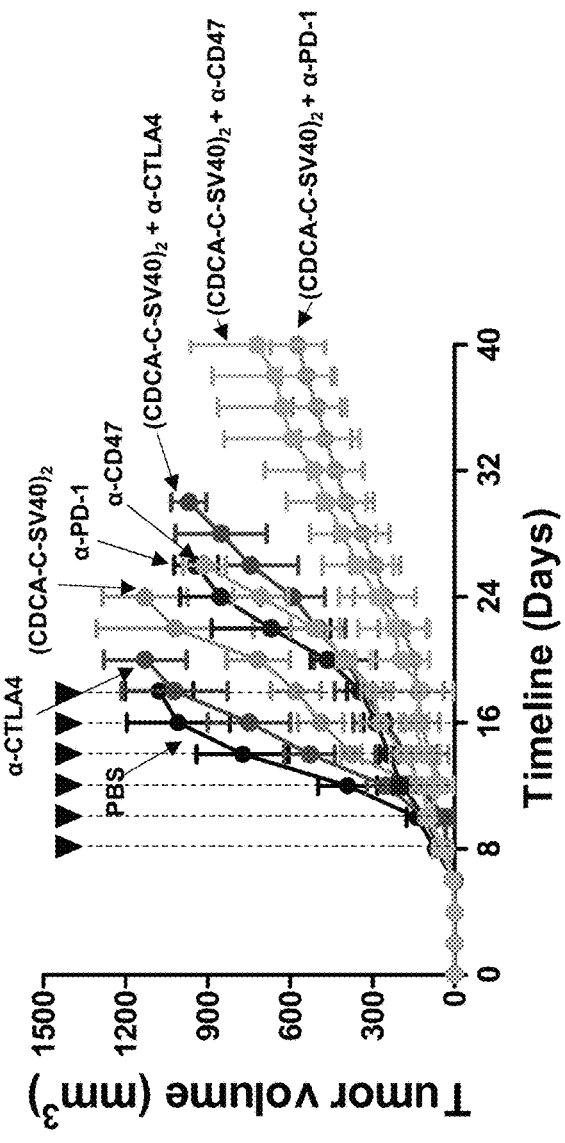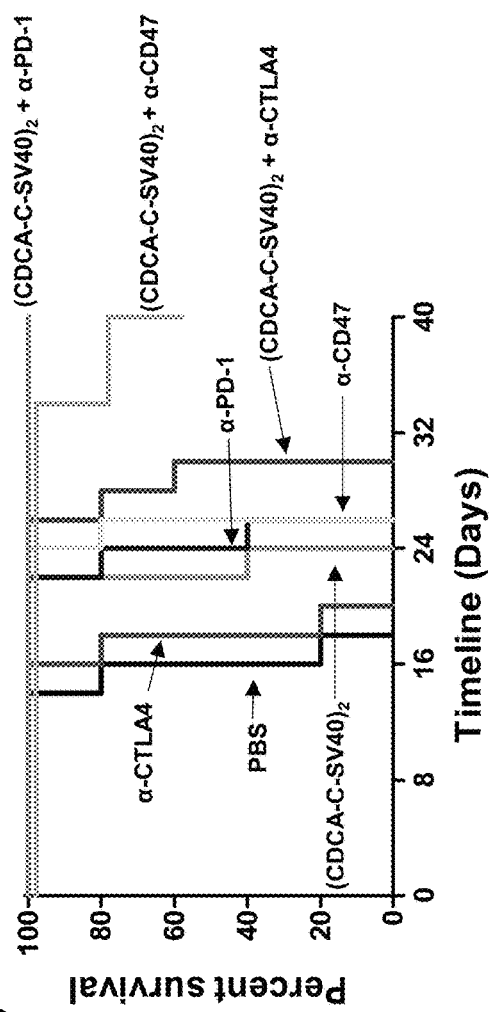
Fig. 12C
Fig. 12D

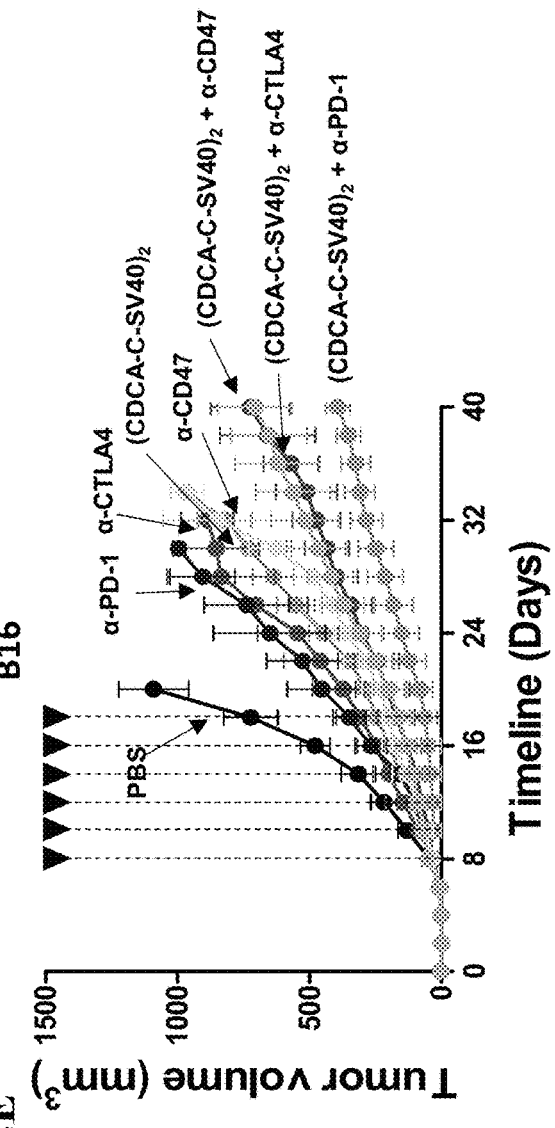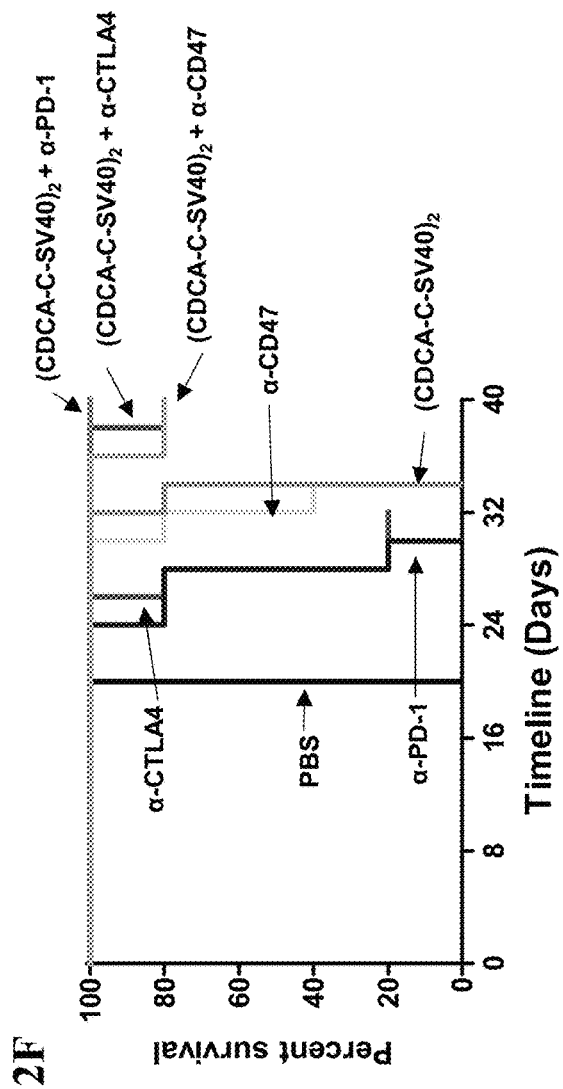
Fig. 12E
Fig. 12F

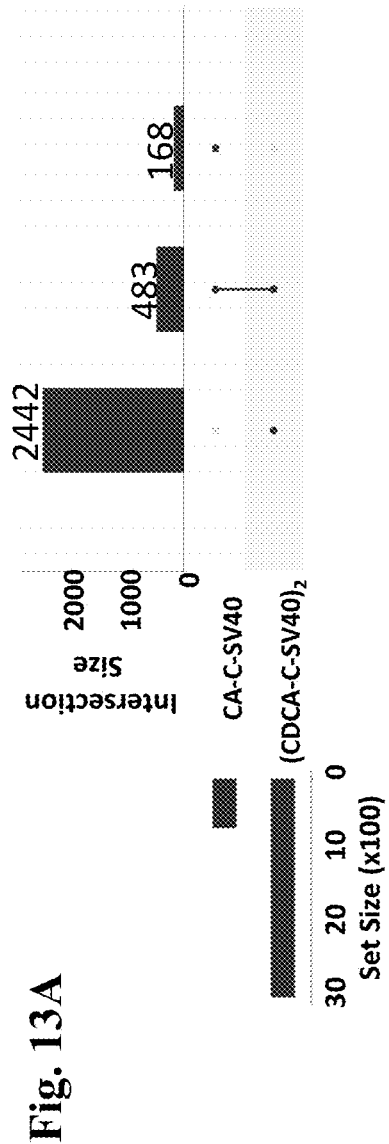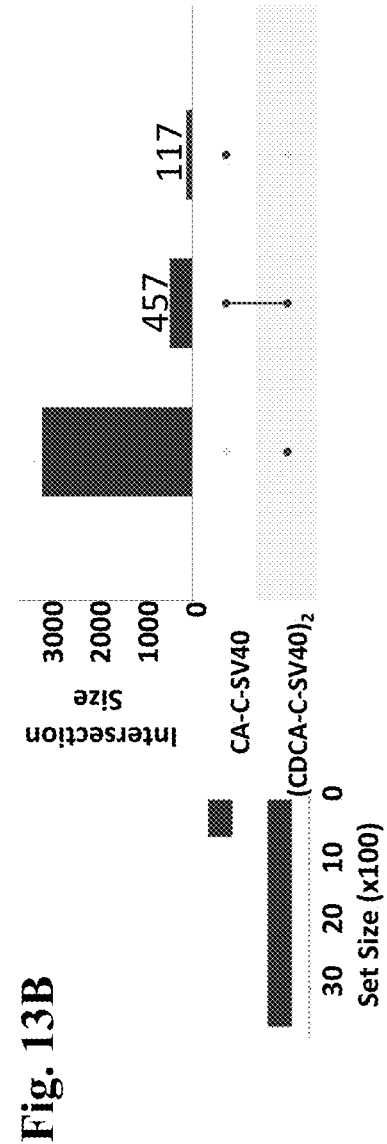
Fig. 13A
Fig. 13B

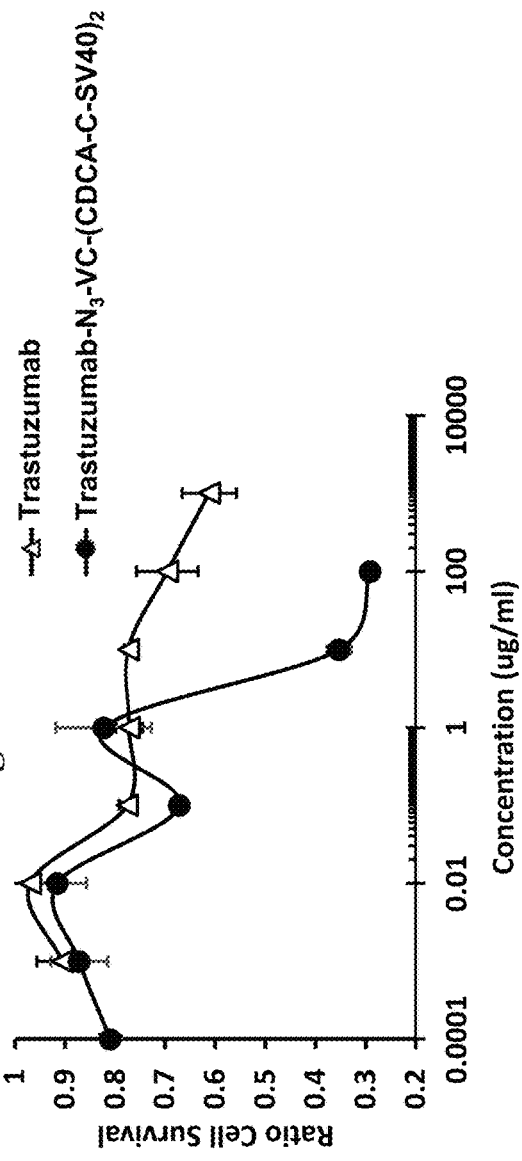
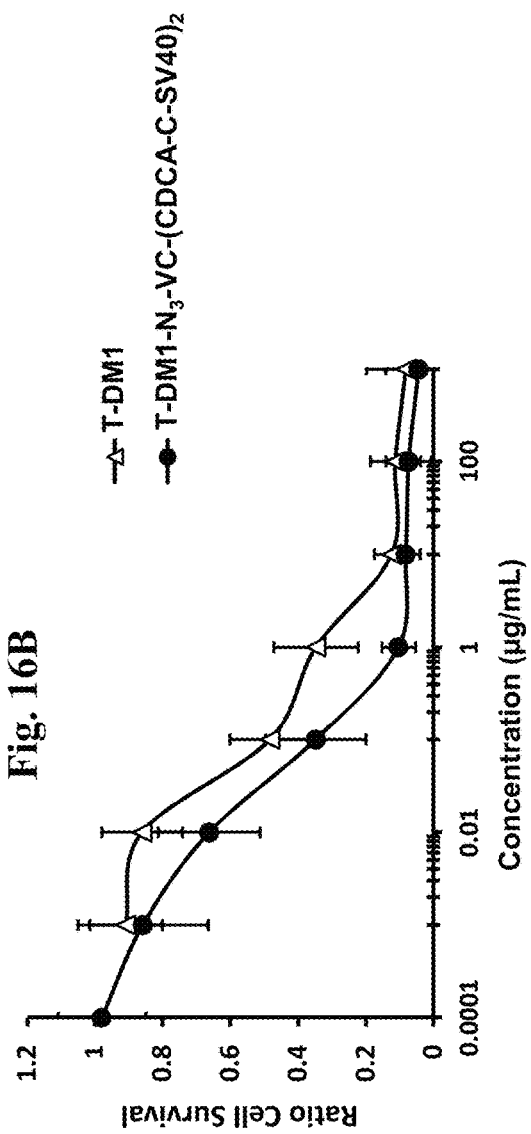
Fig. 16A
Fig. 16B

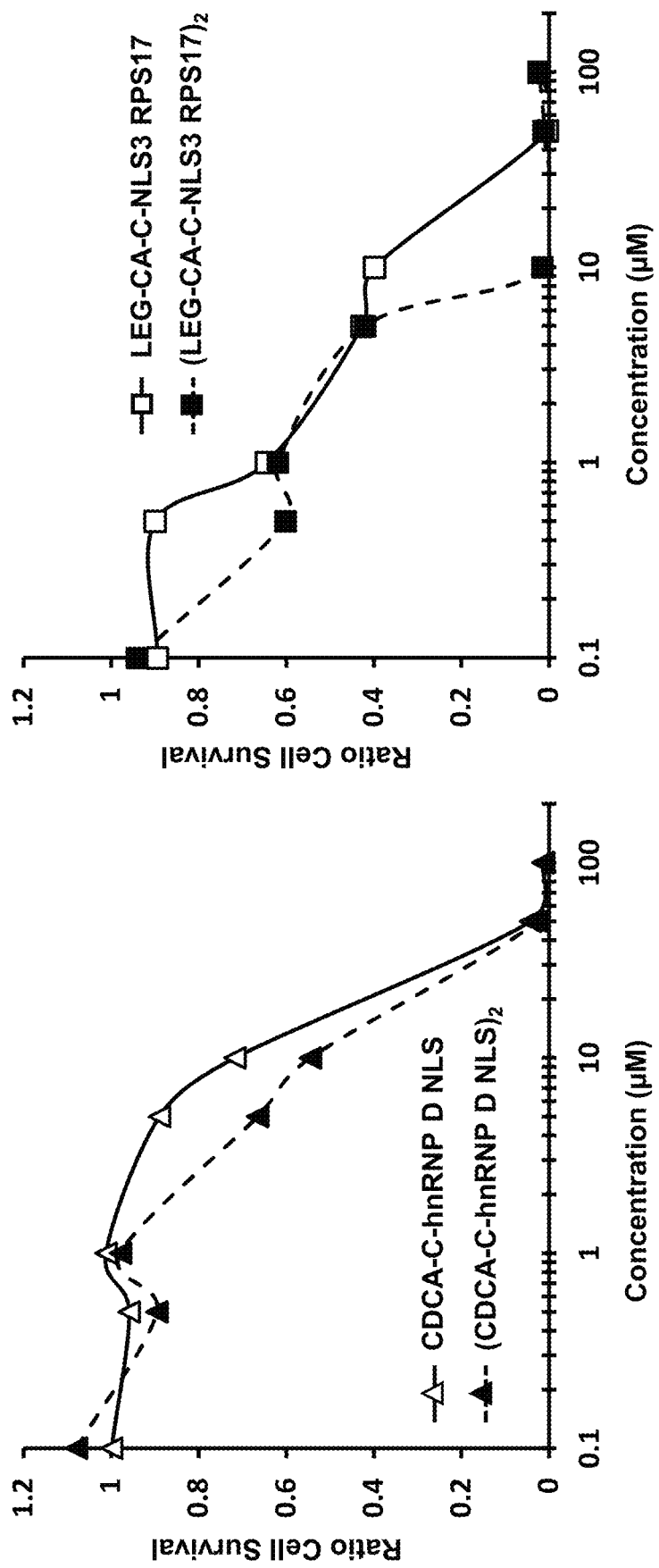

COVALENTLY-MODIFIED STEROID ACID-PEPTIDES HAVING ENHANCED STABILITY AND/OR BIOLOGICAL ACTIVITY

The present description relates to steroid acid-peptide conjugates having enhanced stability and/or biological activity. More specifically, the present description relates to multimeric steroid acid-peptide conjugates, as well as to steroid acid-peptide conjugates having protected thiol groups, and their use as cytotoxic agents, in subunit and cellular vaccines, and for intracellular cargo delivery.

CROSS-REFERENCE TO RELATED APPLICATIONS

This application is a non-provisional application claiming priority to U.S. Patent Application No. 63/476,739, filed Dec. 22, 2022. The contents of which are incorporated by reference in its entirety.

SEQUENCE LISTING

This application contains a sequence listing filed in electronic form as xml file entitled Amended_Sequence_Listing_20751_33.xml, created on Nov. 13, 2023, and having a size of 24,348 bytes. The content of the sequence listing is incorporated herein in its entirety.

BACKGROUND

Bile acid-peptide conjugates represent a new class of biological products that have been shown to enhance the intracellular accumulation of ADCs in their target cells (Beaudoin et al., 2016; Paquette et al., 2018; Lacasse et al., 2020), as well as to improve the immunogenicity of polypeptide antigens upon covalent modification or admixture (WO/2022/126239 and WO/2022/232945). Biological products are particularly sensitive to environmental factors and their regulatory approval generally requires stability testing to define how long they remain safe and effective at particular storage conditions. While a number of modifications may be introduced to biological products to improve their stability, empirical testing is must be undertaken to ensure that the modifications do not abrogate or undesirably attenuate biological activity. Thus, modifications to biological products that both improve their stability and maintain or improve their biological activity are highly desirable.

The present description refers to a number of documents, the contents of which is herein incorporated by reference in their entirety.

SUMMARY

In a first aspect, described herein is a multimeric compound comprising at least two monomers covalently bound to one another, each monomer comprising a steroid acid-peptide conjugate.

In another aspect, described herein is a steroid acid-peptide conjugate comprising a protected thiol group, wherein the stability of the protected thiol group is greater than that of a corresponding steroid acid-peptide conjugate having said thiol group unprotected.

In another aspect, described herein is a composition comprising a multimeric compound or a steroid acid-peptide conjugate as describe herein, for use as antiproliferative drug, a cytotoxic or cytostatic agent, or for improving the immunogenicity and/or presentation of an antigen of interest.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one," but it is also consistent with the meaning of "one or more", "at least one", and "one or more than one".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the expression "consisting essentially of" or "consists essentially of" refers to those elements required for a given embodiment. The expression permits the presence of additional elements that do not materially affect the basic and novel or functional characteristic(s) of that embodiment of the invention, so long as the additional elements do not decrease the performance (e.g., safety profile or efficacy) of that of the corresponding embodiment "consisting of" the recited elements. For greater clarity, the expressions do not exclude the possibility that other additional non-essential ingredients (e.g., excipients, fillers, stabilizers, or inert components) that do not materially change the function or ability of the multimeric compounds or steroid acid-peptide conjugates described herein.

The term "about" is used to indicate that a value includes the standard deviation of error for the device or method being employed in order to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

Other objects, advantages and features of the present description will become more apparent upon reading of the following non-restrictive description of specific embodiments thereof, given by way of example only with reference to the accompanying drawings.

BRIEF DESCRIPTION OF THE DRAWINGS

In the appended drawings:

FIGS. 1A to 1C show the results of the cytotoxic effect of CA-C-SV40 on different cancer cell lines and normal cells. FIG. 1A shows a representative flow cytometry assessment of apoptosis on EL4 lymphoma, CT-26 colon carcinoma, B16 melanoma, and 4T1 breast cancer cells after treatment with the CA-C-SV40 conjugate (cholic acid-SV40 NLS conjugate) (190 µM). FIG. 1B shows a kill curve showing the $EC_{50}$ of CA-C-SV40 on EL4 lymphoma cells. CA (Cholic acid) and SV40 NLS alone did not exhibit any cytotoxic activity at the concentrations tested. FIG. 1C shows a representative flow cytometry assessment of apoptosis on mesenchymal stem cells, macrophages, and bone-marrow derived dendritic cells after treatment with the CA-C-SV40 conjugate (190 μM).

FIGS. 2A to 2C show that CA-C-SV40-mediated cytotoxicity of cancer cells by apoptosis is associated with induction of in situ reactive oxygen species (ROS). FIG. 2A shows a representative flow cytometry assessment of apoptosis on EL4 lymphoma using both PI (for necrosis) and Annexin-V (for apoptosis). Percentages of double-positive stained cells is shown, which represents late apoptotic cells. FIG. 2B shows representative flow cytometry assessment of MitoSOX™ staining to detect ROS production at T=0 (grey), T=1 h, T=4 h and T=8 h. FIG. 2C shows the evaluation CA-C-SV40-induced apoptosis in the presence of N-acetylcysteine (NAC) and MitoTempo™ using both $EC_{50}$ and EC 100 doses.

FIG. 3A shows a schematic representation of the study design with Cytochrome C. FIG. 3B shows a representative flow cytometry assessment of EL4 cell death when treated with CA-C-SV40 (47 μM) admixed with Cytochrome C. FIG. 3C shows a schematic representation depicting the fluorescence resonance energy transfer (FRET) experiment used to demonstrate that CA-C-SV40 induces endosomal escape in EL4 cells. FIG. 3D shows a representative flow cytometry analysis revealing a change in CCF4-AM emitted signal in response to β-lactamase release following CA-C-SV40 treatment in EL4 cells.

FIGS. 4A to 4F show the antitumoral effect of CA-C-SV40 on EL4 lymphoma in vivo. FIG. 4A shows a schematic diagram of the in vivo experiment design in mice. FIG. 4B shows the tumor growth in response to CA-C-SV40 using three different doses (blue [47 μM], green [95 μM], and red [190 μM]). FIG. 4C shows Kaplan-Meier survival curves of the experiment shown in FIG. 4B. FIG. 4D shows a schematic diagram of the in vivo experiment design with immune-checkpoint inhibitors in mice. n=5/group with *P<0.05, and ** P<0.01. FIG. 4E shows the tumor growth assessment of CA-C-SV40 alone (red) in comparison to a combination with anti-PD-1 (green) or anti-CTLA4 (blue). EL4 tumors without any treatment (i.e., PBS) are shown in black, whereas anti-PD-1 treatment alone is in orange and anti-CTLA-4 treatment alone is in purple. FIG. 4F shows Kaplan-Meier survival curves of the experiment displayed in FIG. 4E.

FIG. 7A shows the tumor growth in response to CA-C-NLS1 RPS17 using three different doses (green [47 μM], red [95 μM], and blue [190 μM]). FIG. 7B shows Kaplan-Meier survival curves of the experiment shown in FIG. 7A.

FIGS. 8A and 8B show the antitumoral effect of CA-C-NLS3 RPS17 on EL4 lymphoma in vivo. FIG. 8A shows the tumor growth in response to CA-C-NLS3 RPS17 using three different doses (green [47 μM], red [95 μM], and blue [190 μM]). FIG. 8B shows Kaplan-Meier survival curves of the experiment shown in FIG. 8A.

FIGS. 9A to 9G show the results of a second study of the antitumoral effect of CA-C-SV40 on EL4 lymphoma in vivo. FIG. 9A shows a schematic diagram of the in vivo experiment design in mice with different immune checkpoint inhibitors. For this study, CA-C-SV40 was delivered once every 48 h for a total of 6 injections. FIG. 9B shows the tumor growth assessment of CA-C-SV40 alone in comparison to a combination with anti-PD-1, anti-CTLA4, or anti-CD47, following the injection scheme of FIG. 9A. FIG. 9C shows Kaplan-Meier survival curves of the experiment displayed in FIG. 9B. FIG. 9D shows a schematic diagram of the in vivo experiment design in mice with different immune checkpoint inhibitors. For this study, CA-C-SV40 was delivered once every 24 h for a total of 6 injections. n=5/group with *P<0.05, and ** P<0.01. FIG. 9E shows the tumor growth assessment of CA-C-SV40 alone in comparison to a combination with anti-PD-1, anti-CTLA4, or anti-CD47, following the injection scheme of FIG. 9D. FIG. 9F shows Kaplan-Meier survival curves of the experiment displayed in FIG. 9E. n=5/group with *P<0.05, and ** P<0.01. FIG. 9G shows the tumor volume assessment following the injection scheme of FIG. 9D. For this study, all immune checkpoint inhibitors were delivered simultaneously.

FIGS. 10A to 10G shows that CA-C-SV40-mediated effects involve endogenous immunity. FIG. 10A shows a schematic diagram depicting the timeline for CA-C-SV40/antibody delivery during the in vivo depletion study. FIG. 10B shows the assessment of tumor volume overtime when CA-C-SV40 is delivered to animals treated with anti-CD4, anti-CD8, or anti-NK1.1 antibodies. FIG. 10C shows the Kaplan-Meier survival curve for the experiment in FIG. 10B. n=5/group with *P<0.05, and ** P<0.01. FIG. 10D shows a representative western-blot analyses of HMGB1 secretion following EL4 cells treatment with CA-C-SV40 using different time points and concentrations. FIG. 10E shows a representative Western-blot analyses of HMGB1 secretion following EL4 cells treatment with CA-C-SV40 at 190 μM at shorter timelines (0-2 h). FIG. 10F shows the assessment of ATP secretion levels overtime in response to CA-C-SV40 treatment in EL4 cells. FIG. 10G shows the flow cytometry analysis of $DAPI^+/Calreticulin^+$ EL4 cells in response to CA-C-SV40 treatment. For FIGS. 10B and 10C, n=10/group. For FIG. 10D-10G, n=5/group with *P<0.05,  P<0.01, and * P<0.001.

FIG. 11A shows a representative flow cytometry analysis using 5 different cancer cell lines, EL4 lymphoma, CT-26 colon carcinoma, B16 melanoma, and E0771 and 4T1 breast cancer cell death after treatment with two different (CDCA-C-SV40)$_2$ doses (95 UM and 190 µM). FIG. 11B shows a representative flow cytometry analysis of JIMT-1 breast cancer cell death (left: 10K cells; middle: 20K cells; right: 30K cells after treatment with (CDCA-C-SV40)$_2$ at 6.4 µM (four replicates are shown for each cell concentration). FIG. 11C shows a killing dose response curve conducted on the EL4 lymphoma cells to identify the EC$_{50}$ dose for (CDCA-C-SV40)$_2$. FIG. 11D shows a representative flow cytometry analysis comparing the apoptosis-inducing activities of the CA-C-hnRNPA1 monomer and the (CA-C-hnRNPA1)$_2$ dimer at 50 µM on mesenchymal stromal cells (MSCs). FIG. 11E shows a representative flow cytometry analysis comparing the apoptosis-inducing activities of the (CA-C-hnRNPA1)$_2$ dimer at different concentrations on MSCs. FIG. 11F shows a representative flow cytometry analysis comparing the apoptosis-inducing activities of the (CDCA-C-hnRNPA1)$_2$ dimer at different concentrations on MSCs.

FIG. 12A-12F shows the antitumoral effect of steroid acid-peptide conjugate dimers on in vivo tumors. FIG. 12A shows an assessment of EL4 tumor volume overtime in response to (CDCA-C-SV40)$_2$ administration. FIG. 12B shows the Kaplan-Meier survival curve of the experiment shown in FIG. 12A. FIG. 12C shows the assessment of E0771 tumor volume overtime in response to (CDCA-C-SV40)$_2$ treatment. FIG. 12D shows the Kaplan-Meier survival curve of the experiment shown in FIG. 12C. FIG. 12E shows the assessment of B16 tumor volume overtime in response to (CDCA-C-SV40)$_2$ treatment. FIG. 12F shows the Kaplan-Meier survival curve for the experiment in FIG. 12E. n=5/group.

FIGS. 13A-13E shows the comparison of the effects of steroid acid-peptide conjugate monomers versus and dimers on tumor gene signatures. FIG. 13A shows the number of genes in that are upregulated in EL4 cells treated with CA-C-SV40 (190 µM), (CDCA-C-SV40)$_2$ (6.4 µM), or both. FIG. 13B shows the number of genes in EL4 cells that are downregulated in cells treated with CA-C-SV40 (190 µM), (CDCA-C-SV40)$_2$ (6.4 µM), or both. FIG. 13C shows a list of molecular signatures enriched (up) in EL4 cells in the (CDCA-C-SV40)$_2$-treated group. Coloured circles intensity corresponds to adjusted p-values; size of circles is the ratio of genes in the tested set. FIG. 13D shows a list of molecular signatures enriched (down) in EL4 cells in the (CDCA-C-SV40)$_2$-treated group. Coloured circles intensity corresponds to adjusted p-values; size of circles is the ratio of genes in the tested set. FIG. 13E shows a heat-map depicting regulation of genes involved in oxidative phosphorylation in EL4 cells in response to CA-C-SV40 (190 µM), (CDCA-C-SV40)$_2$ (6.4 µM), or PBS.

FIG. 14 shows a heatmap depicting a list of genes involved in double-stranded DNA repair in EL4 cells treated with CA-C-SV40 (190 µM), (CDCA-C-SV40)$_2$ (6.4 µM), or PBS.

FIG. 15A Gene Set Enrichment Analysis (GSEA) enrichment score of "Regulation of TP53 Activity Reactome" genes in EL4 cells treated with CA-C-SV40 (190 µM) vs. PBS. FIG. 15B shows GSEA enrichment score of "Regulation of TP53 Activity Reactome" genes in (CDCA-C-SV40)$_2$ (6.4 µM) vs. PBS (significant). FIG. 15C shows a heatmap representing the major genes involved in controlling/regulating TP53 expression. The three groups being compared are: PBS, CA-C-SV40 and (CDCA-C-SV40)$_2$. Gene expression is scaled and genes with significant log 2 fold change are shown.

FIG. 16A-16C show the ability of covalently conjugated (CDCA-C-SV40)$_2$ dimers to act as the cytotoxic drug in an antibody-drug conjugate, or to enhance the cytotoxicity of an antibody-drug conjugate. FIG. 16A compares the cytotoxicity in JIMT-1 breast cancer cells after treatment with Trastuzumab without ("Trastuzumab") or with ("Trastuzumab-N$_3$-VC-(CDCA-C-SV40)$_2$") conjugation to the dimer via an N-terminal 6-azido-L-lysine residue "N$_3$" and a protease-cleavable valine-citrulline linker ("VC"). FIG. 16B compares the cytotoxicity in JIMT-1 breast cancer cells after treatment with Trastuzumab emtansine without ("T-DM1") or with ("T-DM1-N$_3$-VC-(CDCA-C-SV40)$_2$") conjugation to the dimer via an N-terminal 6-azido-L-lysine residue "N$_3$" and a protease-cleavable VC linker. FIG. 16C compares the cytotoxicity in JIMT-1 breast cancer cells after treatment with Trastuzumab without conjugation to the dimer ("Trastuzumab"), with conjugation to the dimer via an N-terminal 6-azido-L-lysine residue "N$_3$" but lacking a protease-cleavable VC linker: "Trastuzumab-N$_3$-(CDCA-C-SV40)$_2$", with conjugation to the dimer via a C-terminal 6-azido-L-lysine residue "N$_3$" but lacking a protease-cleavable VC linker: "(CDCA-C-SV40)$_2$-N$_3$-Trastuzumab", or with conjugation to the dimer via a C-terminal 6-azido-L-lysine residue "N$_3$" and a protease-cleavable VC linker: "(CDCA-C-SV40)$_2$-VC-N$_3$-Trastuzumab".

FIG. 17A shows a representative flow cytometry analysis of EL4 lymphoma cell death after treatment with CDCA-A-SV40, CDCA-C/MPA-SV40 (MPA; 3-mercaptopropionic acid), CDCA-C/GSH-SV40 (GSH; glutathione), as compared to the CDCA-C-SV40 monomer and the (CDCA-C-SV40)$_2$ dimer at concentration of 48 M. FIG. 17B shows the results of the same assay as in FIG. 17A but at a concentration of 96 M of steroid acid-peptide conjugate.

FIG. 19A shows a schematic diagram of the experimental design and immunization scheme. For this experiment, (CDCA-C-SV40)$_2$ was delivered twice a week for a total of 6 injections (3 mg/kg). FIG. 19B shows a pictogram of the isolated lungs (black dots represent tumor nodules) following treatments with PBS (Ctl), anti-PD-1 alone, (CDCA-C-SV40)$_2$ alone, or the combination of (CDCA-C-SV40)$_2$ and anti-PD-1, as well the number of B16F10 nodules/per mouse (n=5/group).

FIG. 20A shows a schematic diagram of the experimental design and immunization scheme. For this experiment, (CDCA-C-SV40)$_2$ was delivered twice a week for a total of 6 injections (16 mg/kg). FIG. 20B shows the assessment of tumor volume overtime following treatment with PBS, anti-PD-1, anti-LAG3, anti-PD-1+anti-LAG3, (CDCA-C-SV40)$_2$, (CDCA-C-SV40)$_2$+anti-PD-1, (CDCA-C-SV40)$_2$+anti-LAG3, and (CDCA-C-SV40)$_2$+anti-PD-1+anti-LAG3. FIG. 20C shows Kaplan-Meier survival curve for the experiment in FIG. 20B. For panel FIG. 20C, n=5/group with *P<0.05 and ** P<0.01.

FIG. 21A shows the results of the cytotoxicity in JIMT-1 breast cancer cells after treatment with the steroid acid-peptide conjugate ["CDCA-C-hnRNP D NLS"] monomer and its corresponding dimer ["(CDCA-C-hnRNP D NLS)$_2$"]. FIG. 21B shows the results of the cytotoxicity in JIMT-1 breast cancer cells after treatment with the steroid acid-peptide conjugate ["LEG-CA-C-NLS3 RPS17"] monomer and its corresponding dimer ["(LEG-CA-C-NLS3 RPS17)$_2$"], which contain an N-terminal legumain cleavage site ("LEG"; SEQ ID NO: 18), is compared.

SEQUENCE LISTING

Figure 3A:
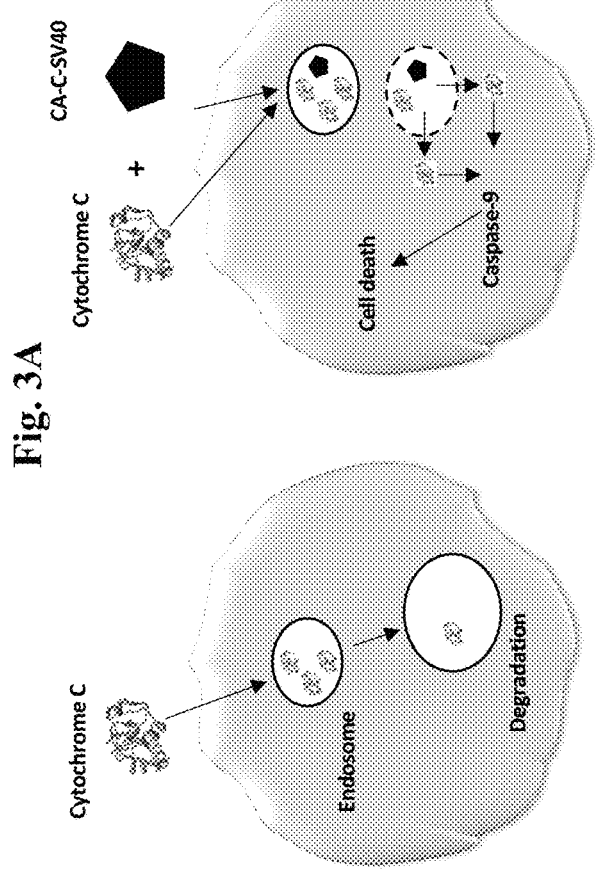
FIGS. 3A and 3B show the ability of CA-C-SV40 to promote endosomal escape and cargo release in the cytoplasm of target cells.

This application contains a Sequence Listing in computer readable form created May 14, 2023. The computer readable form is incorporated herein by reference.

| SEQ ID NO: | Description |
|---|---|
| 1 | CA-C-SV40 |
| 2 | NLS from SV-40 large T-antigen |
| 3 | C-GWG-SV40NLS |
| 4 | C-hnRNPA1 M9 NLS |
| 5 | C-hnRNP D NLS |
| 6 | C-hnRNP M NLS |
| 7 | C-PQBP-1 NLS |
| 8 | C-NLS2-RG Domain RPS17 |
| 9 | C-NLS1 RPS17 |
| 10 | C-NLS2 RPS17 |
| 11 | C-NLS3 RPS17 |
| 12 | C-cMyc NLS |
| 13 | C-HuR NLS |
| 14 | C-Tus NLS |
| 15 | C-Nucleoplasmin NLS |
| 16 | SIINFEKL peptide |
| 17 | CA-A-SV40 |
| 18 | Legumain cleavage site |
| 19 | NLS Consensus Sequence (iii) |
| 20 | Exemplary endosomal escape motif 1 |
| 21 | Exemplary endosomal escape motif 2 |
| 22 | Exemplary endosomal escape motif 3 |
| 23 | Exemplary endosomal escape motif 4 |
| 24 | Exemplary endosomal escape motif 5 |
| 25 | Exemplary endosomal escape motif 6 |

DETAILED DESCRIPTION

The present description relates to steroid acid-peptide conjugates covalently modified for improved stability and/or biological activity as compared to their unmodified counterparts. In a first aspect, the present invention stems from the discovery that thiol-containing steroid acid-peptide conjugates may be subject to stability issues due to thiol oxidation, including the formation of intermolecular disulfide bonds leading to the formation of steroid acid-peptide dimers. Characterization of the dimers revealed not only enhanced stability, but also a synergistic increase in cytotoxicity/apoptosis-inducing activity over their corresponding steroid acid-peptide monomers. Accordingly, in some aspects, the covalent modifications described herein may comprise the formation of multimeric compounds comprising at least two steroid acid-peptide conjugate monomers covalently bound to one another. In some aspects, the covalent modifications described herein may comprise protecting one or more free thiol groups comprised in the steroid acid-peptide conjugate via addition of a cleavable or non-cleavable protecting group, for example to enhance stability over a corresponding steroid acid-peptide conjugate having said thiol group unprotected. In a further aspect, the present invention stems from the discovery that steroid acid-peptide conjugates containing a free thiol group, or a thiol group protected with a cleavable protecting group, may exhibit increased biological activity as comparted to a steroid acid-peptide conjugate lacking the corresponding thiol group, or in which the thiol group is protected via a non-cleavable protecting group. Accordingly, in some aspects, the covalent modifications described herein may comprise protecting one or more free thiol groups comprised in the steroid acid-peptide conjugate via addition of a cleavable protecting group, wherein biological activity of the steroid acid-peptide conjugate increases upon intracellular cleavage of the protecting group.

In some aspects, described herein is a multimeric compound comprising at least two monomers covalently bound to one another (e.g., via a direct linkage), each monomer comprising a steroid acid-peptide conjugate. As used herein, the expression "multimeric compound" refers to a single molecular entity chemically synthesized to tether together at least two steroid acid-peptide conjugate monomers in relatively close proximity such that the biological activity (e.g., cytotoxicity and/or ability to enhance antigen presentation/immunogenicity) of the multimeric compound is increased relative to steroid acid-peptide conjugate monomers. For greater clarity, the multimeric compounds described herein are synthesized upstream of any further conjugation reaction to a carrier molecule, and are structurally and functionally distinct from carrier molecules conjugated to two or more steroid acid-peptide monomers. As used herein, the expression "comprising as least two monomers" and "comprising two monomers" may be used interchangeably and refer to a multimeric compound described herein that contains at least two monomers (e.g., a dimer), but do not exclude multimeric compounds described herein containing more than two monomers (e.g., trimers, tetramers, etc.).

In some embodiments, the multimeric compound described herein may comprise at least two steroid acid-peptide conjugate monomers covalently bound to one another via their peptide moieties. In some embodiments, the at least two monomers may be covalently conjugated via an intermolecular bond formed between functional groups of amino acid side chains comprised in each of the at least two monomers. In some embodiments, the at least two monomers may be covalently conjugated via an intermolecular disulfide bond resulting from oxidation of thiol groups present in each monomer prior to multimerization. In some embodiments, the monomers may be covalently bound via a cleavable linkage. As used herein, the expression "cleavable linkage", "cleavable bond", or "cleavably bound", refers to chemical linkages that may be severed intracellularly (e.g., endosomal, cytosolic, or nuclear), or in proximity to a tissue/cellular microenvironment. In some embodiments, the cleavable linkage may be an enzymatically cleavable linker (e.g., via cathepsin-[e.g., cathepsin B], valine-citrulline, legumain cleavage site (SEQ ID NO: 18), or matrix metalloproteinase-mediated cleavage), a photocleavable linker, a redox-sensitive linker (e.g., disulfide linkage), or a pH-sensitive linker (e.g., hydrazine linked). For example, the extracellular environments surrounding certain tissues may consist of reducing agents which destroy the link between steroid-acid peptide conjugate monomers. In other scenarios, internalization of the multimeric compound described herein may destroy the linker via lowering of the pH in the endosome, and/or via an intracellular/endosomal protease. Furthermore, tumor microenvironments may have a more acidic pH due to increased growth and metabolism and subsequent accumulation of lactic acid. In some scenarios, certain tumors may secrete proteases which cleave the linker between steroid acid-peptide conjugate monomers.

In some embodiments, the multimeric compound described herein may be a multimer of a single species of steroid acid-peptide monomer. Such multimeric compounds may be advantageous in terms of synthesis, manufacturing and end product homogeneity.

In some embodiments, the multimeric compound described herein may be a dimer, trimer, tetramer, pentamer, hexamer, heptamer, octamer, nonamer, or decamer. Such multimeric compounds may be synthesized, for example, using functionalized branched polymers such as star-shaped polymers described in the art.

In some aspects, described herein is a steroid acid-peptide conjugate comprising a protected thiol group, wherein the stability of the protected thiol group is greater than that of a corresponding steroid acid-peptide conjugate having said thiol group unprotected. In some embodiments, the protected thiol group may be comprised in a side of chain of an amino acid (e.g., cysteine, homocysteine, and thiol-containing synthetic amino acids) comprised in the peptide.

In some embodiments, the protected thiol group may be protected with a cleavable protecting group. As used herein, the expression "cleavable protecting group" or "releasable protecting group" refers to a protecting group that may be severed intracellularly or in proximity to a tissue/cellular microenvironment. In some embodiments, the cleavable protecting groups may be a photocleavable linker, a redox-sensitive linker (e.g., disulfide linkage), or a pH-sensitive linker (e.g., hydrazine linked). In some embodiments, the protected thiol group may be protected with a protecting group via a disulfide bond. In some embodiments, the protected thiol group may be protected with a non-cleavable protecting group.

In some embodiments, the steroid acid-peptide conjugate comprising a protected thiol group may be comprised in a multimeric compound as described herein. In some embodiments, at least two monomers of a multimeric compound described herein may comprise a steroid acid-peptide conjugate in which the peptide comprises a cysteine residue having a protected thiol group. In some embodiments, the dimerization or multimerization (e.g., via an intermolecular disulfide bond) with a further steroid acid-peptide may serve as a thiol protecting group.

In some embodiments, the peptides described herein may comprise one or more domains that impart an additional functionality to the peptide in the steroid acid-peptide conjugates described herein. As used herein, a "domain" generally refers to a part of a protein having a particular functionality. Some domains conserve their function when separated from the rest of the protein, and thus can be used in a modular fashion. The modular characteristic of many protein domains can provide flexibility in terms of their placement within the peptides described herein. However, some domains may perform better when engineered at certain positions of the peptide (e.g., at the N- or C-terminal region, or therebetween). The position of the domain within its endogenous protein may be an indicator of where the domain should be engineered within the peptide.

In some embodiments where non-specific delivery may be desired, the peptides described herein may comprise a protein transduction domain (PTD) that stimulates endocytosis, endosomal formation, or intracellular delivery in a non-cell-specific manner. In some embodiments, the peptides described herein may comprise a subcellular targeting signal promoting targeting of the multimeric compound or steroid acid-peptide conjugate described herein to a specific subcellular compartment.

In some embodiments, the peptide may comprise a nuclear localization signal (NLS) that targets the steroid acid-peptide conjugate to the nucleus. In some embodiments, the nuclear localization signals described herein may comprise or be derived from the NLS from SV-40 large T-antigen (e.g., PKKKRKV; SEQ ID NO: 1 or 2) or from other classical NLSs. In some embodiments, the nuclear localization signals described herein may comprise or be derived from non-classical NLS (e.g., acidic M9 domain in the hnRNP A1 protein; the sequence KIPIK in yeast transcription repressor Matα2; PY-NLS; ribosomal NLS; or the complex signals of U snRNPs). In some embodiments, the nuclear localization signal described herein comprises or consists essentially of the amino acid sequence of any one of SEQ ID NOs: 1 to 15, or any portion thereof. In some embodiments, the nuclear localization signal described herein comprises or consists essentially of a nuclear localisation signal which is SV40 NLS (e.g., comprised in SEQ ID NO: 1 or 2), GWG-SV40 NLS (e.g., comprised in SEQ ID NO: 3), hnRNPA1 M9 NLS (e.g., comprised in SEQ ID NO: 4), hnRNP D NLS (e.g., comprised in SEQ ID NO: 5), hnRNP M NLS (e.g., comprised in SEQ ID NO: 6), PQBP-1 NLS (e.g., comprised in SEQ ID NO: 7), NLS2-RG Domain RPS17 (e.g., comprised in SEQ ID NO: 8), NLS1 RPS17 (e.g., comprised in SEQ ID NO: 9), NLS2 RPS17 (e.g., comprised in SEQ ID NO: 10), NLS3 RPS17 (e.g., comprised in SEQ ID NO: 11), cMyc NLS (e.g., comprised in SEQ ID NO: 12), HuR NLS (e.g., comprised in SEQ ID NO: 13), Tus NLS (e.g., comprised in SEQ ID NO: 14), or Nucleoplasmin NLS (e.g., comprised in SEQ ID NO: 15). In some instances, the SEQ ID NOS referred to above comprise an N-terminal cysteine residue that was used to facilitate conjugation to the carrier molecule (e.g., the thiol group of the N-terminal cysteine residue). Thus, in some embodiments, the NLS sequences referred to herein may exclude an N-terminal cysteine residue comprised in any one of SEQ ID NOs: 1 to 15. In some embodiments, other functional groups added or inserted (e.g., towards the N to C terminal portions of the peptides described herein) to facilitate steroid acid-peptide conjugation to a given carrier molecule are also envisaged (e.g., carboxyl groups, synthetic amino acids, etc.). For example, the peptide may include a C-terminal amide and/or an N-terminal cysteine. In some embodiments, peptides described herein may not comprise an endosomal escape motif, or protein transduction domain, or cell penetrating motif.

In some embodiments, the nuclear localization signals described herein may comprise the general consensus sequence: (i) K(K/R)X(K/R); (ii) (K/R)(K/R)X$_{10-12}$(K/R)$_{3/5}$, wherein (K/R)$_{3/5}$ represents three lysine or arginine residues out of five consecutive amino acids; (iii) KRX$_{10-12}$KRRK (SEQ ID NO: 19); (iv) KRX$_{10-12}$K(K/R)(K/R); or (v) KRX$_{10-12}$K(K/R)X(K/R), wherein X is any amino acid (Sun et al., 2016).

In some embodiments, the peptide does not include an endosomal escape motif (e.g. -GFFG (SEQ ID NO: 20), -GWG, -GFWG (SEQ ID NO: 21), -GFWFG (SEQ ID NO: 22), -GWWG (SEQ ID NO: 23), -GWGGWG (SEQ ID NO: 24), and -GWWWG (SEQ ID NO: 25)), or protein transduction, or cell penetrating motif (such as a cell penetrating peptide).

In some embodiments, peptides comprised in steroid acid-peptide conjugates described herein may comprise or consist of a cationic peptide (e.g., a non-cell-penetrating cationic peptide). In some embodiments, peptides comprised in steroid acid-peptide conjugates described herein may comprise a non-immunogenic peptide. In some embodiments, the carrier molecule is not a polypeptide antigen. In some embodiments, the peptide may be a water-soluble peptide, wherein conjugation of the peptide to the steroid acid increases the water solubility of the steroid acid-peptide moiety as compared to the steroid acid moiety alone.

In some embodiments, the multimeric compounds and/or steroid acid-peptide conjugates described herein possess cytotoxic or cytostatic activity against mammalian cells, such as but not limited to immune cells or tumor/cancer cells. In some cases, induction of cytotoxicity is exhibited via induction of a mechanism of cell death. In some cases, the multimeric compounds and/or steroid acid-peptide conjugates described herein induce apoptosis or late apoptosis in cells. In some cases, the multimeric compounds and/or steroid acid-peptide conjugates described herein induce activation of the reactive oxygen species (ROS) pathway or release of intracellular ROS.

In some embodiments, steroid acids described herein may be or comprise a bile acid (e.g., a primary bile acid or a secondary bile acid). In some embodiments, steroid acids described herein may enhance endocytosis and/or endosomal escape when internalized. Without being bound by theory, steroid acids (e.g., bile acids and bile acid analogs) have been shown to be utilized/exploited by viruses to facilitate their infection of host cells, such as by increasing their endocytic uptake and/or endosomal escape to gain access to the cytosol (Shivanna et al., 2014; Shivanna et al., 2015; Murakami et al., 2020). For example, bile acids have been shown to trigger the enzyme acid sphingomyelinase (ASM) to cleave sphingomyelin to ceramide on the inner leaflet of endosomes. Increased amounts of ceramide destabilize membranes and facilitate endosomal escape. In some embodiments, steroid acids described herein comprise those that trigger ceramide accumulation on the inner leaflet of endosomes, thereby destabilizing endosomal membranes and facilitating endosomal escape of the steroid acid upon intracellular delivery. In some embodiments, steroid acids described herein comprise those that trigger increased acid sphingomyelinase (ASM)-mediated cleavage of sphingomyelin to form ceramide.

In some embodiments, the steroid acid comprised in multimeric compounds and/or steroid acid-peptide conjugates described herein may comprise or consist of a bile acid (e.g., a primary bile acid or a secondary bile acid). In some embodiments, the steroid acid may be or comprise: cholic acid (CA), chenodeoxycholic acid (CDCA), deoxycholic acid (DCA), lithocholic acid (LCA), glycodeoxycholic acid (GDCA), glycocholic acid (GCA), taurocholic acid (TCA), glycodeoxycholic acid (CDCA), glycochenodeoxycholic acid (GCDCA), taurodeoxycholic acid (TDCA), glycolithocholic acid (GLCA), taurolithocholic acid (TLCA), taurohyodeoxycholic acid (THDCA), taurochenodeoxycholic acid (TCDCA), ursocholic acid (UCA), tauroursodeoxycholic acid (TUDCA), ursodeoxycholic acid (UDCA), glycoursodeoxycholic acid (GUDCA), or any analog thereof that: induces endocytosis; triggers ceramide accumulation on the inner leaflet of endosomes; triggers increased acid sphingomyelinase (ASM)-mediated cleavage of sphingomyelin to form ceramide; and/or has a hydrophobicity greater than that of cholic acid.

Hydrophobic bile acids such as GCDCA, TCA, GCA, and CA (but not hydrophilic bile acids such as UDCA) were shown to increase GII.3 human norovirus infection and replication in host intestinal cells by enhancing endosomal uptake and endosomal escape via ASM-mediated ceramide accumulation on the apical membrane (Murakami et al., 2020). In some embodiments, the steroid acid described herein may comprise or consist of a bile acid or bile acid analog that is more hydrophobic than cholic acid. In some embodiments, the steroid acid described herein comprises or consists of a bile acid or bile acid analog that is more hydrophobic than cholic acid (e.g., CDCA, DCA, LCA, TCA, TDCA, TCDCA, GCA, GDCA, or GCDCA; Hanafi et al., 2018).

In some embodiments, the steroid acid may be conjugated to the peptide, for example at or towards a free N-terminal or C-terminal amino group of the peptide or at some other functional group within the peptide. In some embodiments, the steroid acids described herein may be conjugated at or towards the N- or C-terminus of the peptides described herein.

In some embodiments, the multimeric compounds and/or steroid acid-peptide conjugates described herein may be conjugated to a carrier molecule. In some embodiments, the carrier molecule may be a protein carrier (e.g., antibody or receptor ligand); polysaccharide carrier; polynucleotide carrier (e.g., aptamer); polynucleotide analog carrier; polyethylene glycol carrier; lipid carrier; or other biocompatible carrier. Advantageously, when a carrier molecule (e.g., a protein carrier such as an antibody) is conjugated to a multimeric compound or a steroid acid-peptide conjugate described herein, the multimeric compound or the steroid acid-peptide conjugate may exhibit diminished cytotoxic activity. However, upon release of the multimeric compound or the steroid acid-peptide conjugate from the carrier molecule, the multimeric compound or the free steroid acid-peptide conjugate may exhibit increased cytotoxic activity. In some embodiments, where the carrier molecule is a targeting molecule, and the multimeric compound and/or one of more of the steroid acid-peptide monomers, may be released from the carrier molecule upon (or subsequent to) binding of the carrier molecule to a specific target.

In some embodiments, the carrier molecule may be releasably bound to the multimeric compound and/or to steroid acid-peptide conjugate via a releasable linker. In some embodiments, the releasable linker may be a cleavable linker (such as an enzymatically cleavable linker, e.g., via cathepsin-[e.g., cathepsin B], valine-citrulline, legumain cleavage site (SEQ ID NO: 18), or matrix metalloproteinase-mediated cleavage), a photocleavable linker, a redox-sensitive linker (e.g., disulfide link or bond), or a pH-sensitive linker (e.g., hydrazine linked). For example, the extracellular environments surrounding certain tissues may consist of reducing agents which destroy the link between the steroid-acid peptide conjugate or multimeric compound and the carrier molecule. In other scenarios, internalization of the multimeric compound or the steroid acid-peptide conjugate linked to the carrier molecule may result in cleavage of the linker via endosomal, cytosolic, or nuclear proteases. In other scenarios, internalization of the multimeric compound or the steroid acid-peptide conjugate linked to the carrier molecule may destroy the linker via lowering of the pH in the endosome. Furthermore, tumor microenvironments may have a more acidic pH due to increased growth and metabolism and subsequent accumulation of lactic acid. In some scenarios, certain tumors may secrete proteases which cleave the linker between the steroid acid-peptide conjugate and the carrier molecule. Nevertheless, upon release of the steroid acid-peptide conjugate from the carrier molecule, the steroid acid-peptide may exert its cytotoxic activity.

In some embodiments, the carrier molecule described herein may be a targeting molecule. The carrier or target molecule may therefore transport the multimeric compound or steroid acid-peptide conjugate to a specific target (e.g., cell or tissue), whereby the multimeric compound or steroid acid-peptide conjugate is released from the carrier molecule upon (or subsequently to) binding of the carrier molecule to a specific target or upon internalization of the complex. For example, the carrier may be a targeting molecule, such as an antibody, which targets a specific cell type, tissue, or a tumor. Examples of antibodies include but are not limited to monoclonal antibodies against B cells (e.g., anti-CD20 [rituximab, ocrelizumab, ofatumumab, or obinutuzumab]) or T cells. In some embodiments, the carrier molecule may be a therapeutic monoclonal antibody, such as 3F8, Abagovomab, Abituzumab, Adecatumumab, Alemtuzumab, Altumomab, Amatuximab, Amivantamab, Anatumomab, Arcitumomab, Ascrinvacumab, Atezolizumab, Balstilimab, Bavituximab, Bectumomab, Belantamab, Bevacizumab, Bivatuzumab, Blinatumomab, Botensilimab, Brentuximab, Brontictuzumab, Cantuzumab, Cantuzumab, Capromab, Carotuximab, Catumaxomab, Cetuximab, Cirmtuzumab, Citatuzumab, Cixutumumab, Clivatuzumab, Cofetuzumab, Conatumumab, Dacetuzumab, Dalotuzumab, Daratumumab, Demcizumab, Denintuzumab, Depatuxizumab, Derlotuximab, Detumomab, Dinutuximab, Drozitumab, Duligotumab, Dusigitumab, Duvortuxizumab, Ecromeximab, Edrecolomab, Elotuzumab, Emactuzumab, Emibetuzumab, Enfortumab, Enoblituzumab, Enoticumab, Ensituximab, Ertumaxomab, Etaracizumab, Farletuzumab, Ficlatuzumab, Figitumumab, Flanvotumab, Flotetuzumab, Futuximab, Ganitumab, Gemtuzumab, Girentuximab, Glembatumumab, Ibritumomab, Icrucumab, Igovomab, Imgatuzumab, Indatuximab, Inotuzumab, Intetumumab, Ipilimumab, Iratumumab, Isatuximab, Istiratumab, Labetuzumab, Lexatumumab, Lifastuzumab, Lilotomab, Lintuzumab, Loncastuximab, Lorvotuzumab, Lucatumumab, Lumretuzumab, Mapatumumab, Margetuximab, Matuzumab, Milatuzumab, Minretumomab, Mitumomab, Moxetumomab, Nacolomab, Naptumomab, Narnatumab, Naxitamab, Necitumumab, Nesvacumab, Nimotuzumab, Nivolumab, Nofetumomab, Obinutuzumab, Ocaratuzumab, Ofatumumab, Olaratumab, Onartuzumab, Ontuxizumab, Onvatilimab, Opicinumab, Oportuzumab, Oportuzumab, Oregovomab, Oregovomab, Orticumab, Otelixizumab, Otilimab, Otlertuzumab, Otlertuzumab, Oxelumab, Ozanezumab, Ozoralizumab, Pagibaximab, Palivizumab, Pamrevlumab, Panitumumab, Panitumumab, Pankomab, Pankomab, Panobacumab, Parsatuzumab, Parsatuzumab, Pascolizumab, Pasotuxizumab, Pateclizumab, Patritumab, Patritumab, PDR001, Pembrolizumab, Pembrolizumab, Pemtumomab, Pemtumomab, Perakizumab, Pertuzumab, Pertuzumab, Pexelizumab, Pidilizumab, Pinatuzumab, Pinatuzumab, Pintumomab, Pintumomab, Placulumab, Plozalizumab, Pogalizumab, Polatuzumab, Polatuzumab, Ponezumab, Porgaviximab, Prasinezumab, Prezalizumab, Prezalumab, Priliximab, Pritoxaximab, Pritumumab, Pritumumab, PRO, Quilizumab, Racotumomab, Racotumomab, Radretumab, Radretumab, Rafivirumab, Ralpancizumab, Ramucirumab, Ramucirumab, Ranevetmab, Ranibizumab, Ravagalimab, Ravulizumab, Raxibacumab, Refanezumab, Regavirumab, Regdanvimab, Relatlimab, Remtolumab, Reslizumab, Rilotumumab, Rilotumumab, Rinucumab, Risankizumab, Rituximab, Rituximab, Rivabazumab, Rmab, Robatumumab, Robatumumab, Roledumab, Romilkimab, Romosozumab, Rontalizumab, Rosmantuzumab, Rosmantuzumab, Rovalpituzumab, Rovalpituzumab, Rovelizumab, Rozanolixizumab, Ruplizumab, SA237, Sacituzumab, Sacituzumab, Samalizumab, Samrotamab, Sarilumab, Satralizumab, Satumomab, Satumomab, Secukinumab, Selicrelumab, Seribantumab, Seribantumab, Setoxaximab, Setrusumab, Sevirumab, SGN-CD19A, SHP647, Sibrotuzumab, Sibrotuzumab, Sifalimumab, Siltuximab, Siltuximab, Simtuzumab, Simtuzumab, Siplizumab, Sirtratumab, Sirukumab, Sofituzumab, Sofituzumab, Solanezumab, Solitomab, Solitomab, Sonepcizumab, Sontuzumab, Sotrovimab, Spartalizumab, Spesolimab, Stamulumab, Sulesomab, Suptavumab, Sutimlimab, Suvizumab, Suvratoxumab, Tabalumab, Tacatuzumab, Tacatuzumab, Tadocizumab, Tafasitamab, Talacotuzumab, Talizumab, Talquetamab, Tamtuvetmab, Tanezumab, Taplitumomab, Taplitumomab, Tarextumab, Tarextumab, Tavolimab, Teclistamab, Tefibazumab, Telimomab, Telisotuzumab, Telisotuzumab, Tenatumomab, Tenatumomab, Teneliximab, Teplizumab, Tepoditamab, Teprotumumab, Teprotumumab, Tesidolumab, Tetulomab, Tezepelumab, TGN1412, Tibulizumab, Tigatuzumab, Tigatuzumab, Tildrakizumab, Timigutuzumab, Timolumab, tiragolumab, Tiragotumab, Tislelizumab, Tisotumab, Tisotumab, Tixagevimab, TNX-650, Tocilizumab, Tomuzotuximab, Toralizumab, Tosatoxumab, Tositumomab, Tositumomab, Tovetumab, Tovetumab, Tralokinumab, Trastuzumab, Trastuzumab, Trastuzumab, Trastuzumab, TRBS07, Tregalizumab, Tremelimumab, Trevogrumab, Tucotuzumab, Tucotuzumab, Tuvirumab, Ublituximab, Ublituximab, Ulocuplumab, Urelumab, Urtoxazumab, Ustekinumab, Utomilumab, Vadastuximab, Vanalimab, Vandortuzumab, Vandortuzumab, Vantictumab, Vantictumab, Vanucizumab, Vanucizumab, Vapaliximab, Varisacumab, Varlilumab, Vatelizumab, Vedolizumab, Veltuzumab, Veltuzumab, Vepalimomab, Vesencumab, Visilizumab, Vobarilizumab, Volociximab, Vonlerolizumab, Vopratelimab, Vorsetuzumab, Vorsetuzumab, Votumumab, Votumumab, Vunakizumab, Xentuzumab, XMAB-5574, Zalutumumab, Zalutumumab, Zanolimumab, Zatuximab, Zenocutuzumab, Ziralimumab, Zolbetuximab, or Zolimomab.

In some embodiments, the multimeric compound or the steroid acid-peptide conjugate may be bound to a carrier molecule that includes an antibody bound to a further cytotoxic agent or drug (such a chemotherapeutic drug or agent). In some embodiments, the multimeric compound or the steroid acid-peptide conjugate is bound to one or more antibody-drug conjugates (ADCs). Antibody binding to the further cytotoxic agent or drug may be releasable (e.g., cleavable) or non-releasable (e.g., non-cleavable). In some embodiments, the multimeric compound or the steroid acid-peptide conjugate described herein may be the only cytotoxic or cytostatic agent releasably bound to the carrier molecule.

In some embodiments, the multimeric compound or the steroid acid-peptide conjugate described herein may be comprised in a solution at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, or 500 micromolar.

In some aspects, described herein is a composition comprising the multimeric compound or the steroid acid-peptide conjugate described herein at concentration sufficient for their intended biological activities. In some embodiments, the composition may be formulated within a hydrogel, liposome, or nanoparticle (e.g., lipid nanoparticle). In some embodiments, prodrugs of the multimeric compounds or steroid acid-peptide conjugates are contemplated herein and may be encompassed in the expressions "multimeric compound" and "steroid acid-peptide conjugate", to the extent that administration of the prodrug results in the in vivo generation of the multimeric compound or steroid acid-peptide conjugate described herein. In some embodiments, the composition may further comprise a pharmaceutically or physiologically acceptable carrier, adjuvant, and/or excipient. In some embodiments, the composition may be adapted or formulated for oral, intravenous, intranasal, intramuscular, subcutaneous, intradermal, intratumoral, intracranial, topical, intrarectal administration, or any other route of administration. In some embodiments, the composition is administered intranasally, for example via a nebulizer (e.g., PARI LC PLUS®).

In some embodiments, the composition described herein may be for use in the treatment of cancer, an autoimmune disease, or any other disease or disorder ameliorated by treatment with an antiproliferative drug in a subject; or for use as a cytotoxic or cytostatic agent; or for the manufacture of a medicament for same. In some embodiments, the composition described herein may be for use in combination with immune-checkpoint inhibitor or immunosuppressive therapy. In some embodiments, described herein is a method for treating cancer, proliferative disease, or any other disease or disorder ameliorated by treatment with an antiproliferative drug in a subject (e.g., human), the method including administering the composition, multimeric compound, or steroid acid-peptide conjugate as defined herein to the subject. The cancer may include any cancer such as but not limited to breast, colon, prostate, blood, lymphoma, lung, skin, brain, pancreatic, kidney, liver, cancer or any cancer of a tissue or organ. In some aspects, the cancer may include a solid or liquid tumor. In some embodiments, described herein is a method for treating an autoimmune disease in a subject (e.g., human), the method including administering the composition, multimeric compound, or steroid acid-peptide conjugate as defined herein to the subject. In some embodiments, the autoimmune disease may include but is not limited to multiple sclerosis, rheumatoid arthritis, or systemic lupus erythematosus. In some embodiments, the method described herein includes combining the composition, multimeric compound, or steroid acid-peptide conjugate with any known drug for the treatment of said cancer or autoimmune disease or in combination with standard-of-care, such as but not limited to immunosuppressive drugs, immune-checkpoint inhibitors, or chemotherapies. In some aspects, the composition or conjugate is at a dose of at least 0.5, 1, 2, 3, 4, 5, 10, 25, 50, 75, 100, 125, 150, 175, 200, 250, 300, 350, 400, 450, or 500 mg/kg.

In some embodiments, the composition described herein may be for use in improving the immunogenicity and/or presentation of an antigen, wherein the antigen is covalently conjugated to or admixed with the multimeric compound or the steroid acid-peptide conjugate; or for use in the manufacture of a vaccine or an immunostimulatory composition.

In some embodiments, the composition described herein may be administered alone directly into a specific microenvironment. For example, the steroid acid-peptide conjugate may be locally administered into the skin (e.g., subcutaneous injection) or intratumorally.

In some embodiments, the multimeric compounds or steroid acid-peptide conjugate described herein may be used or may be present in a composition described herein at an effective concentration of at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, or 500 micromolar. As used herein, the term "effective concentration" refers to the concentration of free or freeable multimeric compound or steroid acid-peptide monomers. For example, when the steroid acid-peptide conjugate is present as free monomer molecules that are not multimerized or are not bound to a carrier molecule, the effective concentration is the concentration of free of the steroid acid-peptide monomers. For example, when the steroid acid-peptide monomers are releasably bound to a multimeric compound or to carrier molecule, then the effective concentration of the steroid-acid peptide conjugates refers to the concentration of the released steroid acid-peptide monomers. In contrast, when the steroid acid-peptide monomers are bound to a multimeric compound or carrier molecule in a non-cleavable fashion, then the effective concentration refers to the concentration of the multimeric compound or the carrier molecule.

ITEMS

In some aspects, described herein are one or more of the following items:

1. A multimeric compound comprising at least two monomers covalently bound to one another (e.g., via a direct linkage), each monomer comprising a steroid acid-peptide conjugate.
2. The multimeric compound of item 1, wherein the at least two monomers are covalently conjugated via their peptides.
3. The multimeric compound of item 2, wherein the at least two monomers are covalently conjugated via an intermolecular bond formed between functional groups of amino acid side chains comprised in each of the at least two monomers.
4. The multimeric compound of any one of items 1 to 3, wherein the at least two monomers are covalently conjugated via an intermolecular disulfide bond resulting from oxidation of thiol groups present in each monomer prior to multimerization.
5. The multimeric compound of any one of items 1 to 4, wherein the monomers are covalently bound via a cleavable or non-cleavable linkage.
6. The multimeric compound of any one of items 1 to 5, which is a multimer of a single species of steroid acid-peptide monomer.
7. The multimeric compound of any one of items 1 to 6, wherein the multimeric compound is a dimer, trimer, tetramer, pentamer, hexamer, heptamer, octamer, nonamer, or decamer.
8. The multimeric compound of any one of items 1 to 7, wherein the at least two monomers comprise a steroid acid-peptide conjugate in which the peptide comprises a cysteine residue having a protected thiol group.
9. The multimeric compound of item 8, wherein the protected thiol group is protected with a cleavable protecting group.
10. The multimeric compound of any one of items 1 to 9, wherein the at least two monomers comprise a steroid acid-peptide conjugate in which the peptide: (i) comprises a protein transduction domain that stimulates endocytosis and/or endosomal formation; (ii) comprises a subcellular targeting signal; (iii) is a cationic peptide (e.g., a non-cell-penetrating cationic peptide); (iv) is a non-immunogenic peptide; or (v) any combination of (i) to (iv).

11. The multimeric compound of item 10, wherein the subcellular targeting signal is a nuclear localization signal (NLS).

12. The multimeric compound of item 11, wherein the peptide is or comprises a nuclear localization signal which is a classical NLS (e.g., NLS from SV-40 large T-antigen (e.g., PKKKRKV; SEQ ID NO: 1 or 2) or from other classical NLSs) or a non-classical NLS (e.g., acidic M9 domain in the hnRNP A1 protein; the sequence KIPIK in yeast transcription repressor Matα2; PY-NLS; ribosomal NLS; and the complex signals of U snRNPs).

12. The multimeric compound of item 11, wherein the peptide is or comprises a nuclear localization signal which is a/an: SV40 NLS (e.g., comprised in SEQ ID NO: 1 or 2), GWG-SV40NLS (e.g., comprised in SEQ ID NO: 3), hnRNPA1 M9 NLS (e.g., comprised in SEQ ID NO: 4), hnRNP D NLS (e.g., comprised in SEQ ID NO: 5), hnRNP M NLS (e.g., comprised in SEQ ID NO: 6), PQBP-1 NLS (e.g., comprised in SEQ ID NO: 7), NLS2-RG Domain RPS17 (e.g., comprised in SEQ ID NO: 8), NLS1 RPS17 (e.g., comprised in SEQ ID NO: 9), NLS2 RPS17 (e.g., comprised in SEQ ID NO: 10), NLS3 RPS17 (e.g., comprised in SEQ ID NO: 11), cMyc NLS (e.g., comprised in SEQ ID NO: 12), HuR NLS (e.g., comprised in SEQ ID NO: 13), Tus NLS (e.g., comprised in SEQ ID NO: 14), or Nucleoplasmin NLS (e.g., comprised in SEQ ID NO: 15), or is a variant of an NLS having nuclear localization activity, the NLS comprising or consisting of the amino acid sequence of any one of SEQ ID NOs: 1 to 15.

13. The multimeric compound of any one of items 1 to 12, wherein the at least two monomers comprise a steroid acid-peptide conjugate in which the peptide does not comprise an endosomal escape motif, or protein transduction motif, or cell penetrating motif.

14. The multimeric compound of any one of items 1 to 13, wherein the at least two monomers comprise a steroid acid-peptide conjugate in which the steroid acid is conjugated at or towards the N- or C-terminus of the peptide.

15. The multimeric compound of any one of items 1 to 14, wherein the at least two monomers comprise a steroid acid-peptide conjugate in which the steroid acid is a bile acid (e.g., a primary bile acid or a secondary bile acid).

16. The multimeric compound of any one of items 1 to 15, wherein the at least two monomers comprise a steroid acid-peptide conjugate in which the steroid acid is or comprises: (a) a bile acid which is: cholic acid (CA), chenodeoxycholic acid (CDCA), deoxycholic acid (DCA), lithocholic acid (LCA), glycodeoxycholic acid (GDCA), glycocholic acid (GCA), taurocholic acid (TCA), glycodeoxycholic acid (CDCA), glycochenodeoxycholic acid (GCDCA), taurodeoxycholic acid (TDCA), glycolithocholic acid (GLCA), taurolithocholic acid (TLCA), taurohyodeoxycholic acid (THDCA), taurochenodeoxycholic acid (TCDCA), ursocholic acid (UCA), tauroursodeoxycholic acid (TUDCA), ursodeoxycholic acid (UDCA), or glycoursodeoxycholic acid (GUDCA); (b) an analog of the bile acid of (a) that: induces endocytosis; triggers ceramide accumulation on the inner leaflet of endosomes; triggers increased acid sphingomyelinase (ASM)-mediated cleavage of sphingomyelin to form ceramide; and/or has a hydrophobicity greater than that of cholic acid; (c) a bile acid or bile acid analog that is more hydrophobic than cholic acid (e.g. CDCA, DCA, LCA, TCA, TDCA, TCDCA, GCA, GDCA, or GCDCA); or (d) any combination of (a) to (c).

17. The multimeric compound of any one of item 1 to 16, wherein the multimeric compound is conjugated to a carrier molecule.

18. The multimeric compound of item 17, wherein the carrier molecule is a protein carrier (e.g., antibody or receptor ligand); polysaccharide carrier; polynucleotide carrier; polynucleotide analog carrier; polyethylene glycol carrier; lipid carrier; or other biocompatible carrier.

19. The multimeric compound of item 17 or 18, wherein the carrier molecule is a targeting molecule, and wherein the multimeric compound, and/or one of more of the monomers, is released from the carrier molecule upon (or subsequent to) binding of the carrier molecule to a specific target.

20. The multimeric compound of any one of items 17 to 19, wherein the multimeric compound, and/or one of more of the monomers, is releasably bound to the carrier molecule via a cleavable linker (e.g., enzymatically cleavable, such as cathepsin-, matrix metalloproteinase-mediated cleavage, or a valine-citrulline linker, legumain cleavage site (SEQ ID NO: 18)), photocleavable linker, a redox-sensitive linker (e.g., disulfide bond), or a pH-sensitive linker.

21. The multimeric compound of any one of items 17 to 20, wherein the carrier molecule is an antibody or receptor ligand.

22. The multimeric compound of any one of items 17 to 21, wherein the multimeric compound is the only cytotoxic or cytostatic agent releasably bound to the carrier molecule.

23. The multimeric compound of any one of items 17 to 22, wherein the carrier molecule is further bound to a cytotoxic agent or drug (e.g., antibody-drug conjugates [ADCs]), wherein the binding of the carrier molecule to the further cytotoxic agent or drug is releasable (e.g., cleavable) or non-releasable (e.g., non-cleavable).

24. The multimeric compound of any one of items 17 to 23, which is comprised in a solution at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, or 500 micromolar.

25. A steroid acid-peptide conjugate comprising a protected thiol group, wherein the stability of the protected thiol group is greater than that of a corresponding steroid acid-peptide conjugate having said thiol group unprotected.

26. The steroid acid-peptide conjugate of item 25, wherein the protected thiol group is comprised in a side of chain of an amino acid (e.g., cysteine) comprised in the peptide.

27. The steroid acid-peptide conjugate of item 25 or 26, wherein the protected thiol group is protected with a cleavable protecting group.

28. The steroid acid-peptide conjugate of item 27, wherein the protected thiol group is protected with a protecting group via a disulfide bond.

29. The steroid acid-peptide conjugate of item 25 or 26, wherein the protected thiol group is protected with a non-cleavable protecting group.

30. The steroid acid-peptide conjugate of any one of items 25 to 29, wherein (a) the steroid acid-peptide conjugate is comprised in the multimeric compound as defined in any one of items 1 to 24; (b) the peptide of the steroid acid-peptide conjugate is as defined in any one of items 8 to 13; (c) the steroid acid of the steroid acid-peptide conjugate is as defined in any one of items 14 to 16; (d) the steroid acid-peptide conjugate is conjugated to the carrier molecule as defined in any one of items 17 to 23; (e) any combination of (a) to (d).

31. A composition comprising the multimeric compound of any one of items 1 to 24, or the steroid acid-peptide conjugate of any one of items 25 to 30.

32. The composition of item 31, which is formulated within a hydrogel, liposome, or nanoparticle (e.g., lipid nanoparticle).

33. The composition of item 31 or 32, further comprising a pharmaceutically or physiologically acceptable carrier, adjuvant, and/or excipient.

34. The composition of any one of items 31 to 33, which is adapted or formulated for oral, intravenous, intranasal, intramuscular, subcutaneous, intradermal, intratumoral, intracranial, topical, intrarectal administration, or any other route of administration.

35. The composition of any one of items 31 to 34, for use in the treatment of cancer, an autoimmune disease, or any other disease or disorder ameliorated by treatment with an antiproliferative drug in a subject; or for use as a cytotoxic or cytostatic agent; or for the manufacture of a medicament for same.

36. The composition for use of item 35, in combination with immune-checkpoint inhibitor or immunosuppressive therapy.

37. The composition of any one of items 31 to 34, for use in improving the immunogenicity and/or presentation of an antigen, wherein the antigen is covalently conjugated to or admixed with the multimeric compound or the steroid acid-peptide conjugate; or for use in the manufacture of a vaccine or an immunostimulatory composition.

38. A multimeric compound comprising two monomers covalently bound to one another, each monomer comprising a bile acid-peptide conjugate, wherein the peptide comprised in the monomers comprises a nuclear localization signal (NLS).

39. The multimeric compound of claim 38, wherein the two monomers each comprise a bile acid-peptide conjugate in which the peptide comprises a cysteine residue having a thiol group protected with a cleavable protecting group.

40. The multimeric compound of claim 38 or 39, wherein the two monomers are covalently conjugated to one another via a cleavable linkage.

41. The multimeric compound of any one of claims 38 to 40, wherein the two monomers are covalently conjugated to one another via an intermolecular disulfide bond resulting from oxidation of thiol groups present in each monomer prior to multimerization.

42. The multimeric compound of any one of claims 38 to 41, wherein the two monomers each comprise the same bile acid-peptide conjugate.

43. The multimeric compound of any one of claims 38 to 42, wherein the bile acid is: cholic acid (CA), chenodeoxycholic acid (CDCA), deoxycholic acid (DCA), lithocholic acid (LCA), glycodeoxycholic acid (GDCA), glycocholic acid (GCA), taurocholic acid (TCA), glycodeoxycholic acid (CDCA), glycochenodeoxycholic acid (GCDCA), taurodeoxycholic acid (TDCA), glycolithocholic acid (GLCA), taurolithocholic acid (TLCA), taurohyodeoxycholic acid (THDCA), taurochenodeoxycholic acid (TCDCA), ursocholic acid (UCA), tauroursodeoxycholic acid (TUDCA), ursodeoxycholic acid (UDCA), or glycoursodeoxycholic acid (GUDCA).

44. The multimeric compound of any one of claims 38 to 42, wherein the bile acid is an analog of CA, CDCA, DCA, LCA, GDCA, GCA, TCA, CDCA, GCDCA, TDCA, GLCA, TLCA, THDCA, TCDCA, UCA1, TUDCA, UDCA, or GUDCA, wherein the analog: induces endocytosis; triggers ceramide accumulation on the inner leaflet of endosomes; triggers increased acid sphingomyelinase (ASM)-mediated cleavage of sphingomyelin to form ceramide; and/or has a hydrophobicity greater than that of cholic acid.

45. The multimeric compound of any one of claims 38 to 42, wherein the bile acid is or comprises: CA or CDCA.

46. The multimeric compound of any one of claims 38 to 45, wherein the NLS is a/an: SV40 NLS (SEQ ID NO: 1 or 2), GWG-SV40NLS (SEQ ID NO: 3), hnRNPA1 M9 NLS (SEQ ID NO: 4), hnRNP D NLS (SEQ ID NO: 5), hnRNP M NLS (SEQ ID NO: 6), PQBP-1 NLS (SEQ ID NO: 7), NLS2-RG Domain RPS17 (SEQ ID NO: 8), NLS1 RPS17 (SEQ ID NO: 9), NLS2 RPS17 (SEQ ID NO: 10), NLS3 RPS17 (SEQ ID NO: 11), cMyc NLS (SEQ ID NO: 12), HuR NLS (SEQ ID NO: 13), Tus NLS (SEQ ID NO: 14), or Nucleoplasmin NLS (SEQ ID NO: 15).

47. The multimeric compound of any one of claims 38 to 45, wherein the NLS is a variant of an NLS having nuclear localization activity, the NLS comprising or consisting of the amino acid sequence of any one of SEQ ID NOs: 1 to 15.

48. The multimeric compound of any one of claims 38 to 45, wherein the NLS is a/an hnRNPA1 M9 NLS (SEQ ID NO: 4), SV40 NLS (SEQ ID NO: 1 or 2) or hnRNP D NLS (SEQ ID NO: 5).

49. The multimeric compound of any one of claims 38 to 48, wherein the multimeric compound is conjugated to a biocompatible carrier molecule.

50. The multimeric compound of any one of claims 38 to 49, wherein the multimeric compound, or a monomer comprised therein, is releasably bound to the biocompatible carrier molecule via a cleavable linker.

51. The multimeric compound of claim 49 or 50, wherein the biocompatible carrier molecule is an antibody or receptor ligand.

52. The multimeric compound of any one of claims 49 to 51, wherein the biocompatible carrier molecule is further bound to a cytotoxic agent or drug.

53. The multimeric compound of any one of claims 38 to 52, wherein the bile acid comprises CA or CDCA, and the NLS is a/an hnRNPA1 M9 NLS (SEQ ID NO: 4), SV40 NLS (SEQ ID NO: 1 or 2) or hnRNP D NLS (SEQ ID NO: 5).

54. The multimeric compound of any one of claims 38 to 53, further comprising an antigen admixed therewith or covalently conjugated thereto, wherein the admixture or covalent conjugation improves the immunogenicity of the antigen.

55. The multimeric compound of any one of claims 38 to 53, which is comprised in a pharmaceutical composition at a cytotoxic or cytostatic concentration, free or bound to a biocompatible carrier molecule.

EXAMPLES

Example 1: General Materials and Methods

Animals and Ethics

Six- to eight-week-old BALB/c mice were purchased from Jackson Laboratories (Bar Harbor, ME, USA) whereas C57BL/6 mice of similar age were purchased from Charles River (Montreal, QC, Canada). Littermate mice were interbred and housed in a pathogen-free environment at the animal facility of the Institute for Research in Immunology and Cancer (IRIC). Animal protocols were approved by the Animal Care Committee of Université de Montréal.

Cell Lines and Reagents

All cell culture media and reagents were purchased from Wisent Bioproducts (St-Bruno, QC, Canada) unless otherwise indicated. All flow cytometry antibodies were purchased from BD Biosciences (San Jose, CA, USA) unless otherwise indicated. The PD-1 antibody (clone RMP1-14) used in in vivo studies was purchased from BioXCell (West Lebanon, NH, USA).

Generation of the Steroid Acid-NLS Moieties

Bile acid-NLS moieties were synthesized similar to the synthesis of cholic acid-NLS (ChAcNLS) as previously described in Beaudoin et al., 2016, in U.S. Pat. No. 11,291, 717, or in WO/2022/232945, unless otherwise specified. For example, for CA-C-SV40NLS, cholic acid was conjugated to the free amino group of the N-terminal cysteine residue of a 13-mer peptide (CGYGPKKKRKVGG; SEQ ID NO: 1) that comprises a nuclear localization signal from SV40 large T-antigen (SEQ ID NO: 2) flanked by linker amino acids.

Generation of Bone Marrow Derived DCs

Mouse bone marrow derived DCs (BMDCs) were generated by flushing the whole marrow from mouse femurs using RPMI™ 1640 supplemented with 10% fetal bovine serum (FBS), 50 U/mL Penicillin-Streptomycin, 2 mM L-glutamine, 10 mM HEPES, 1% MEM Non-essential Amino Acids, 1 mM Sodium Pyruvate, 0.5 mM β-mercaptoethanol. Following red blood cell lysis, cells were then cultured in media supplemented with 50 ng/ml murine recombinant GM-CSF. The media was changed on days 2, 4, 6 and 8. On day 9, the media was replaced to include recombinant murine GM-CSF and LPS from *Escherichia coli* 0111 (1 ng/mL) to stimulate DC maturation. Mature DCs were assessed by flow cytometry for their surface expression of CD3, CD19, NK1.1, CD11c, CD80, CD86, and I-A$^b$.

Tumor Model

Female C57BL/6 mice (n=10/group) received a SC injection of 5×10$^5$ EL4 cells at Day 0. Five days later (appearance of palpable tumors ~40-60 mm$^3$), mice were SC-injected with PBS, CA-C-SV40, anti-PD-1, or anti-CTLA4, alone or in combination (200 μg/injection; total of 4 injections; i.p. 3 times per week for two consecutive weeks). For all depletion studies, antibodies were injected via the intraperitoneal route at days 0, 3 and 6 at a concentration of 200 μg/injection. Tumor size and animal survival for all of the above listed in vivo studies was followed thereafter using a digital caliber until reaching endpoints (ulceration or a tumor volume ≥1000 mm$^3$).

Apoptosis Analysis

Apoptosis analysis was conducted by flow-cytometry. Briefly, target cells were first treated then washed. Treated cells were then re-suspended in Annexin-V staining buffer prior to staining with Annexin-V and propidium iodine (PI). Fifteen minutes later, cells were washed prior to analysis using BD FACS™ Diva on CANTOII™.

Assessment of Endosomal Escape

Endosomal leakage was assessed using two different approaches; the first strategy utilizes the FRET sensor CCF4-AM, a β-lactamase substrate. Briefly, EL4 cells were treated with 1 μM CCF4-AM for 1 h followed by the addition of 10 mg/ml of β-lactamase in the presence or absence of CA-C-SV40 (at concentration of 190 μM) for 3 h at 37° ° C. The cells were then washed, and fresh media added for an incubation period of 16 h at 37° C. The loss of FRET signal between the coumarin (donor) and fluorescein (acceptor) fluorophores was quantified by flow cytometry. For the apoptosis assay, 10$^5$ EL4 cells were first supplemented with 10 mg/ml of exogenous rCyt-C for 6 h at 37° C. in the presence or absence of CA-C-SV40 (at a concentration of 190 μM). Once the incubation period completed, the cells were washed with ice cold PBS, then stained for Annexin-V according to manufacturer's instructions prior to analysis using BD FACS Diva on CANTOII.

Assessment of Immunogenic Cell Death

To obtain conditioned media (CM), 5×10$^5$ EL4 cells were seeded in 24-well plates in complete RPMI for 24 hours followed by treatment with CA-C-SV40 at the indicated concentrations for the indicated time points. Western blot for HMGB1: HMGB1 protein from cell free CM were resolved by SDS-PAGE and transferred to Immun-Blot-PVDF membranes (BioRad) for immunoblotting. HMGB1 expression was detected using HMGB1 specific primary antibody (ab18265, 1:1000) and corresponding HRP-conjugated goat anti-Rabbit secondary antibody (ab205718, 1:10,000). HMGB1 expression was visualized by chemiluminescence detection (ChemiDoc™; BioRad). For ATP detection, concentrations of ATP in the CM were measured with the ENLITEN-ATP kit (Promega). Briefly, 100 μL of CM was transferred to 96-well opaque plates. Then 100 μL of reconstituted rLuciferase/Luciferin reagent was added to each well followed by measurement of luciferase using a luminescence microplate reader (Fusion™ V.3.0). Calreticulin exposure: treated cells were harvested and cell surface calreticulin exposure was measured by flow cytometry. The calreticulin primary antibody (ab2907) was added to cells for 20 mins at 4° C., followed by washing with flow cytometry buffer (PBS+2% FBS), then stained with goat anti-rabbit secondary antibody (Alexa647™ Life Technologies) for an additional 20 mins at 4° C. Samples were washed twice and resuspend in flow cytometry buffer containing 0.2 μg/mL DAPI (Invitrogen) and acquired on a CytoFLEX™ 30 (Beckman Coulter). Data were analyzed with CytExpert™ software.

Preparation of Steroid Acid-Peptide Conjugate Dimers 50 mg of CDCA-C-SV40 monomers (or other steroid acid-peptide monomers) were resuspended in 200-500 μL of DMSO. 10 eq of N,N-Diisopropylethylamine (DIPEA) was added to the mixture and incubated in a thermomixer at 37° C. with agitation (1000 rpm) overnight, enabling dimerization of the monomers via their N-terminal cysteine thiol groups to produce (CDCA-C-SV40)$_2$ or other dimers. The samples were then analyzed by UPLC-MS to evaluate dimer formation efficiency. Cell toxicity was evaluated via a Cell Toxicity assay (PrestoBlue™).

For some experiments, a GMP-grade of (CDCA-C-SV40)$_2$ was prepared and used. Briefly, (CDCA-C-SV40)$_2$ was prepared via Fmoc (Fluorenylmethyloxycarbonyl protecting group) solid phase peptide synthesis with PIP (Piperidine) being used as the reagent for Fmoc removal. DIC (N,N'-Diisopropylcarbodiimide) and HOBt (1-Hydroxybenzotriazole) were used as coupling reagents. The fully protected sequence was obtained by individual coupling based on the sequence of this product: NH$_2$-Cys(Trt)-Gly-Tyr(tBu)-Gly-Pro-Lys(Boc)-Lys(Boc)-Lys(Boc)-Arg(Pbf)-Lys(Boc)-Val-Gly-Gly-Resin. DIEA (N,N-Diisopropylethylamine) and HBTU (2-(1H-benzotriazol-1-yl)-1,1,3,3-tetramethyluronium hexafluorophosphate) were used as coupling reagents, and CDCA was attached to obtain the fully resin-protected sequence: CDCA-Cys(Trt)-Gly-Tyr(tBu)-Gly-Pro-Lys(Boc)-Lys(Boc)-Lys(Boc)-Arg(Pbf)-Lys(Boc)-Val-Gly-Gly-Resin. The compound was then converted to its final form through decomposition, primary purification and dimerization, secondary purification, salt conversation and refining, and lyophilization.

Preparation of Drug-[Steroid Acid-Peptide Dimer] Conjugates

Figure 16C:
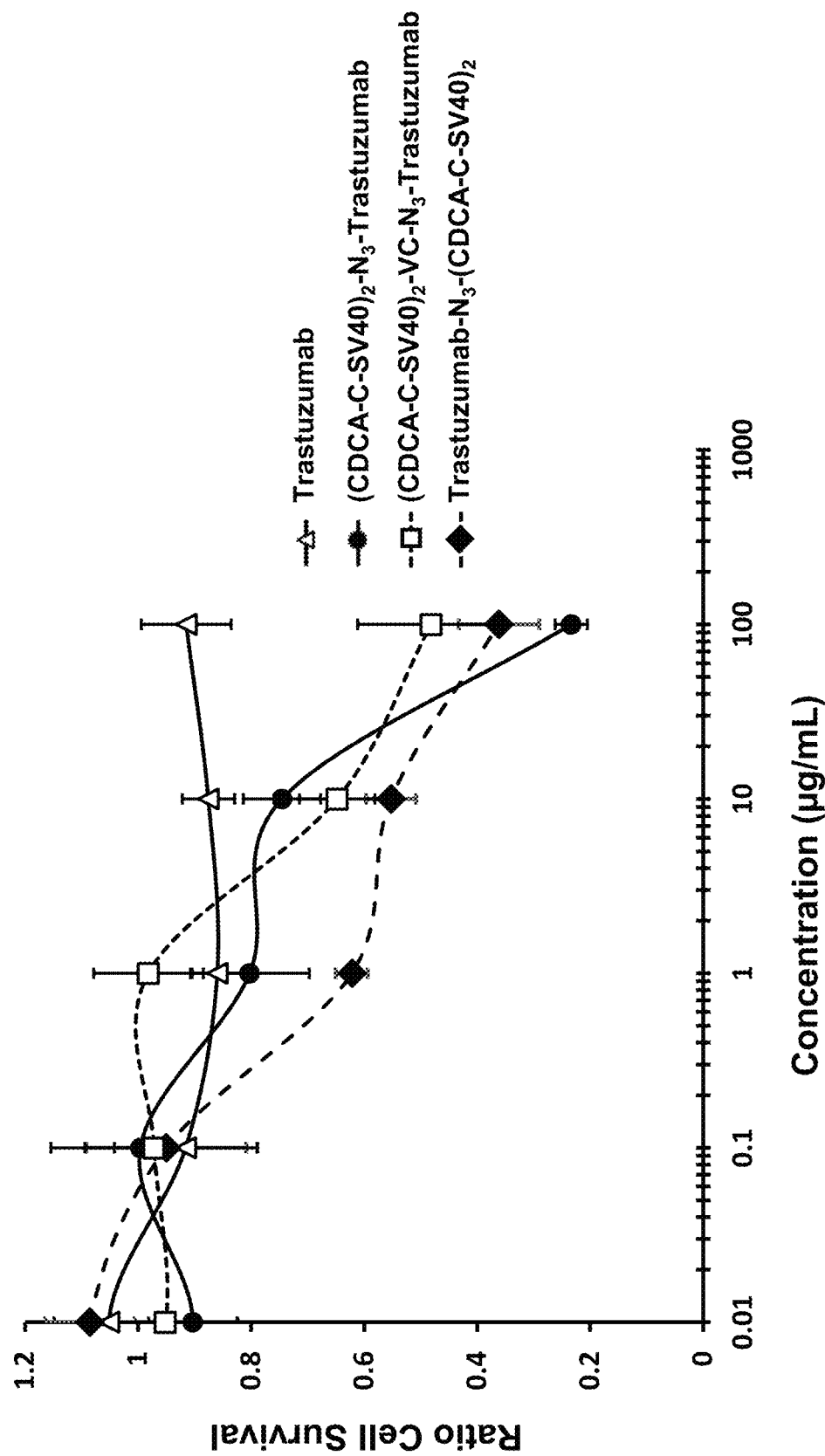

A solution of either the antibody Trastuzumab (Herceptin™), or the antibody-drug conjugate thereof Trastuzumab emtansine (T-DM1), was reacted with the bifunctional linker NHS-DBCO at the desired ratios. The DBCO/antibody ratio was determined by UV-VIS absorbance spectrometry, adjusting calculations accordingly. The solution was then left to stand under stirring and in the dark for about 1 hour. The reaction was then completed by adding 50 µL per mL of a IM solution of Tris base at pH 8, and leaving to stand at room temperature for 5 minutes. The resulting DBCO-containing Trastuzumab and T-DM1 conjugates were then reacted with a modified version of (CDCA-C-SV40)$_2$ which is a dimer of two monomers, each monomer containing a N-terminal 6-azido-L-lysine residue ("N$_3$"; for click chemistry conjugation with DBCO) and a protease-cleavable valine-citrulline linker: N$_3$-Val-Cit-(CDCA-C-SV40). The monomers were dimerized via the thiol groups of the underlined cysteine residue of each monomer, to produce the dimer: [N$_3$-Val-Cit-(CDCA-C-SV40)$_2$]. The DBCO moiety-activated antibodies were reacted with a 50× molar excess of the dimer [N$_3$-Val-Cit-(CDCA-C-SV40)$_2$] for 1 hour in the dark with stirring to produce the antibody conjugates: "Trastuzumab-N$_3$-VC-(CDCA-C-SV40)$_2$" (FIG. 16A) and "T-DM1-N$_3$-(CDCA-C-SV40)$_2$" (FIG. 16B) Also prepared were the antibody conjugates with different linkage strategies: an N-terminal 6-azido-L-lysine residue lacking a protease-cleavable valine-citrulline linker to produce "Trastuzumab-N$_3$-(CDCA-C-SV40)$_2$" (FIG. 16C); a C-terminal 6-azido-L-lysine residue lacking a protease-cleavable valine-citrulline linker to produce "(CDCA-C-SV40)$_2$-N$_3$-Trastuzumab" (FIG. 16C); and a C-terminal 6-azido-L-lysine residue containing a protease-cleavable valine-citrulline linker to produce "(CDCA-C-SV40)$_2$-VC-N$_3$-Trastuzumab" (FIG. 16C). The conjugates were then purified by filtration through Centricon™ Centrifugal Filters according to the molecular weight of the proteins. Finally, the antibody conjugates were harvested, separated on an SDS-PAGE gel, and dosed for their use in cytotoxicity assays.

Drug Conjugates Cell Cytotoxicity Assay

In a T75 flask of confluent JIMT-1 cells (at least 75%), the culture medium was removed, and 2 mL of trypsin was then added and incubated at 37° C. for about 5 minutes or until the cells detached. The trypsin was inactivated by adding 10 mL of culture medium, the cells were centrifuged at 950 rpm for 5 minutes at 4° C., viable cells were visualized with trypan blue and counted using a hematocytometer. Cells were then plated in a 96-well plate at 5000 cells/well and incubated at 37° C. for 24 hours. Trastuzumab-(CDCA-C-SV40)$_2$ or T-DM1-(CDCA-C-SV40)$_2$ was then added to the cells and incubated for 72 hours at 37° C. Supernatants were then aspirated and cells were treated with a cell viability reagent (100 µL of 10% PrestoBlue™) and incubated for 15 or 45 minutes at 37° C. Fluorescence (excitation: 535-560 nm, emission: 590-615 nm) was measured. The cells were further incubated for another 30 minutes, and a second fluorescence reading was taken.

RNA Extraction and Sequencing

Briefly, total RNA was isolated from 10$^6$ cells for each group using RNeasy® mini kit (QIAGEN) according to manufacturer's instructions. Library preparation and sequencing was performed at the Institute for Research in Immunology and Cancer (IRIC)'s Genomics Platform Bioinformatics Analysis All Fastq files were aligned to GRCm38 (mouse genome Ensembl release 102) with STAR (v2.7). Raw reads mapping to genomic features (summarized per gene) were extracted with featureCounts (strand specific option). Expression matrices were filtered, genes with very low counts were removed and protein coding genes were kept for further analyses. Both (CDCA-C-SV40)$_2$- and CA-C-SV40-treated cells were contrasted to DMSO controls with DESeq2 to generate a ranked list of differentially expressed genes based on the log 2 fold change. Gene set enrichment on either ranked lists of genes, or a number of significantly up- or down-unregulated genes perturbed by (CDCA-C-SV40)$_2$ or CA-C-SV40 compared to controls were performed using the Reactome collection of pathways. If not mentioned in the text, significance threshold is set to 5% after p-value adjustment with the Benjamini-Hochberg method to control for false positives among differentially expressed genes (DEGs). All custom scripts including prediction of putative targets were written in R programming and statistical language. Data visualization was made with ggplot2, enrichplot, Upset plots and Pheatmap R functions.

In Vivo B16F10 Tumor Model and Intranasal Treatment

Six- to ten-week-old female C57BL/6 mice were purchased from The Jackson Laboratory (Bar Harbor, ME, USA). The mice were housed and maintained in accordance with the guidelines approved by the Animal Care Committee of Université de Montréal in a pathogen-free environment at the animal facility of the Institute for Research in Immunology and Cancer (IRIC). Animal protocols were approved by the Animal Care Committee of Université de Montréal.

The tumor cell line B16F10 were cultured in DMEM supplemented with 2 g/L Glucose, 10% FBS, and 50 U/mL Penicillin-Streptomycin.

Mice received (0.25M/injection) of B16F10 tumor cells intravenously. Three days later, (CDCA-C-SV40)$_2$ was intranasally administered at 3 mg/kg for a total of 6 injections over 2 weeks. The anti-PD-1 antibody was administered at 200 µg/injection delivered via the intraperitoneal (IP) route 3 times per week for two consecutive weeks (total of 6 injections). All vaccinated animals were sacrificed by perfusion 3 days following the final injection. Macroscopic tumor nodules were counted.

In Vivo B16F10 Tumor Model and Intratumoral Treatment

Six- to ten-week-old female C57BL/6 mice were purchased from The Jackson Laboratory (Bar Harbor, ME, USA). The mice were housed and maintained in accordance with the guidelines approved by the Animal Care Committee of Université de Montréal in a pathogen-free environment at the animal facility of the Institute for Research in Immunology and Cancer (IRIC). Animal protocols were approved by the Animal Care Committee of Université de Montréal.

The tumor cell line B16F10 were cultured in DMEM supplemented with 2 g/L Glucose, 10% FBS, and 50 U/mL Penicillin-Streptomycin.

Mice were first subcutaneously (SC) implanted with the B16 tumor cell line (0.5M/injection). Three to four days later, palpable tumors were intratumorally (IT) injected twice a week with (CDCA-C-SV40)$_2$ (16 mg/kg) for a total of 6 injections. Anti-PD-1 and anti-LAG3 were used at 200 μg/injection delivered via the intraperitoneal (IP) route 2 times per week for three consecutive weeks (total of 6 injections). All vaccinated animals were monitored for up to 6 weeks. Tumor size and animal survival for all of the above listed in vivo studies were followed thereafter using a digital caliber until reaching endpoints (ulceration, loss in weight of >20%, or a tumor volume ≥1000 mm$^3$).

Statistical Analysis p-values were calculated using the one-way analysis of variance (ANOVA). Results are represented as average mean with S.D. error bars, and statistical significance is represented with asterisks: * P<0.05,  P<0.01, * P<0.001.

Example 2: Steroid Acid-Peptide Conjugates Induce Cell Death

As shown in FIG. 1A, cholic acid (CA) conjugated to the SV40 NLS (CA-C-SV40) triggers cell death through apoptosis of the T-cell lymphoma line EL4 as well as colon (CT-26) and breast cancer (4T-1) cells to a similar extent, as measured by Annexin V staining. We next conducted a cell death curve analysis by flow cytometry and identified the EC$_{50}$ of CA-C-SV40 on the EL4 T-cell lymphoma to be 95.94 μM (FIG. 1B). Interestingly, CA and SV40 NLS separately did not exhibit any cytotoxic activity at any of the concentrations tested. Furthermore, CA-C-SV40 was shown to induce apoptosis in normal or healthy cells, such as in mesenchymal stem cells (MSCs), macrophages, and bone marrow-derived dendritic cells (DCs) (FIG. 1C).

To further uncover the mechanism of cell death, we next investigated whether CA-C-SV40-triggered apoptosis is strictly occurring in the absence of necrosis. To do so, a co-staining experiment was conducted using propidium iodine (PI) and Annexin-V at different time points. As shown in FIG. 2A, apoptosis started occurring as of 1 h post-CA-C-SV40 treatment with complete death obtained after 8 h. Nevertheless, no necrotic cells (PI+/Annexin V−) were detected during this staining strategy suggesting absence of membrane damages (necrosis). Since a large number of anti-cancer molecules can trigger cell death via release or de novo production of reactive oxygen species (ROS), we next stained the EL4 lymphoma cells treated with CA-C-SV40 at the EC$_{50}$ dose with MitoSOX™. Flow cytometry analysis of MitoSOX signal shows a time-dependent ROS production with most cells staining positive 8 h post-treatment (FIG. 2B). This observation led us to test whether treatment with MitoTempo™ (blocking mitochondria-specific ROS) or N-acetylcysteine (NAC, a building block for GSH) rescue from CA-C-SV40-triggered cell death. Interestingly, only NAC completely blocked apoptosis when the EC$_{50}$ dose was used with an incomplete but significant blockade observed at higher doses (IC$_{100}$-FIG. 2C).

These results demonstrate that a bile acid-NLS conjugate, CA-C-SV40, has cytotoxic activity against various cancer cell lines, which may be mediated through release of intracellular ROS and apoptosis.

Figure 3B:
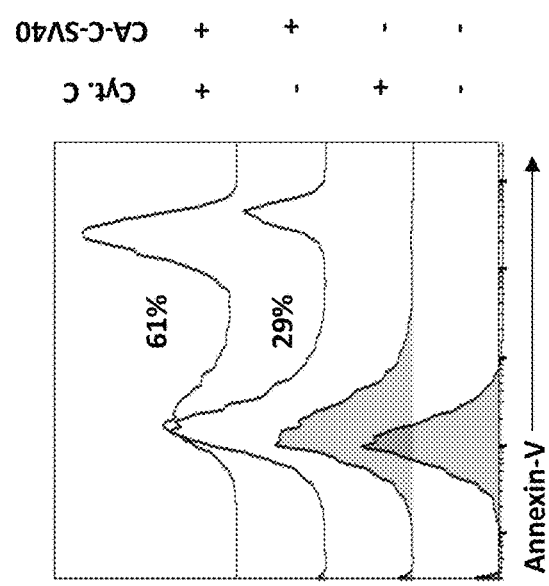

Example 3: Steroid Acid-Peptide Conjugates Promote Endosomal Escape and Cargo Release in the Cytoplasm of Target Cells Cytochrome C is a protein that is normally entrapped in the mitochondria but can be released upon intrinsic signaling known to trigger apoptosis. An experiment was designed where recombinant cytochrome C was added to EL4 cells either alone or in combination with CA-C-SV40 (47 μM) (FIG. 3A). Interestingly, addition of cytochrome C alone did not trigger cell death, whereas its combination with a weak dose of CA-C-SV40 increased cell death by two-fold (29% to 61%-FIG. 3B).

FIG. 3C shows a schematic representation depicting a fluorescence resonance energy transfer (FRET) experiment used to demonstrate that CA-C-SV40 induces endosomal escape. CCF4 is a FRET substrate that consists of a cephalosporin core linking 7-hydroxycoumarin to fluorescein. CCF4-AM is an esterified form of CCF4 that enables it to readily enter cells and, upon entry, cleavage by endogenous cytoplasmic esterases rapidly converts CCF4-AM into its negatively charged form, CCF4, which is retained in the cytosol. Cleavage of CCF4 by β-lactamase results in a loss of FRET signal and switching of its emission spectrum. EL4 cells pre-loaded with CCF4 can then be treated with β-lactamase, which is internalized into endosomes. Disruption of endosomal membranes causes a release of β-lactamase into the cytosol, where it can then cleave CCF4. FIG. 3D shows a representative flow cytometry analysis revealing a change in CCF4-emitted signal when EL4 cells were co-incubated with β-lactamase and CA-C-SV40, as compared to cell incubated with β-lactamase alone.

These data clearly suggest that a bile acid-NLS conjugate, CA-C-SV40, disrupts endosomal membranes, which not only leads to cargo release, but may also perturb the entire vesicular transport system. In addition, it may explain the increase in intracellular ROS levels as it can damage endosomes/vesicles responsible for intracellular ROS transport.

Example 4: Steroid Acid-Peptide Conjugates Delay Tumor Growth In Vivo

The apoptosis observations obtained in vitro prompted us to explore whether CA-C-SV40 administration to mice with pre-established tumors can trigger a therapeutic effect. First, CA-C-SV40 was administered alone using three different doses (47 μM, 95 μM, and 190 μM) every 48 h following the appearance of palpable tumors (EL4) (FIG. 4A) for a total of 5 injections. As shown in FIG. 4B, the highest tested dose significantly delayed tumor growth resulting in a 60% survival at day 40 (FIG. 4C). To further improve this response, we next combined the highest tested CA-C-SV40 dose (delivered daily instead of every 48 h) with the immune-checkpoint inhibitors (ICIs) anti-PD-1 or anti-CTLA4 (FIG. 4D). Although animals treated with CA-C-SV40 alone exhibited significant delays in tumor growth, combining CA-C-SV40 with ICIs significantly enhanced the antitumoral response (FIG. 4E and FIG. 4F).

Figure 9G:
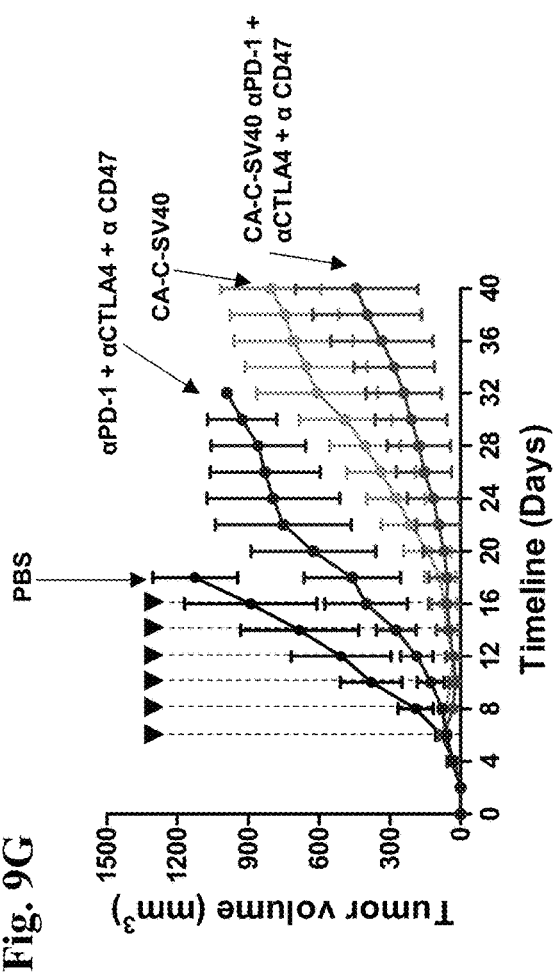
Figure 9H:
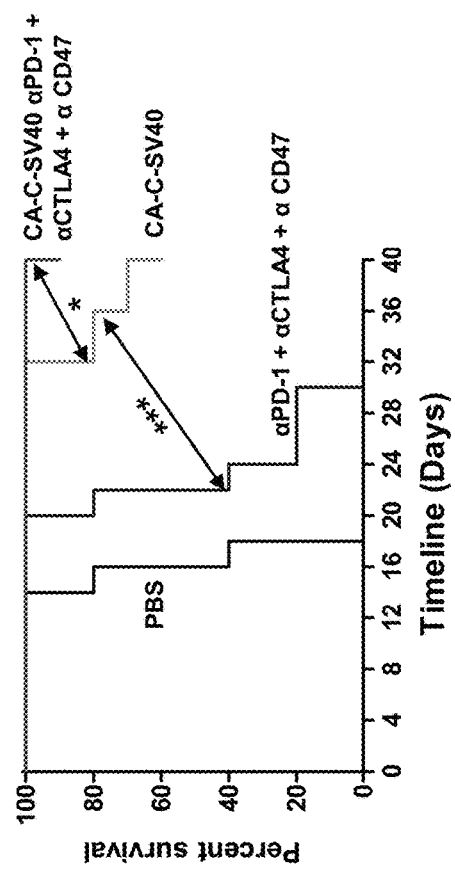
FIG. 9H shows the Kaplan-Meier survival curve for the experiment in FIG. 9G. n=5/group with *P<0.05, and *** P<0.001. For panels B, C, E, F, G and H, n=10/group.

FIGS. 9A to 9G show the results of a second study of the antitumoral effect of CA-C-SV40 on EL4 lymphoma in vivo with different immune checkpoint inhibitors, anti-PD-1, anti-CTLA4, or anti-CD47. For the study in FIGS. 9A to 9C, CA-C-SV40 was administered once every 48 h for a total of 6 injections. Tumor growth was strikingly reduced in mice injected with CA-C-SV40, compared to controls (FIG. 9B). Inhibition of tumor growth was enhanced in the presence of either anti-PD-1, anti-CTLA4, or anti-CD47, with anti-CD47 showing the highest effect. Effect on tumor growth correlated with increased survival, as shown in mice injected with CA-C-SV40 in the presence or absence of immune checkpoint inhibitors (FIG. 9C). Similar findings were observed in the study of FIGS. 9D to 9E, whereby CA-C-SV40 was delivered once every 24 h for a total of 6 injections. CA-C-SV40, in the presence or absence of immune checkpoint inhibitors, delayed tumor growth and increased survival of mice treated with EL4 lymphoma. Furthermore, a combination of all the immune checkpoint inhibitors with CA-C-SV40 also proved to be effective in inhibiting tumor growth and increasing survival of mice treated with EL4 lymphoma (FIGS. 9G and 9H).

CA-C-SV40-mediated antitumor effects was shown to involve endogenous immunity, particularly T cell-mediated immunity. Mice were treated with EL4 lymphoma cells and depleted of CD4 T cells, CD8 T cells, or NK cells via antibody depletion. Mice were then treated with CA-C-SV40, as previously done, and the effect on tumor growth and survival was assessed (FIG. 10A). As shown in FIG. 10B, the inhibitory effect on tumor growth and survival by CA-C-SV40 was diminished in mice depleted of CD8 T cells, and even more so in mice depleted of CD4 T cells (FIGS. 10B and 10C). Nevertheless, mice depleted in NK cells maintained the effect of CA-C-SV40 on tumor growth and survival (FIGS. 10B and 10C).

Next, the mechanism of CA-C-SV40-mediated cytotoxicity in EL4 lymphoma cells was assessed. CA-C-SV40-treated EL4 cells were shown to increase expression of intracellular High-mobility Group Box 1 (HMGB1) protein, which is a known tumor suppressor protein (Wang et al., 2020), as shown by Western Blot of EL4 cell lysates (FIGS. 10D and 10E). As shown in FIGS. 10F and 10G, treatment of EL4 cells with CA-C-SV40 decreases intracellular ATP levels and increases calreticulin levels over time, indicating an increase in tumor cell death, and more particularly immunogenic cell death.

These data suggest that steroid acid-peptide conjugates are suitable and potent candidates for anticancer therapies.

Example 5: Engineering Potent Steroid Acid-Peptide Conjugates with Enhanced Cytotoxic and Anti-Tumoral Properties The data obtained so far clearly demonstrate the potential of using CA-C-SV40 as a cytotoxic or an anti-cancer molecule. In an attempt to further enhance the pro-apoptotic potency of CA-C-SV40, a series of different bile acid-NLS conjugates were engineered and tested for their cytotoxic ability (FIG. 5 and FIG. 6).

Figure 5:
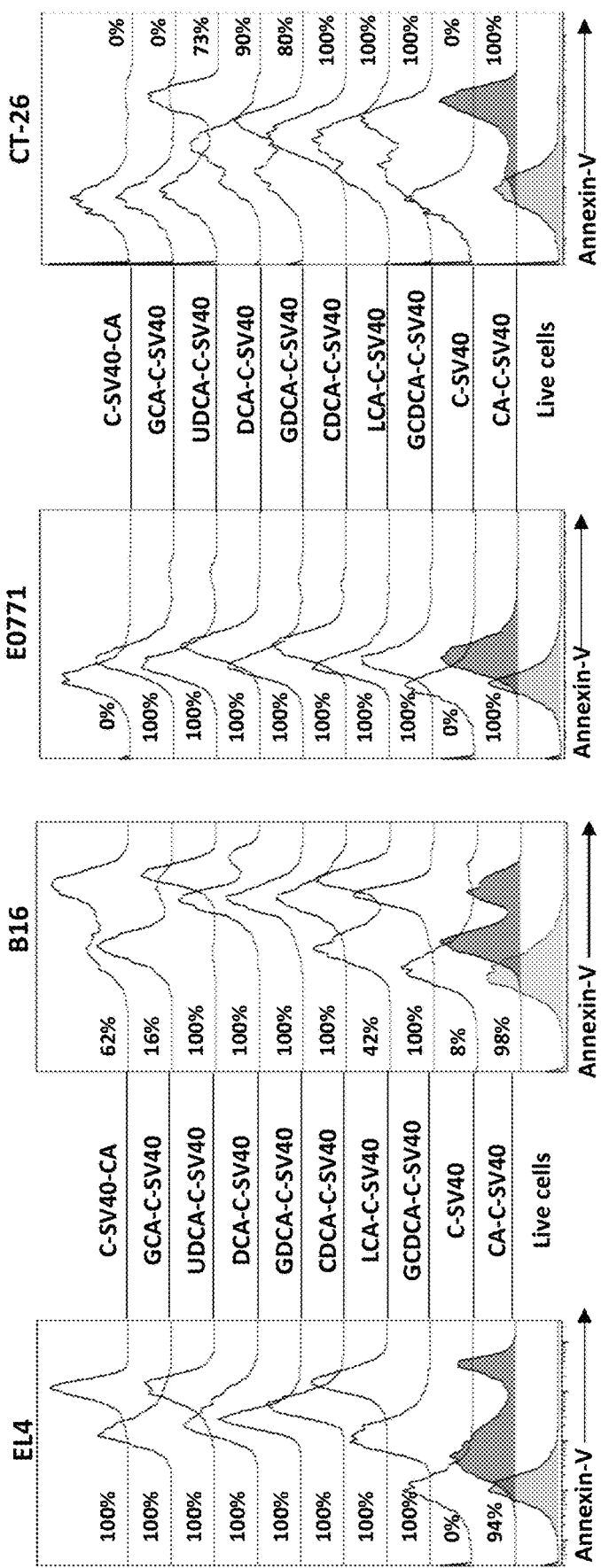
FIG. 5 shows the cytotoxic effect of different bile acid-SV40 conjugates on different cancer cell lines. Annexin-V staining percentage after treatment with different bile acid-SV40 conjugates (190 μM) is shown relative to live cancer cells (i.e., PBS treated cancer cells) by flow cytometry. Cancer cell lines tested were EL4 lymphoma, B16 melanoma, E0771 breast cancer, CT-26 colon carcinoma, 4T1 breast cancer, MBA-MD-468 triple-negative breast cancer, human H460 lung cancer, and human A549 lung cancer. Bile acids conjugated to SV40 NLS were: N-term cholic acid (CA) (i.e., CA-C-SV40); C-term cholic acid (CA) (i.e., SV40-CA); glycodeoxycholic acid (GDCA); glycochenodeoxycholic acid (GCDCA); chenodeoxycholic acid (CDCA); ursodeoxycholic acid (UDCA); deoxycholic acid (DCA); glycocholic acid (GCA); and lithocholic acid (LCA). SV40 alone was also tested as a negative control.
Figure 5:
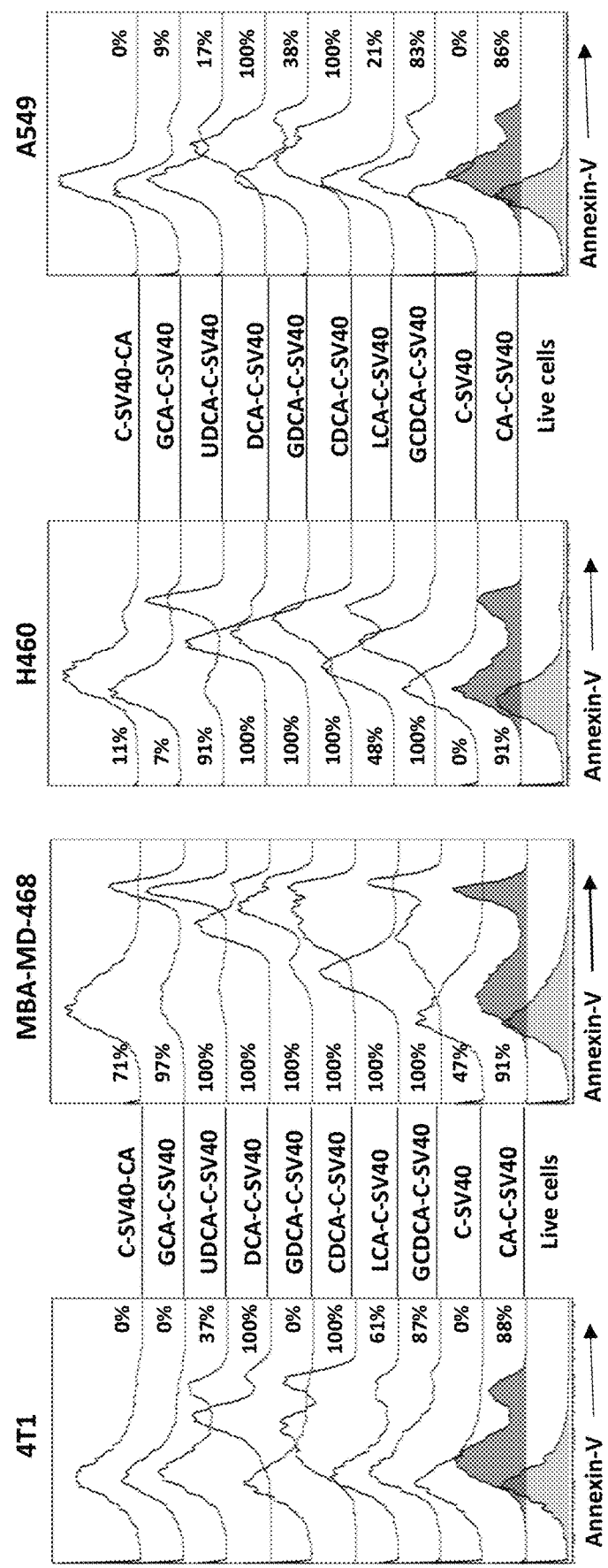

First, different bile acid-SV40 NLS conjugates were produced by changing the bile acid moiety of CA-C-SV40 (FIG. 5). Enhanced cell death was observed with various bile acid-SV40 conjugates when tested on EL4 lymphoma, B16 melanoma, E0771 breast cancer, CT-26 colon cancer, 4T1 breast cancer, MBA-MD-468 breast cancer, H460 lung cancer, as well as A549 lung cancer cells. Furthermore, in some cases, CA conjugated C-terminus (C-SV40-CA) of SV40 NLS exhibited similar cytotoxic ability in comparison to N-terminus conjugated CA (CA-C-SV40).

Figure 6:
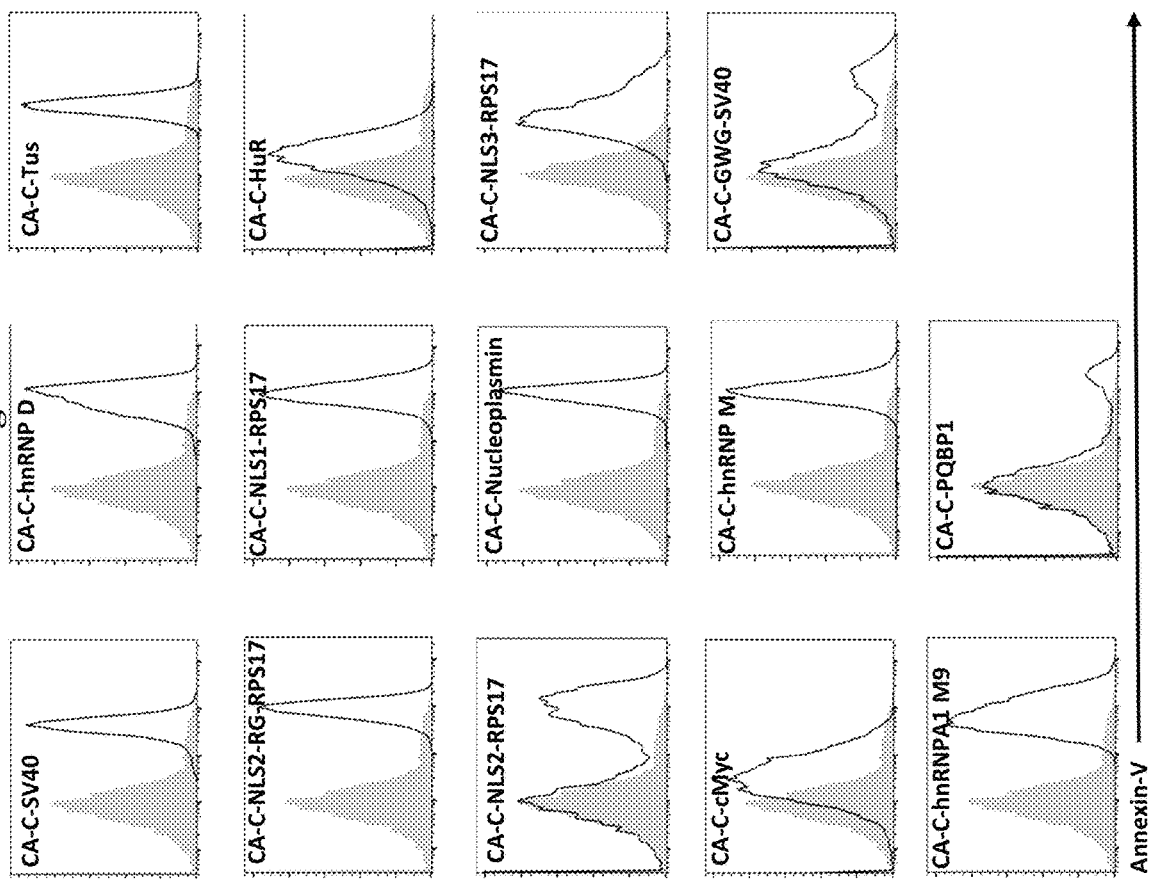
FIG. 6 shows the cytotoxic effect of different Cholic acid-NLS conjugates on cancer cells. Annexin-V staining percentage after treatment with different Cholic acid-NLS conjugates (190 μM) is shown relative to live EL4 lymphoma cells (i.e., PBS treated cancer cells) by flow cytometry. NLSs conjugated to cholic acid (CA) were: SV40 NLS; hnRNP D NLS; Tus NLS; NLS2-RG-RPS17 NLS; NLS1-RPS17; HuR; NLS2-RPS17; Nucleoplasmin; NLS3-RPS17; cMyc; hnRNP M NLS; GWG-SV40 NLS; hnRNPA1 M9 NLS; and PQBP-1 NLS.

Second, a similar engineering approach was conducted by testing other NLSs in combination with cholic acid (FIG. 6). The majority of CA-NLS conjugates tested exhibited cytotoxic activity. The cytotoxicity of CA-C-SV40 was notably higher than that of CA-C-GWG-SV40, with the only difference between the structures of the two molecules being the insertion of a GWG motif in the latter, which has been reported to facilitate endosome escape via possible insertion/retention in the endosomal membrane.

These data demonstrate the potent cytotoxic and anticancer activity of various bile acid-NLS conjugates, and their potential use as therapeutics.

Example 6: Different Steroid Acid-NLS Conjugates Delays Tumor Growth In Vivo

Figure 7A:
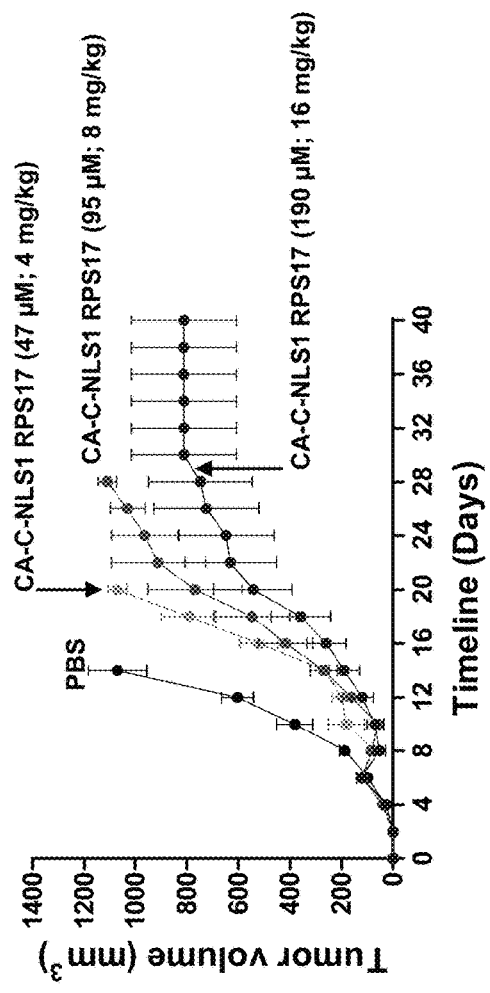
FIGS. 7A and 7B show the antitumoral effect of CA-C-NLS1 RPS17 on EL4 lymphoma in vivo.
Figure 7B:
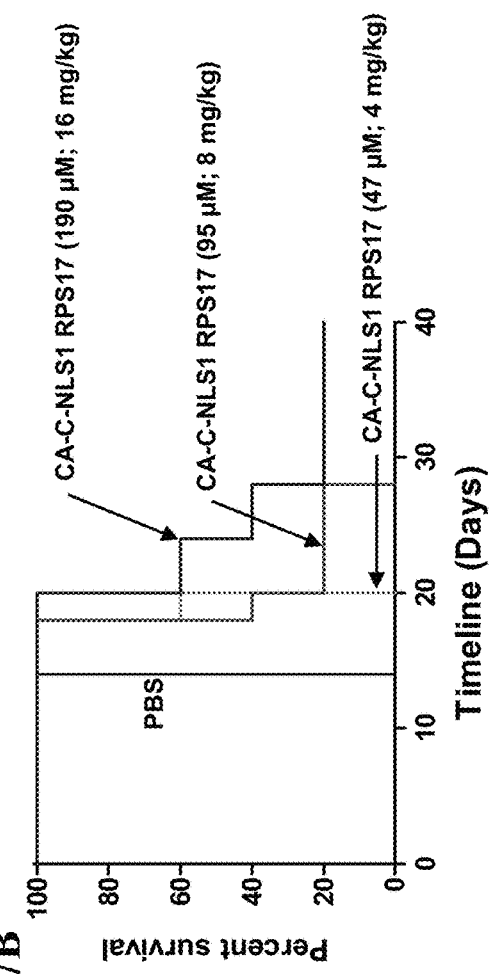

CA-C-NLS1 RPS17 (FIGS. 7A and 7B) and CA-C-NLS3 RPS17 (FIGS. 8A and 8B) were delivered alone using three different doses (47 µM, 95 µM, and 190 µM) every 48 h following the appearance of palpable tumors (EL4) for a total of 5 injections. As shown in FIGS. 7A and 8A, the highest tested dose significantly delayed tumor growth resulting in a 20% survival at day 40 (FIGS. 7B and 8B).

These data demonstrate that different bile acid-NLS conjugates have cytotoxic and anticancer activities in vivo.

Example 7: Dimerized Steroid Acid-Peptide Conjugates Exhibit Greater Stability than their Monomeric Counterparts A plurality of steroid acid-peptide conjugate monomers displayed significant cytotoxic activity towards different tumor cell lines in the screening assays shown in Example 5. In particular, the CDCA-C-SV40 monomer displayed consistent potent (100%) cytotoxic activity against all eight tumor cell lines tested (FIG. 5) and was selected for further characterization. GMP synthesis of the CDCA-C-SV40 monomer yielded a white powder and the results of initial stability testing is summarized below:

| | Purity | Impurity A (Thiol oxidation) | Impurity B (Intermolecular disulfide bond) |
|---|---|---|---|
| Day 0 | 94.53% | 1.24% | 2.12% |
| Day 5 (5° C.) | 91.38% | 2.66% | 2.45% |
| Day 5 (25° C.) | 84.52% | 6.14% | 4.75% |

As shown above, two main impurities were detected by HPLC relating to the reactivity of the free thiol group of the CDCA-C-SV40 monomer, namely impurities resulting from oxidation of the thiol group (Impurity A) and the formation an intermolecular disulfide bond via the thiol groups of two CDCA-C-SV40 monomers, producing a (CDCA-C-SV40)$_2$ dimer (Impurity B).

To attempt to improve stability, the synthesis protocol of CDCA-C-SV40 was modified to produce the conjugate directly in its dimerized form (Impurity B). Interestingly, stability testing on the (CDCA-C-SV40)$_2$ dimer revealed that the conjugate exhibited markedly higher stability than its corresponding monomer. The (CDCA-C-SV40)$_2$ dimer was found to be stable after at least 3 months at 5° C., with total impurities starting at 1.6% at Day 0 and remaining at this level at least at 3 months. At 25° C., total impurities rose only slightly from 1.6% at Day 0 to 2.1% after 3 months. At 40° C., total impurities rose from 1.6% at Day 0 to 1.7% after 5 days, 2.4% after 10 days, and to 3.7% after 30 days.

Figure 18A:
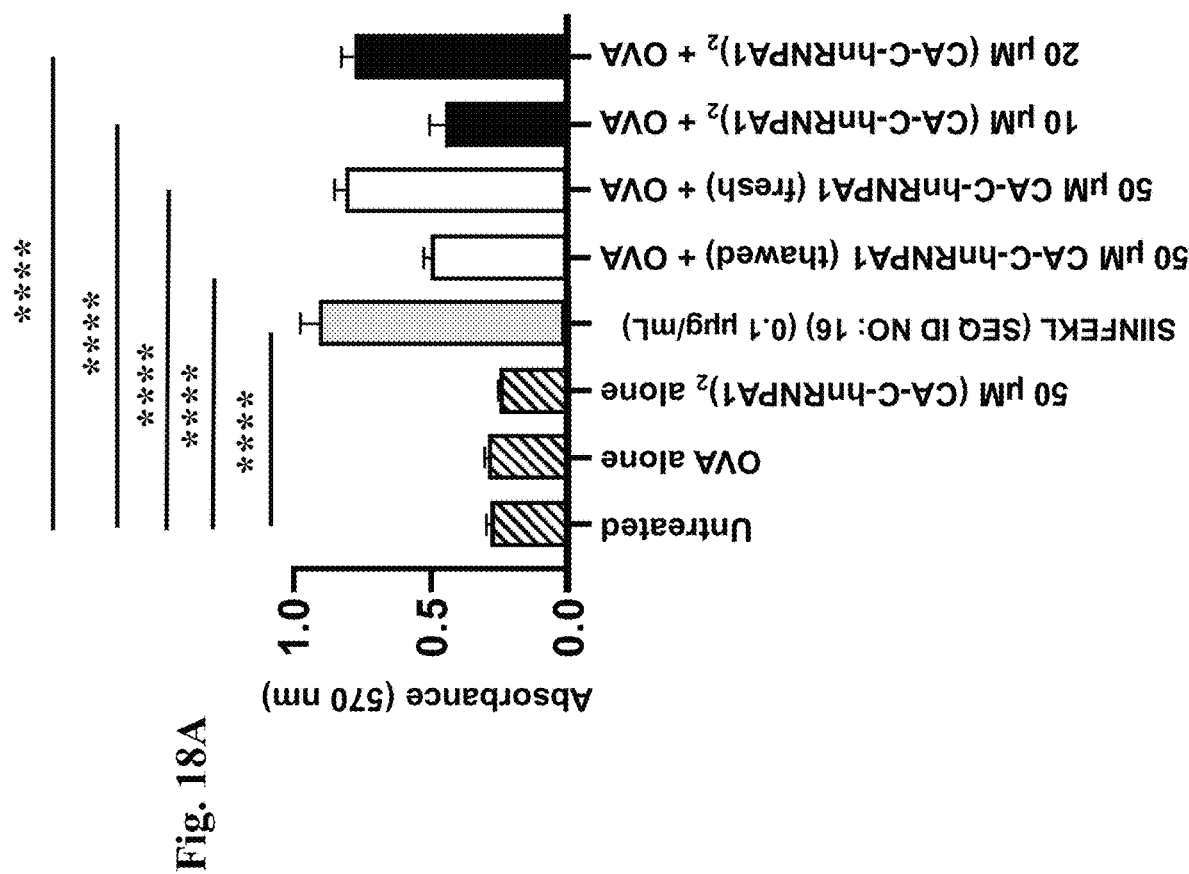
FIGS. 18A-18B shows a comparison between the cross presentation activities of the CA-C-hnRNPA1 monomer and the (CA-C-hnRNPA1)$_2$ dimer (FIGS. 18A and 18B), as well as the (CDCA-C-hnRNPA1)$_2$ dimer (FIG. 18B), using the same wild-type MSC and B3Z reporter system described in PCT/CA2022/051795. The antigen presentation activities of a freshly prepared sample of the CA-C-hnRNPA1 monomer ["CA-C-hnRNPA1 (fresh)"] and an older sample of the CA-C-hnRNPA1 monomer that was previously stored for 3 months at −80° C. prior to use ("CA-C-hnRNPA1 (thawed)") are also compared. **** P<0.0001.
Figure 18B:
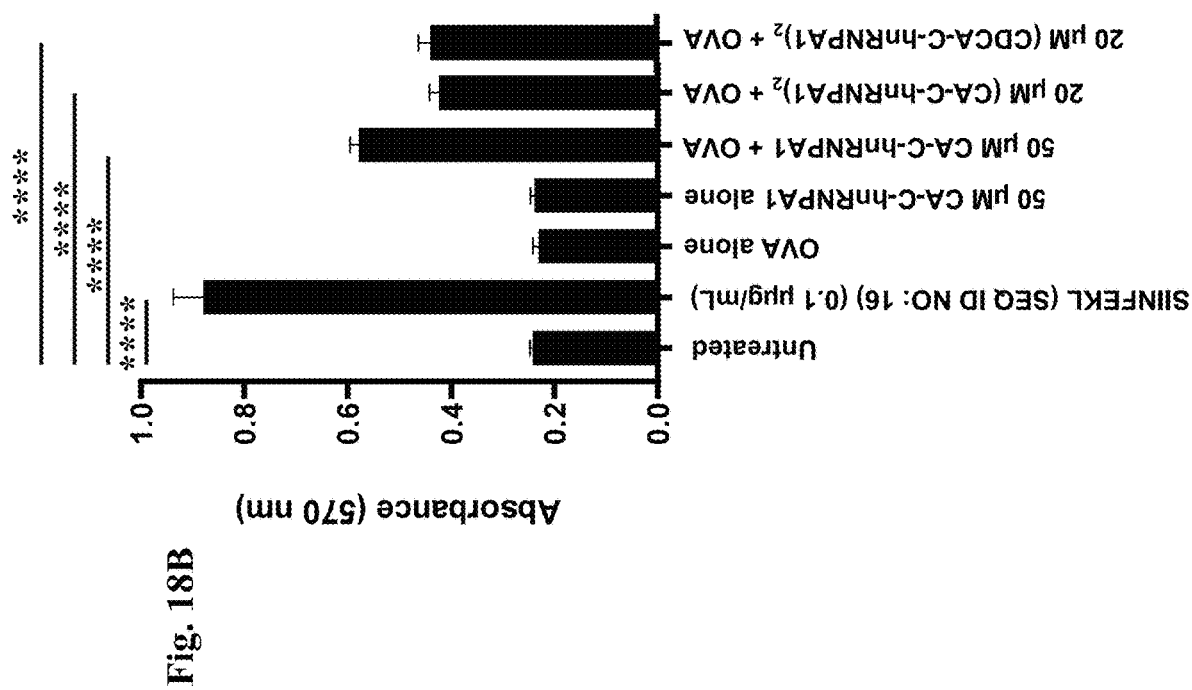

A similar improvement in stability was observed for the (CA-C-hnRNPA1)$_2$ dimer, over its corresponding CA-C-hnRNPA1 monomer (stability testing data not shown). The CA-C-hnRNPA1 monomer was extensively characterized in PCT/CA2022/051795 and was shown to be particularly effective at inducing cargo delivery and enhancing polypeptide antigen presentation in mesenchymal stromal cells (MSCs). FIGS. 18A and 18B compare the cross presentation activities of the CA-C-hnRNPA1 monomer and the (CA-C-hnRNPA1)$_2$ dimer (FIGS. 18A and 18B), as well as the (CDCA-C-hnRNPA1)$_2$ dimer (FIG. 18B), using the same wild-type MSC and B3Z reporter system described in PCT/CA2022/051795. As shown in the FIG. 18, a freshly prepared sample of the CA-C-hnRNPA1 monomer at 50 µM ("CA-C-hnRNPA1 (fresh)") exhibited a level of antigen presentation similar to that of the positive control (0.1 µg/mL of the peptide SIINFEKL (SEQ ID NO: 16)). However, an older sample of the CA-C-hnRNPA1 monomer that was previously stored for 3 months at −80° C. prior to use ("CA-C-hnRNPA1 (thawed)") exhibited reduced antigen presentation activity at the same concentration, suggesting that the reduced stability observed for the monomer corresponds to a reduction in biological activity. Interestingly, the (CA-C-hnRNPA1)$_2$ dimer, as well as the (CDCA-C-hnRNPA1)$_2$ dimer, used at 20 µM exhibited comparable antigen presentation activity as the freshly prepared CA-C-hnRNPA1 monomer.

These results suggest that instability of cysteine-containing steroid acid-peptide conjugates may be greatly improved by protecting their free thiol groups, such as synthesizing the conjugates as dimers having an intermolecular disulfide bond.

Figure 11A:
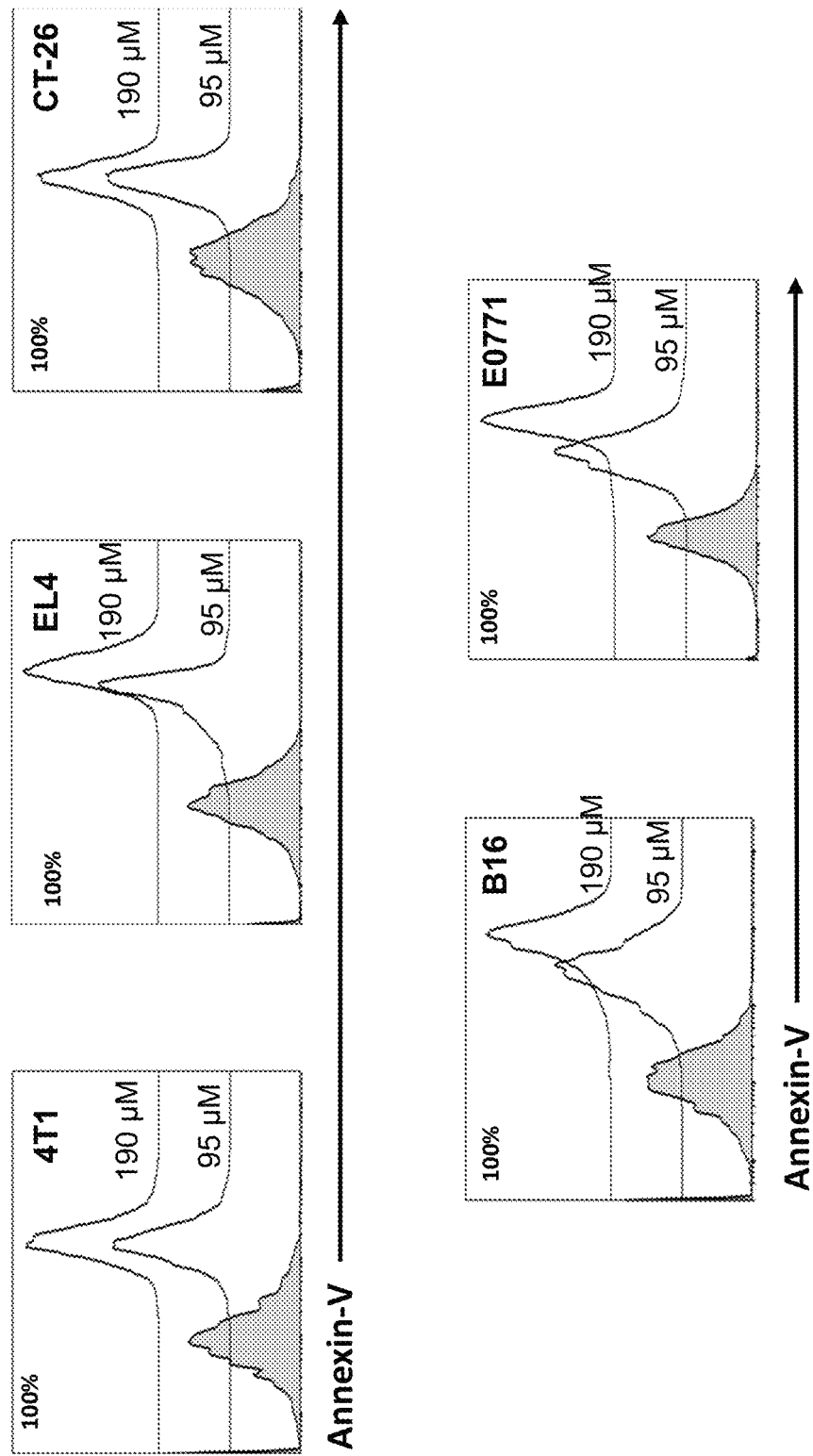
FIGS. 11A-11F shows the enhanced anti-tumoral properties of steroid acid-peptide conjugate dimers (e.g., (CDCA-C-SV40)$_2$.
Figure 11B:
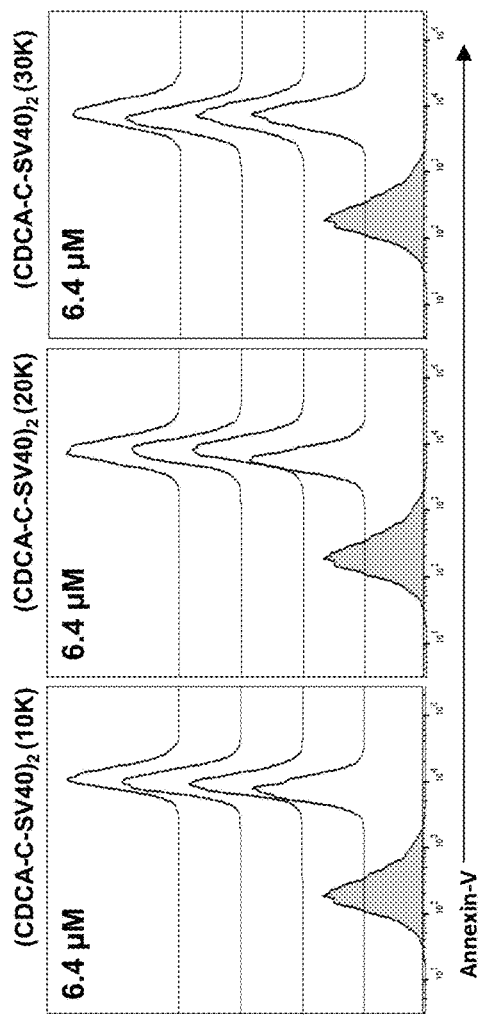
Figure 11C:
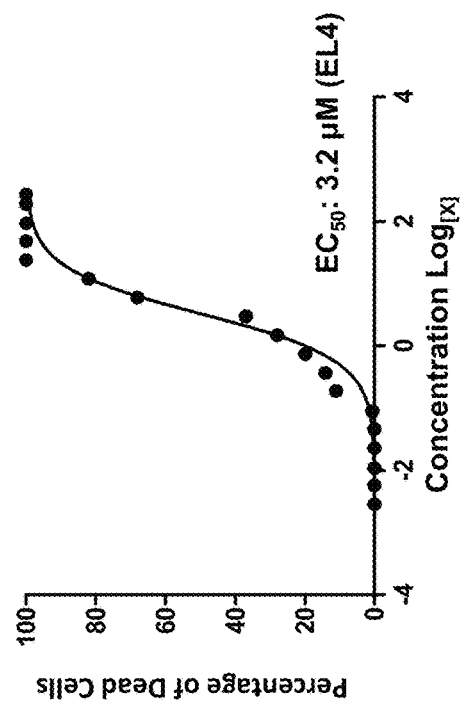

Example 8: Dimerized Steroid Acid-Peptide Conjugates Exhibit Enhanced Cytotoxicity than their Monomeric Counterparts Next, the cytotoxic activity of the dimer (CDCA-C-SV40)$_2$ was assessed. As shown in FIG. 11A, (CDCA-C-SV40)$_2$ exhibited potent cytotoxicity on five different tumor cell lines (4T1 breast cancer cells, EL4 lymphoma cells, CT-26 colon carcinoma cells, B16 melanoma cells, and E0771 breast cancer cells) at two different concentrations (95 and 190 µM), as well as on JIMT-1 cells at 6.4 µM (FIG. 11B). A kill curve analysis of (CDCA-C-SV40)$_2$ on EL4 lymphoma cells (FIG. 11C) revealed that the dimer exhibited cytotoxic activity even at strikingly low concentrations, which were several orders of magnitude below the concentrations required for cytotoxic activity of the monomer. In fact, the half maximal effective concentration (EC$_{50}$) of (CDCA-C-SV40)$_2$ was determined to be 3.2 µM (FIG. 11C).

Figure 11D:
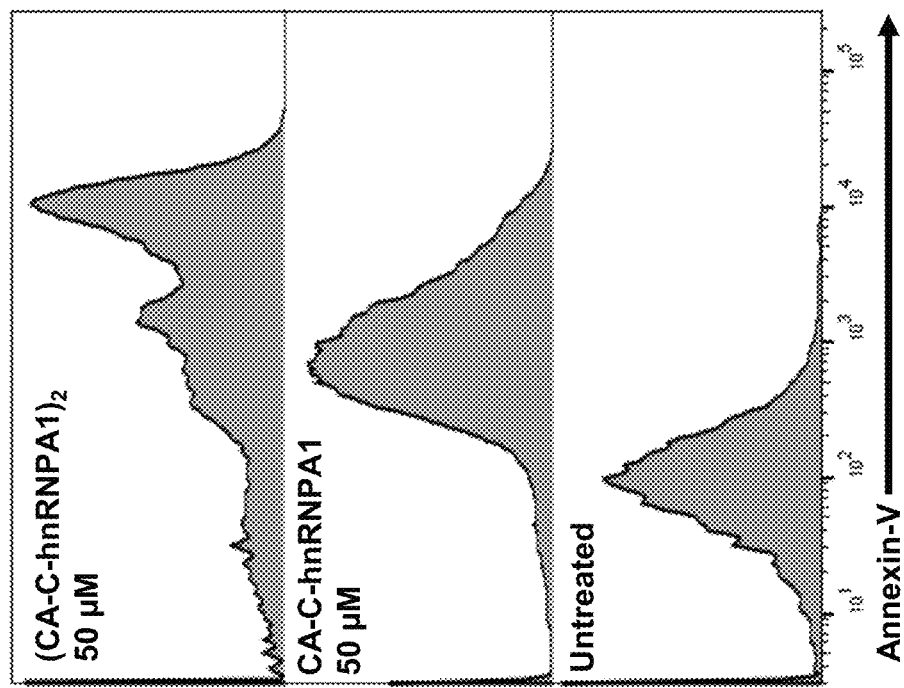
Figure 11F:
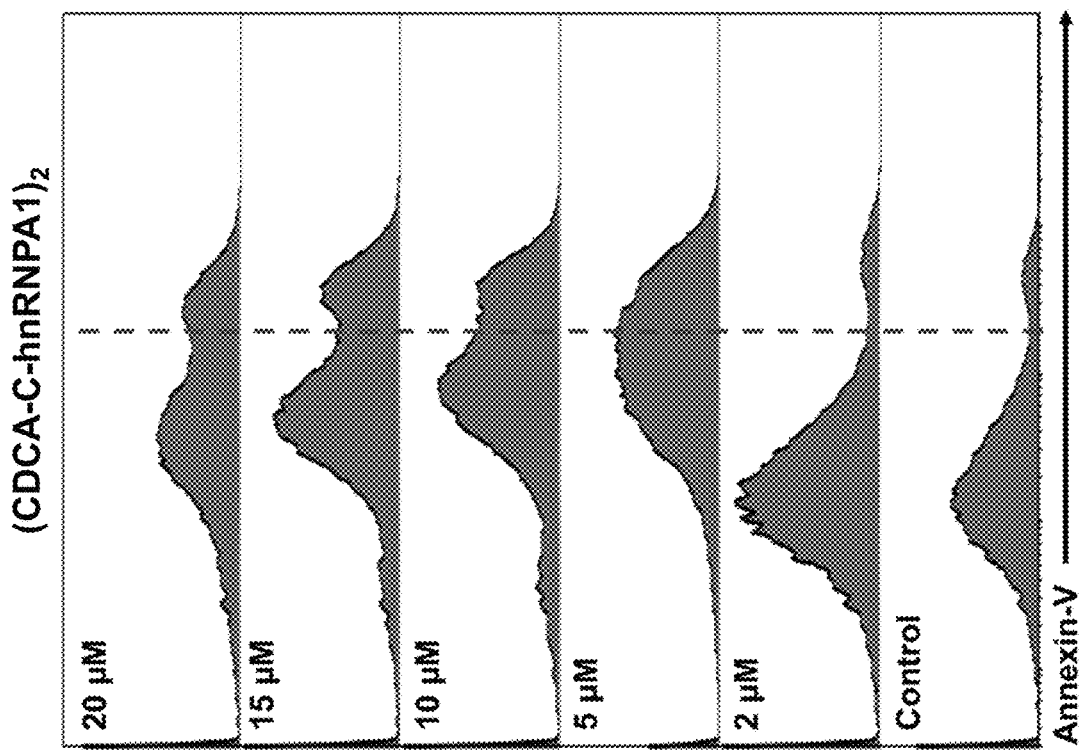
Figure 11E:
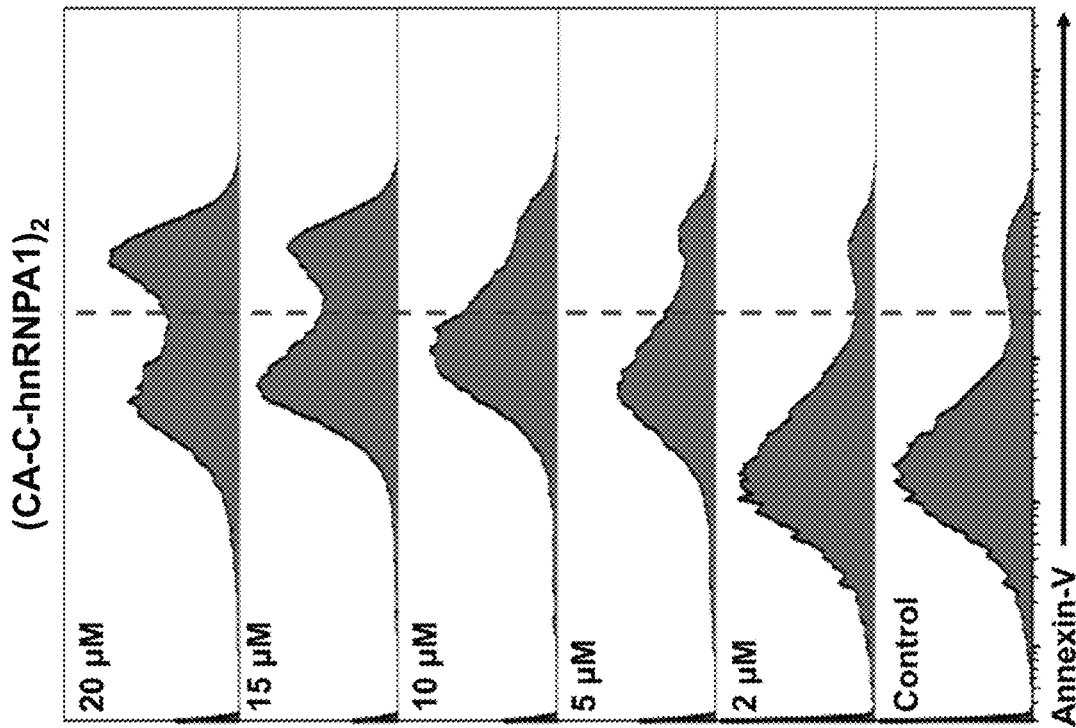

A similar enhancement of cytotoxicity was observed for the (CA-C-hnRNPA1)$_2$ dimer, over its corresponding CA-C-hnRNPA1 monomer in MSCs (FIG. 11D). The cytotoxic effect of the (CA-C-hnRNPA1)$_2$ dimer was observed at different concentrations on MSCs (FIG. 11E), even at concentration as low as 5 µM. Again, a similar enhancement of cytotoxicity was observed for another steroid acid-peptide conjugate dimer, (CDCA-C-hnRNPA1)$_2$, at different concentrations on MSCs (FIG. 11F), even at concentration as low as 5 µM.

Furthermore, enhancement of cytotoxicity in JIMT-1 breast cancer cells was also observed for the dimerized versions of the conjugate [CDCA-C-hnRNP D NLS] and [LEG-CA-C-NLS3 RPS17] (FIGS. 21A and 21B), although the enhancement was not as potent as that observed for the (CDCA-C-SV40)$_2$, (CA-C-hnRNPA1)$_2$, (CDCA-C-hnRNPA1)$_2$ dimers. The conjugate the "LEG" in the conjugate [LEG-CA-C-NLS3 RPS17] refers to a legumain cleavage site ("LEG"; SEQ ID NO: 18) that was inserted N-terminally.

These results suggest that dimerization of steroid acid-peptide monomers may improve their cytotoxicity activity, and that the effect may be synergistic for some conjugates. Furthermore, these data suggest that cleavable linkers may be added to steroid acid-peptide dimers without affecting their cytotoxic properties.

Example 9: Dimerized Steroid Acid-Peptide Conjugates Exhibit Anti-Tumor Activity In Vivo Next, the in vivo antitumoral properties of dimerized steroid acid-peptide conjugates was assessed. Mice were treated with EL4 lymphoma cells and injected with (CDCA-C-SV40)$_2$ at different doses (8 mg/kg and 16 mg/kg), in the presence or absence of the immune checkpoint inhibitor anti-CD47, as previously described in Example 4. As shown in FIGS. 12A and 12B, (CDCA-C-SV40)$_2$ alone at either dose was shown to delay tumor growth and increase survival in mice compared to PBS controls. This effect was enhanced when combined with administration of anti-CD47 Ab.

To test this effect in other tumor models, mice were instead either treated with E0771 breast cancer cells or B16 melanoma cells. As shown in FIGS. 12C-12F, E0771 and B16 tumor growth were significantly inhibited and survival was increased in mice treated with (CDCA-C-SV40)$_2$ (16 mg/kg). This effect was even greater when combined with an immune checkpoint inhibitor, such as anti-CD47 Ab, anti-CTLA-4 Ab, or anti-PD-1 Ab.

These data suggest that dimerized steroid acid-peptide conjugates are suitable and potent candidates for anticancer therapies in vivo.

Figure 13C:
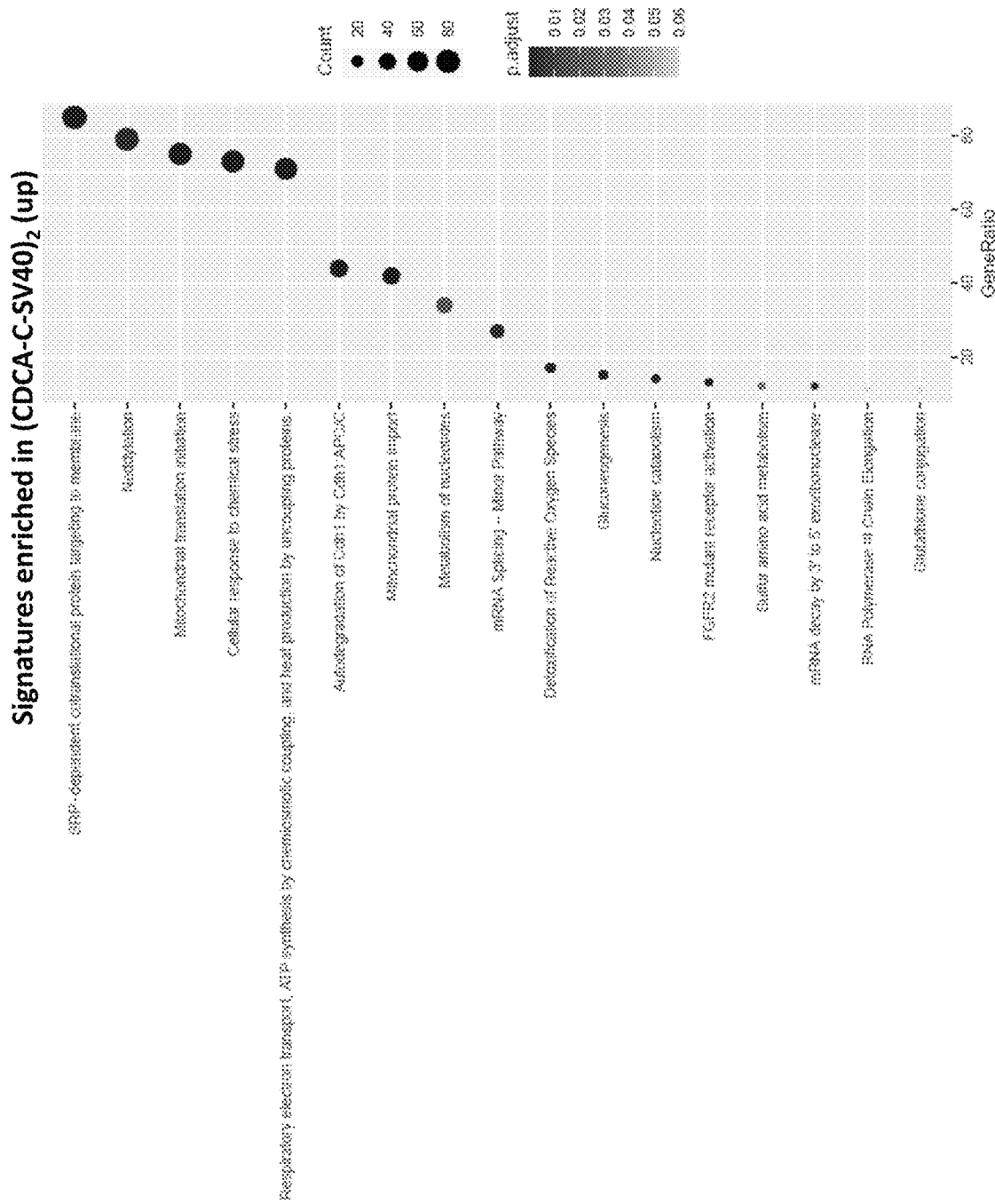
Figure 13D:
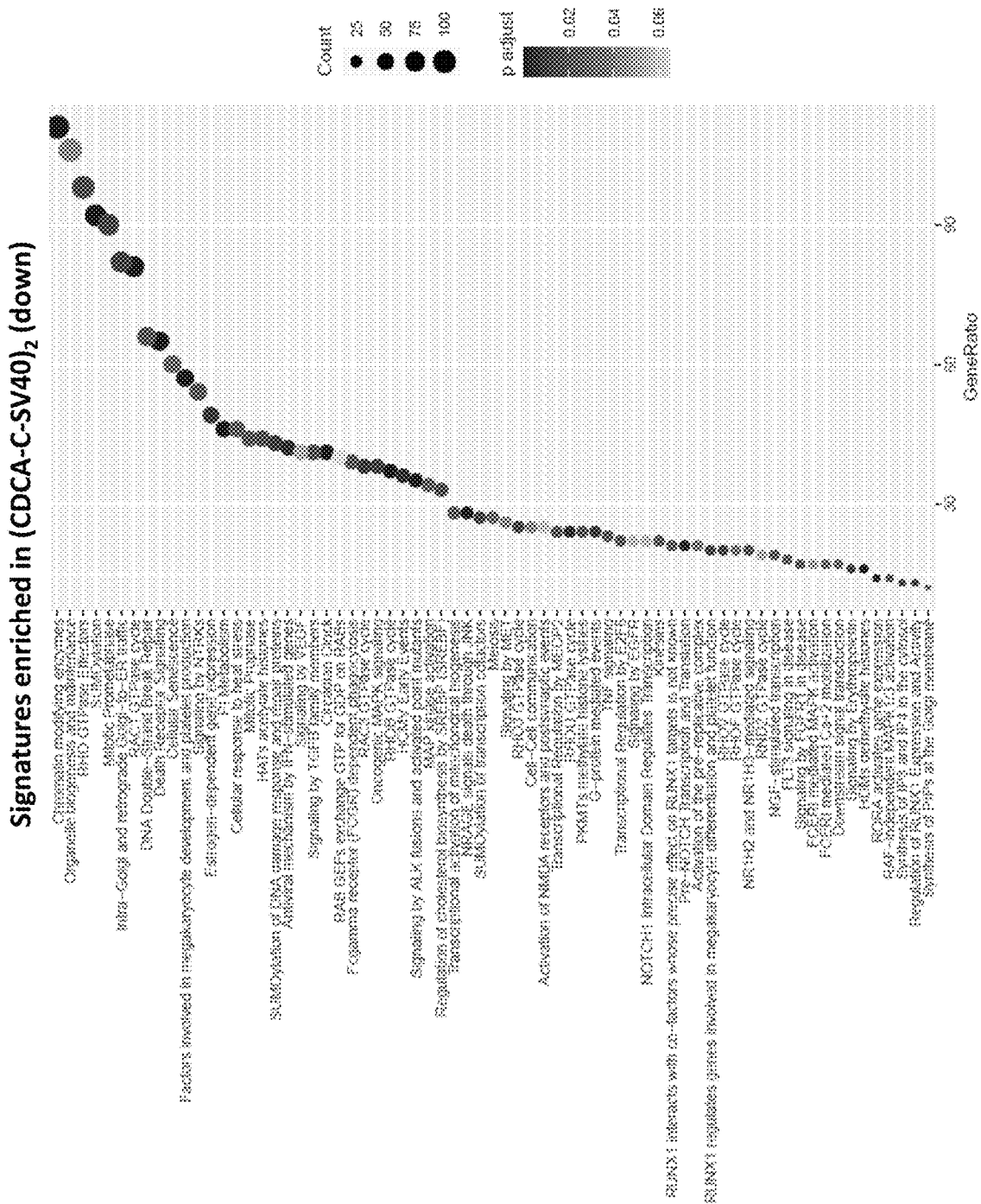
Figure 13E:
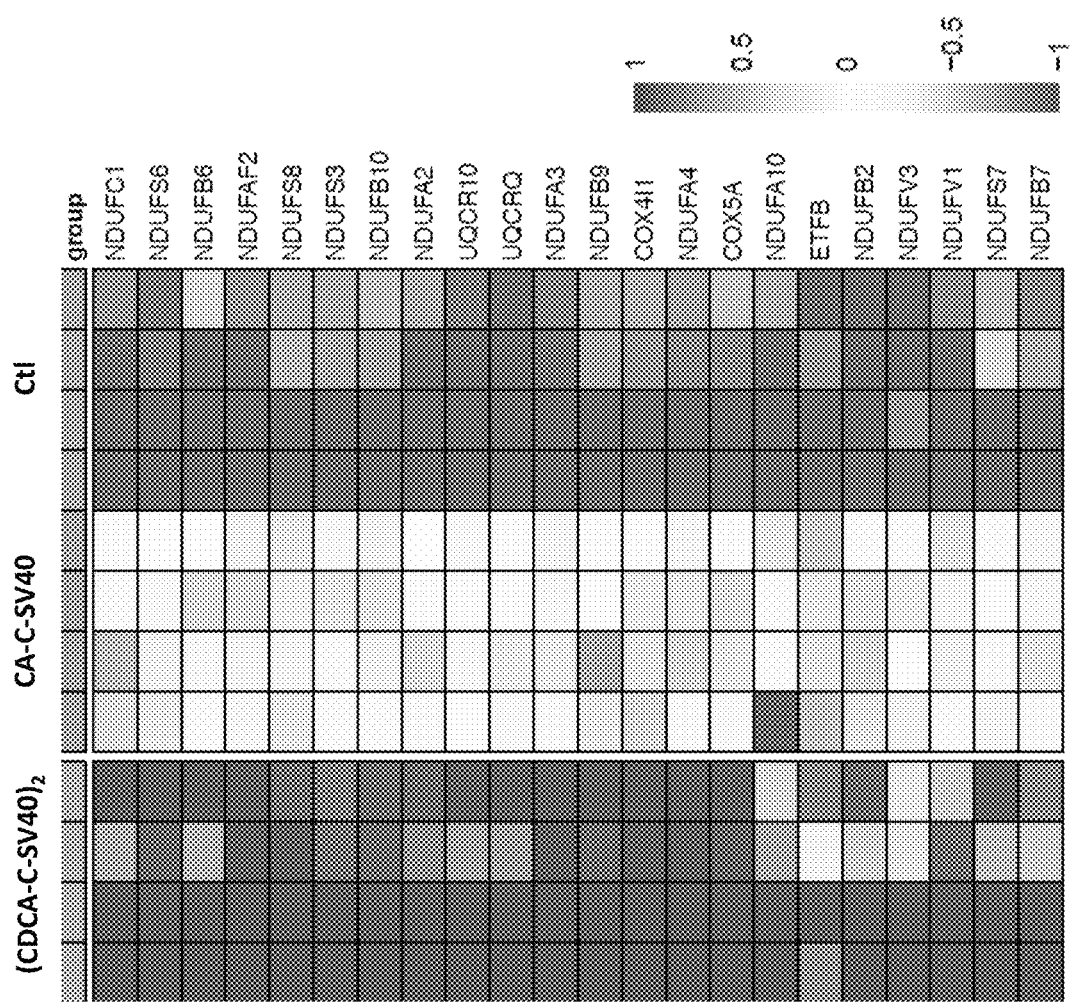
Figure 14:
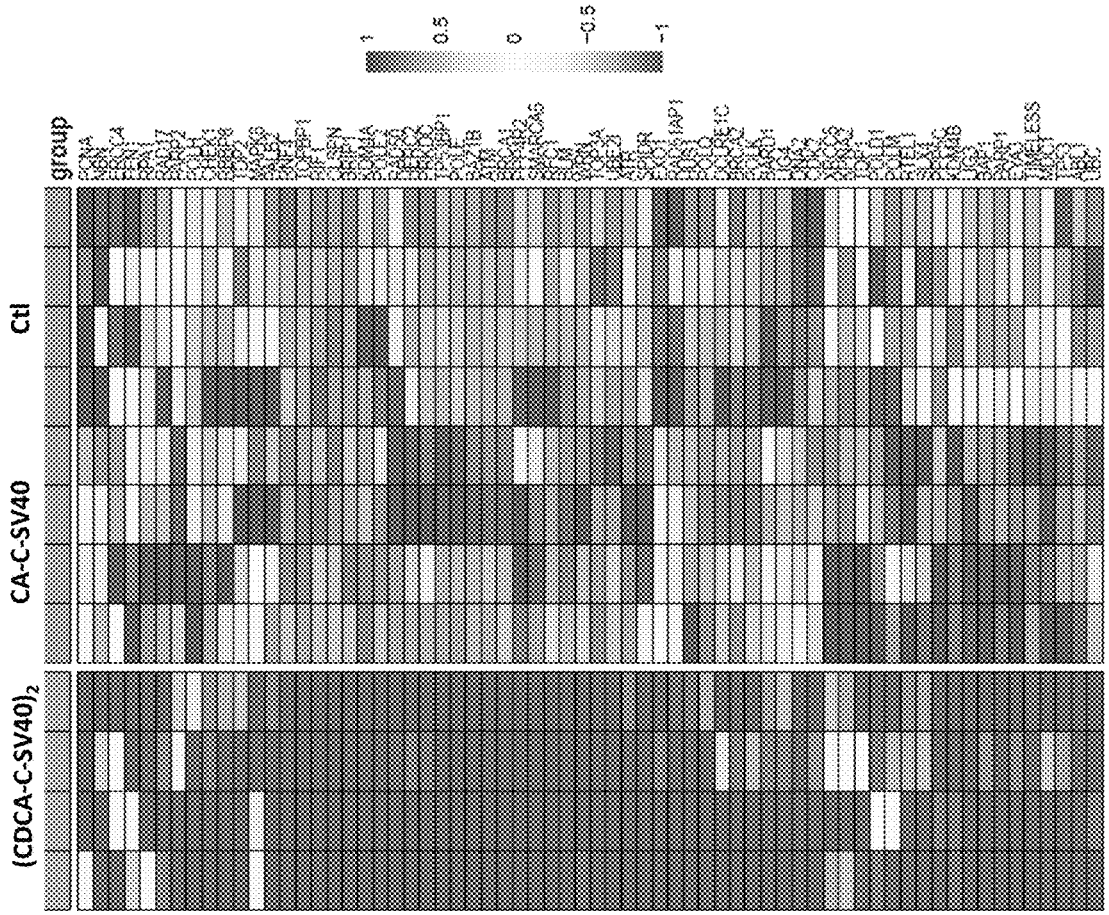
FIG. 14 shows the impairment of expression of DNA repair genes with the treatment of steroid acid-peptide conjugate dimers.

Example 10: Comparison of the Effects of Steroid Acid-Peptide Conjugate Monomers Versus and Dimers on Tumor Gene Signatures FIGS. 13A and 13B show the number of genes that are upregulated and downregulated in EL4 tumor cells treated with CA-C-SV40 (190 µM) and (CDCA-C-SV40)$_2$ (6.4 µM) at their respective EC 100 concentrations, or both. As shown, the number of genes that are either upregulated or downregulated are increased in cells treated with (CDCA-C-SV40)$_2$, as compared to the monomer CA-C-SV40, A list of these genes is provided in FIGS. 13C and 13D, and FIG. 13E shows a heat-map depicting regulation of genes involved in oxidative phosphorylation in response to CA-C-SV40, (CDCA-C-SV40)$_2$, or PBS ("Ctrl"). In particular, genes involved in oxidative phosphorylation are upregulated in response to (CDCA-C-SV40)$_2$ over CA-C-SV40 monomer or control. Furthermore, EL4 cells treated with (CDCA-C-SV40)$_2$ had significantly decreased expression of DNA repair genes, whereas in cells treated with the CA-C-SV40 monomer, these genes were mostly upregulated (FIG. 14).

Figure 15A:
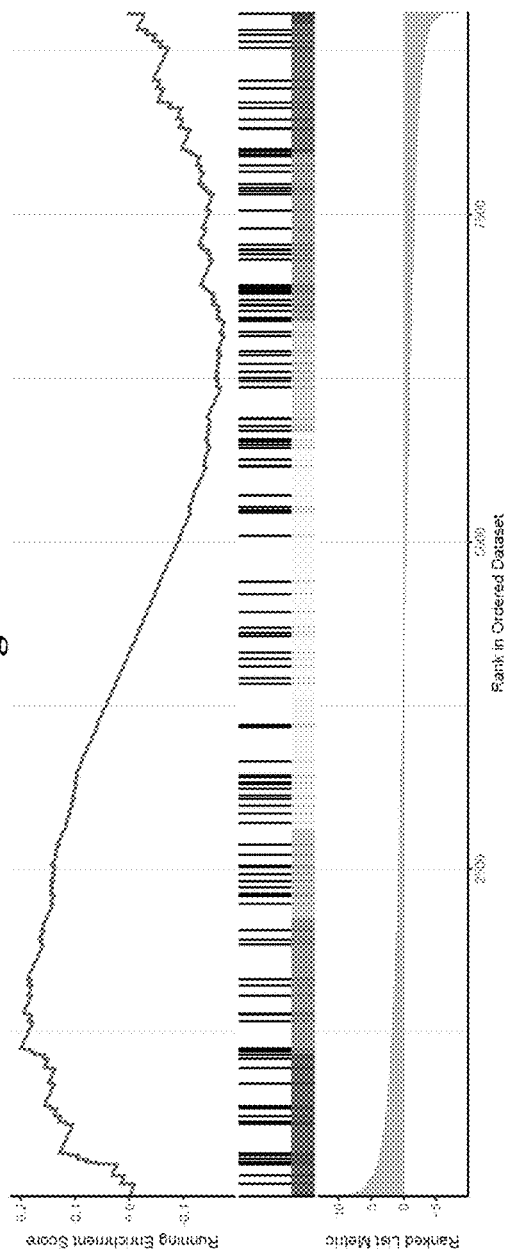
FIGS. 15A-15C shows the regulation of the expression and function of TP53-related genes by (CDCA-C-SV40)$_2$.
Figure 15B:
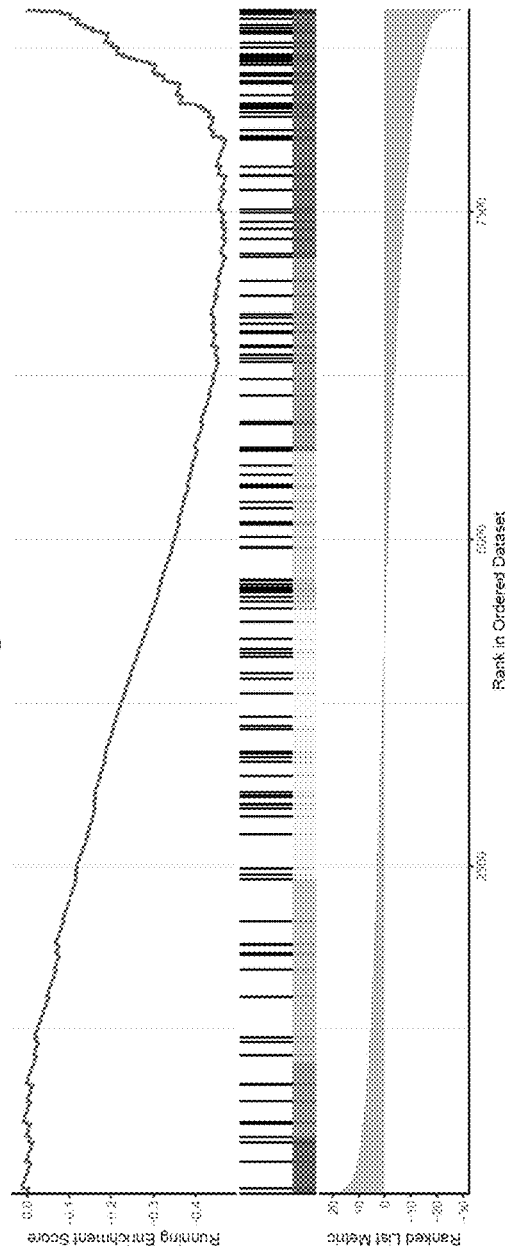
Figure 15C:
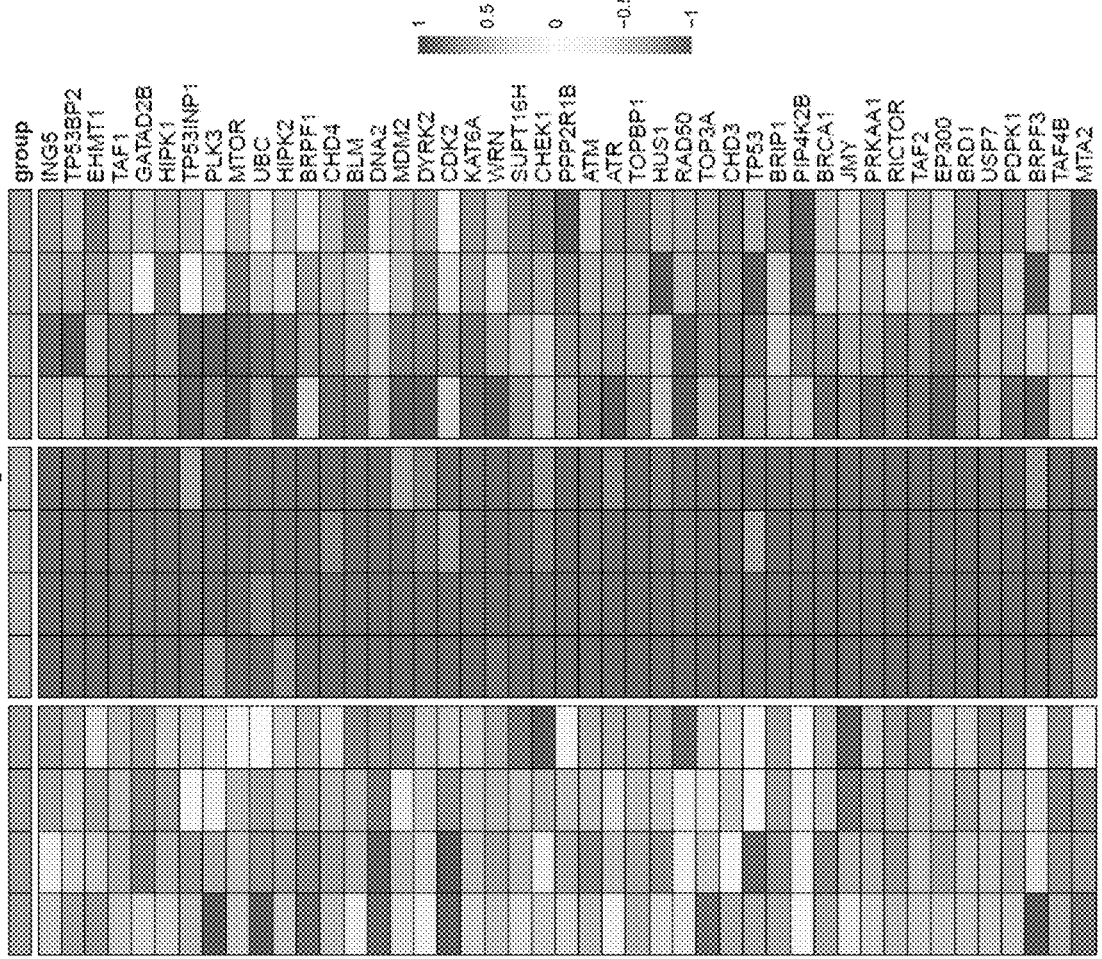

FIGS. 15A-15C show the regulation of the expression and function of TP53-related genes in EL4 tumor cells treated with (CDCA-C-SV40)$_2$ by Gene Set Enrichment Analysis (GSEA). Strikingly, TP53-related genes were significantly downregulated in tumor cells treated with (CDCA-C-SV40)$_2$, as compared to with CA-C-SV40 monomer or control.

Example 11: Dimerized Steroid Acid-Peptide Conjugates Act as Cytotoxic Agents in the Context of Antibody-Drug Conjugates To determine whether the (CDCA-C-SV40)$_2$ dimer could retain its cytotoxic activity in the context of antibody-drug conjugates, the dimer was covalently linked to the anti-HER2 (human epidermal growth factor receptor 2) mAb trastuzumab (Herceptin™). The results in FIG. 16A show that the (CDCA-C-SV40)$_2$ dimer was able to impart cytotoxic activity to the anti-HER2 mAb in JIMP-1 breast cancer cells. This result is in sharp contrast to previous studies showing that conjugating trastuzumab to CA-CSV40 monomers did not enhance impart cytotoxic activity to the antibody in the human breast cancer cell line SKBR3 (Lascasse et al., 2020, see e.g., FIG. 3D).

To determine whether the (CDCA-C-SV40)$_2$ dimer could enhance the cytotoxic activity of a conventional antibody-drug conjugate (ADC), the dimer was covalently linked to the ADC trastuzumab emtansine (T-DM1), as described in Example 1. The results in FIG. 16B show that the (CDCA-C-SV40)$_2$ dimer was able to enhance the cytotoxic activity of T-DM1 in JIMP-1 breast cancer cells. In FIGS. 16A and 16B, trastuzumab and T-DM1 were cleavably linked to (CDCA-C-SV40)$_2$ via an N-terminal 6-azido-L-lysine residue "N$_3$" and a protease-cleavable valine-citrulline linker ("VC").

In FIG. 16C, the impact for a cleavable linker, as well as the N vs C-terminal conjugation to the antibody, were assessed. As shown, conjugates lacking or containing an N-terminal or C-terminal protease-cleavable valine-citrulline linker, showed similar cytotoxicity in JIMT-1 breast cancer cells, but all possessed increased cytotoxicity as compared to treatment with Trastuzumab alone.

These data suggest that dimerized steroid acid-peptide conjugates may be employed as agents to enhance the cytotoxicity of cancer-targeting drugs, such as antibody-drug conjugates. Furthermore, these data suggest that cleavable, as well as non-cleavable, linkers may be added to steroid acid-peptide dimers, at the N-terminus or C-terminus of the peptide, without affecting their cytotoxic properties.

Figure 17A:
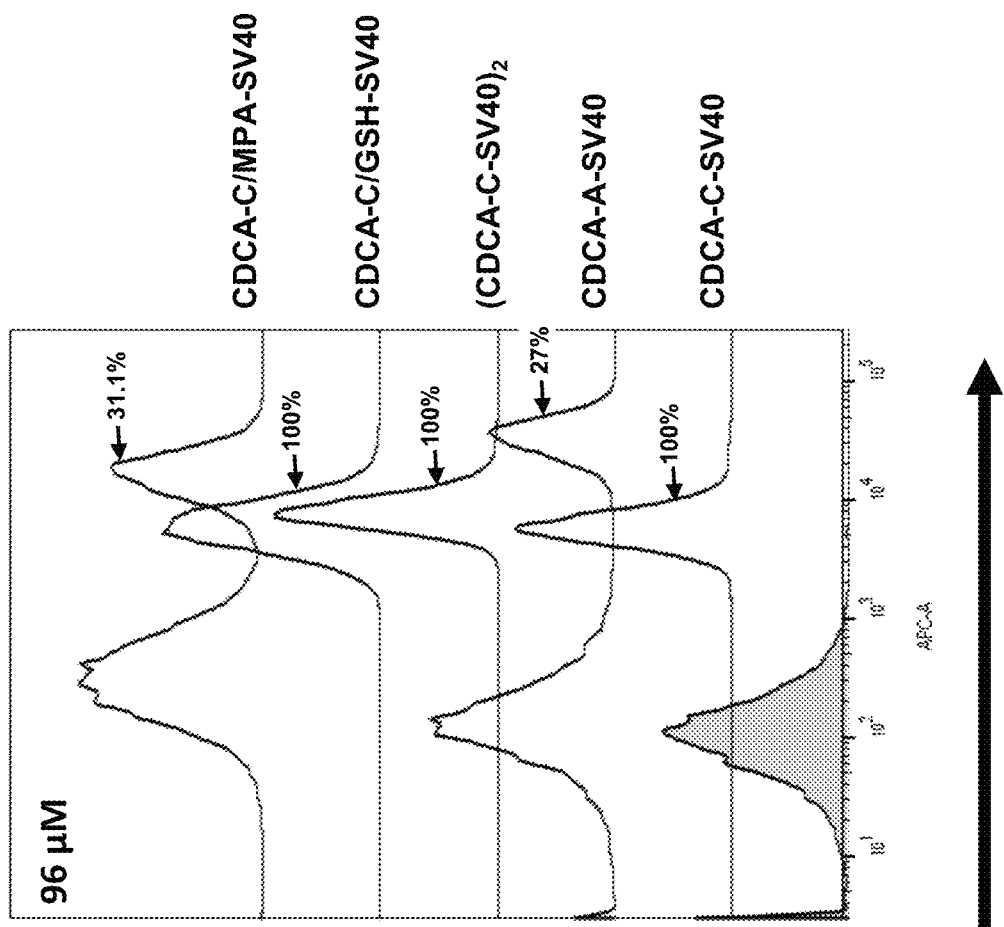
FIGS. 17A and 17B compare the ability of different variants of CDCA-C-SV40 to induce apoptosis in EL4 lymphoma cells.
Figure 17B:
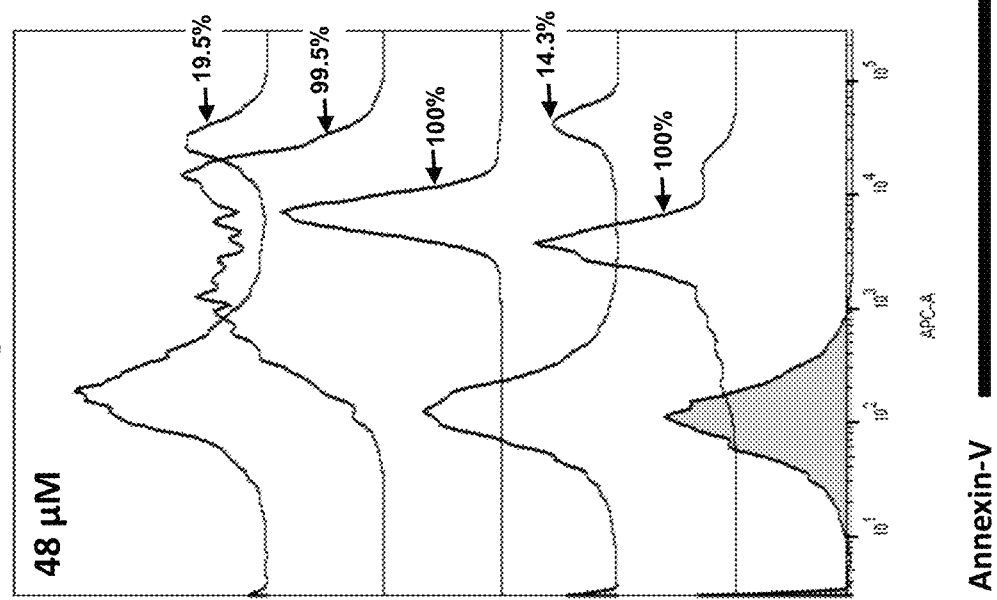

Example 12: Free Thiol Group in Steroid Acid-Peptide Conjugates is Required for Cytotoxic Activity In general, steroid acid-peptide conjugates described herein were chemically synthesized to include an N-terminal cysteine residue to provide an additional functional group (i.e., thiol side chain of cysteine residue) for potential conjugation reactions (e.g., to antibodies). The steroid acid is then conjugated to the free amino group of the N-terminal cysteine residue, thus leaving the thiol side chain of the cysteine free. However, the results in Example 7 suggest that the presence of a free thiol group in the CDCA-C-SV40 monomer was a potential source of instability and impurity due to thiol oxidation and the appearance of dimers caused by intermolecular disulfide bonds. To evaluate the impact of removing the free thiol group on the activity of steroid acid-peptide conjugates, a variant of CDCA-C-SV40 was synthesized in which the C-terminal cysteine residue was replaced with an alanine residue, to produce the monomer "CDCA-A-SV40". Two further variants were synthesized in which the free thiol group CDCA-C-SV40 was protected with either a non-cleavable protecting group (MPA; 3-mercaptopropionic acid) to produce "CDCA-C/MPA-SV40", or with a cleavable protecting group (glutathione; GSH) to produce "CDCA-C/GSH-SV40". The ability of these three variants to induce apoptosis in EL4 lymphoma cells was then evaluated and compared to that of the CDCA-C-SV40 monomer and the (CDCA-C-SV40)$_2$ dimer, at two different concentrations: 48 µM and 96 µM. As shown in FIG. 17A, conjugates containing a free thiol group (i.e., the CDCA-C-SV40 monomer) or containing a thiol group protected in a cleavable manner due to the reducing environment of the cytosol (i.e., CDCA-C/GSH-SV40 and (CDCA-C-SV40)$_2$ dimer), were able to induce apoptosis in over 99% of cells when used at the lower tested dose. In contrast, conjugates lacking a free thiol group (i.e., CDCA-A-SV40) or containing a thiol group protected in a non-cleavable manner (i.e., CDCA-C/MPA-SV40) induced less apoptosis when used at the lower tested dose (FIG. 17A), but their levels of apoptosis-induction could be increased with higher concentrations of these conjugates (FIG. 17B).

These results suggest that steroid acid-peptide conjugates containing one or more free or freeable thiol groups (e.g., a thiol group protected in a cleavable manner) may be more potent inducers of apoptosis than steroid acid-peptide conjugates lacking a free thiol group or containing a thiol group protected in a non-cleavable manner. Due to the reducing microenvironment of tumor cells, the design of reduction-activated steroid acid-peptide conjugates comprising freeable thiol groups may be envisaged.

Figure 19B:
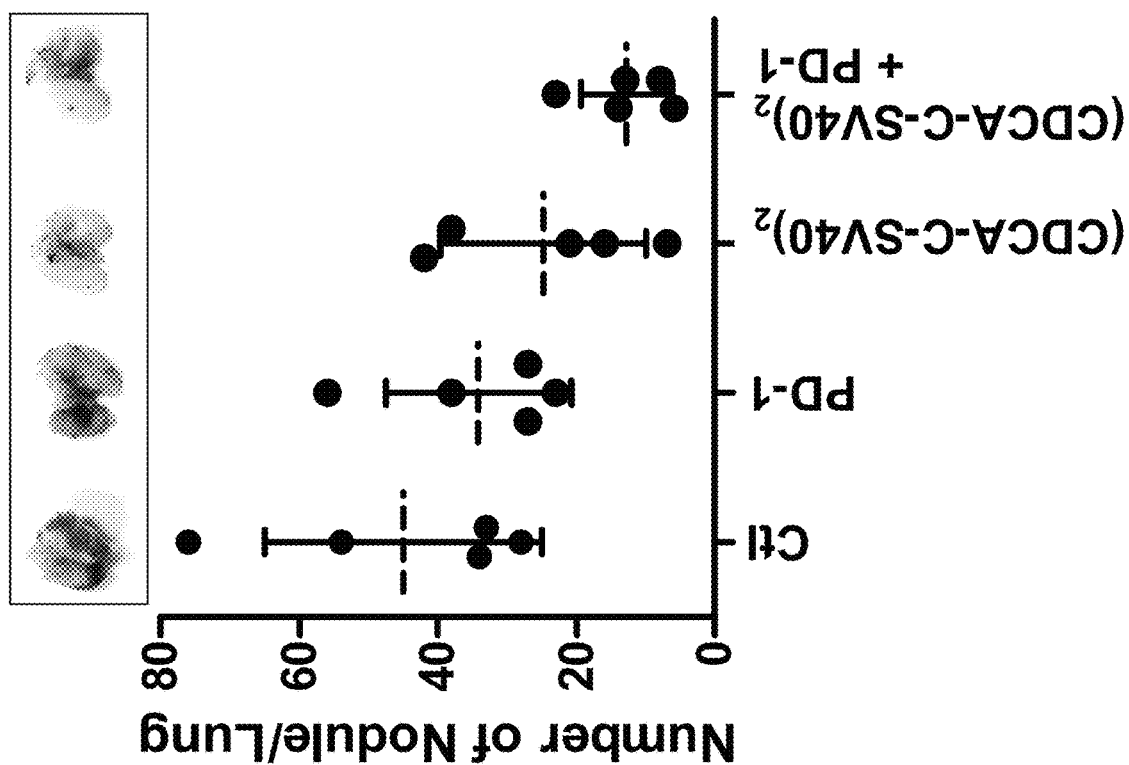
FIGS. 19A-19B show the results of intranasal administration of (CDCA-C-SV40)$_2$ in an in vivo model of B16F10 tumor.
Figure 19A:
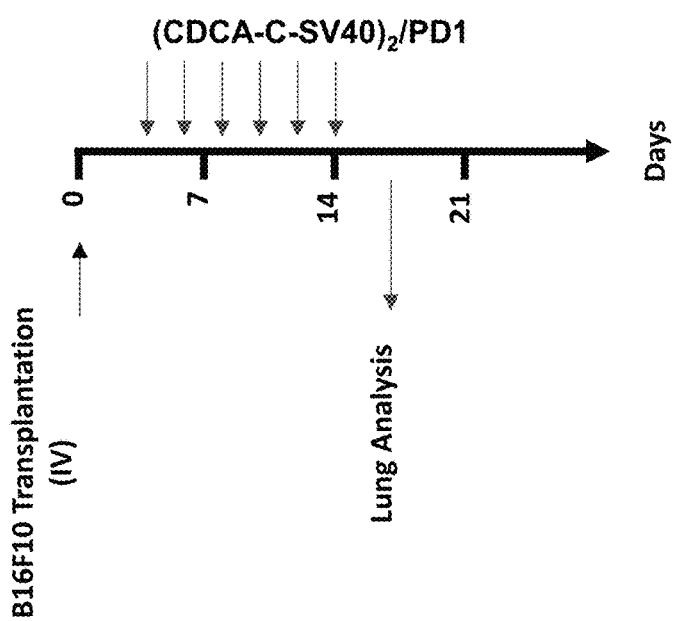

Example 13: Dimerized Steroid Acid-Peptide Conjugates Exhibit Anti-Tumor Activity in an In Vivo B16F10 Tumor Model Via Intranasal Administration FIGS. 19A-19B show the results of intranasal administration of (CDCA-C-SV40)$_2$ in an in vivo model of B16F10 tumor. Briefly, mice were injected intravenously with B16F10 tumor cells, which migrate to the lung and develop nodules. Mice were then treated with (CDCA-C-SV40)$_2$ intranasally and/or anti-PD-1 intraperitoneally according to the method described in Example 1. FIG. 19A shows a schematic diagram of the experimental design and immunization scheme. FIG. 19B shows a pictogram of the isolated lungs (black dots represent tumor nodules) following treatments with PBS (Ctl), anti-PD-1 alone, (CDCA-C-SV40)$_2$ alone, or the combination of (CDCA-C-SV40)$_2$ and anti-PD-1, as well the number of B16F10 nodules/per mouse (n=5/group). (CDCA-C-SV40)$_2$ intranasal administration was shown to reduce the number of macroscopic modules in the lungs of mice in comparison to control (PBS) and anti-PD-1 alone. This effect was shown to be enhanced with the addition of anti-PD-1.

These data suggests that dimerized steroid acid-peptide conjugates can be administered intranasally and further for the treatment of cancers requiring or benefitting from intranasal treatment.

Figure 20A:
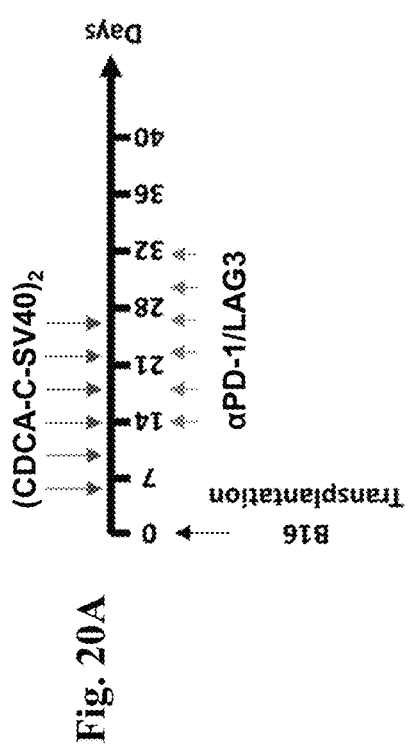
FIGS. 20A-20C show the results of intratumoral administration of (CDCA-C-SV40)$_2$ in an in vivo model of B16F10 tumor.
Figure 20B:
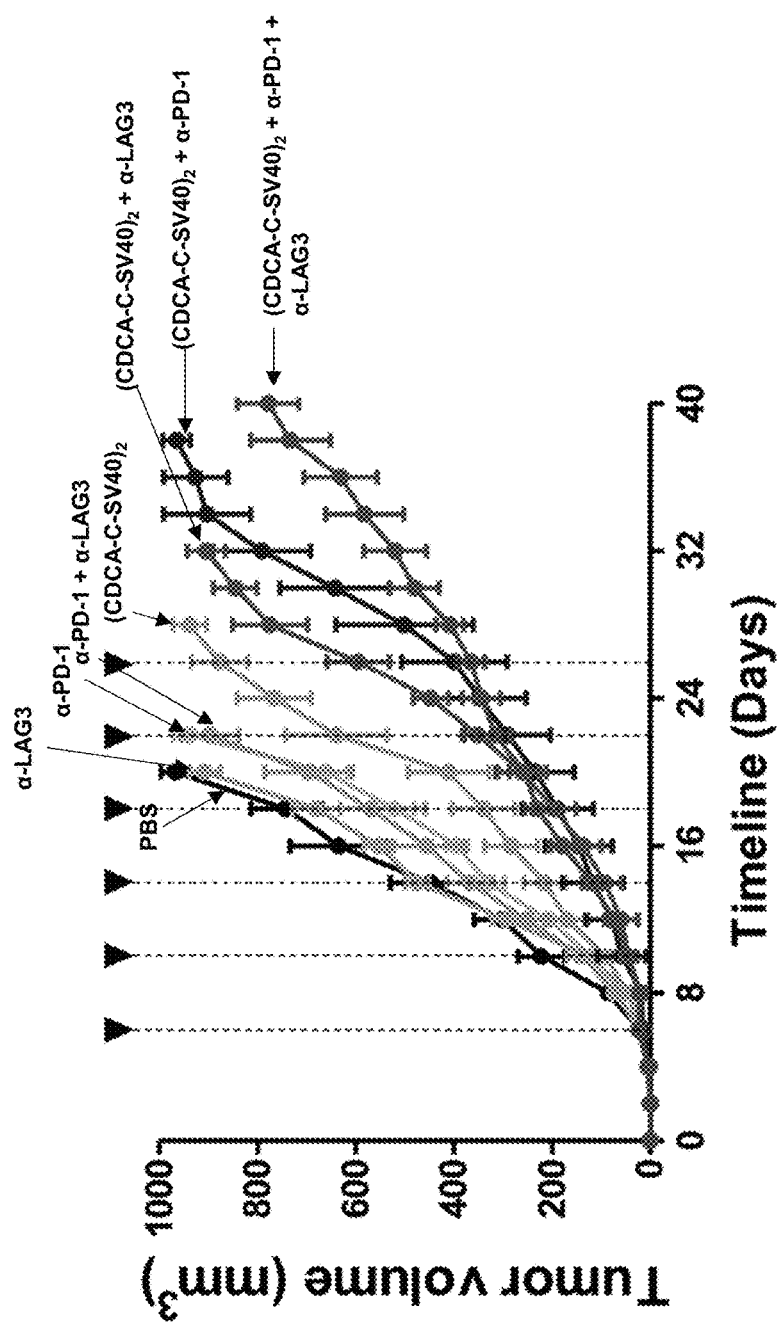
Figure 20C:
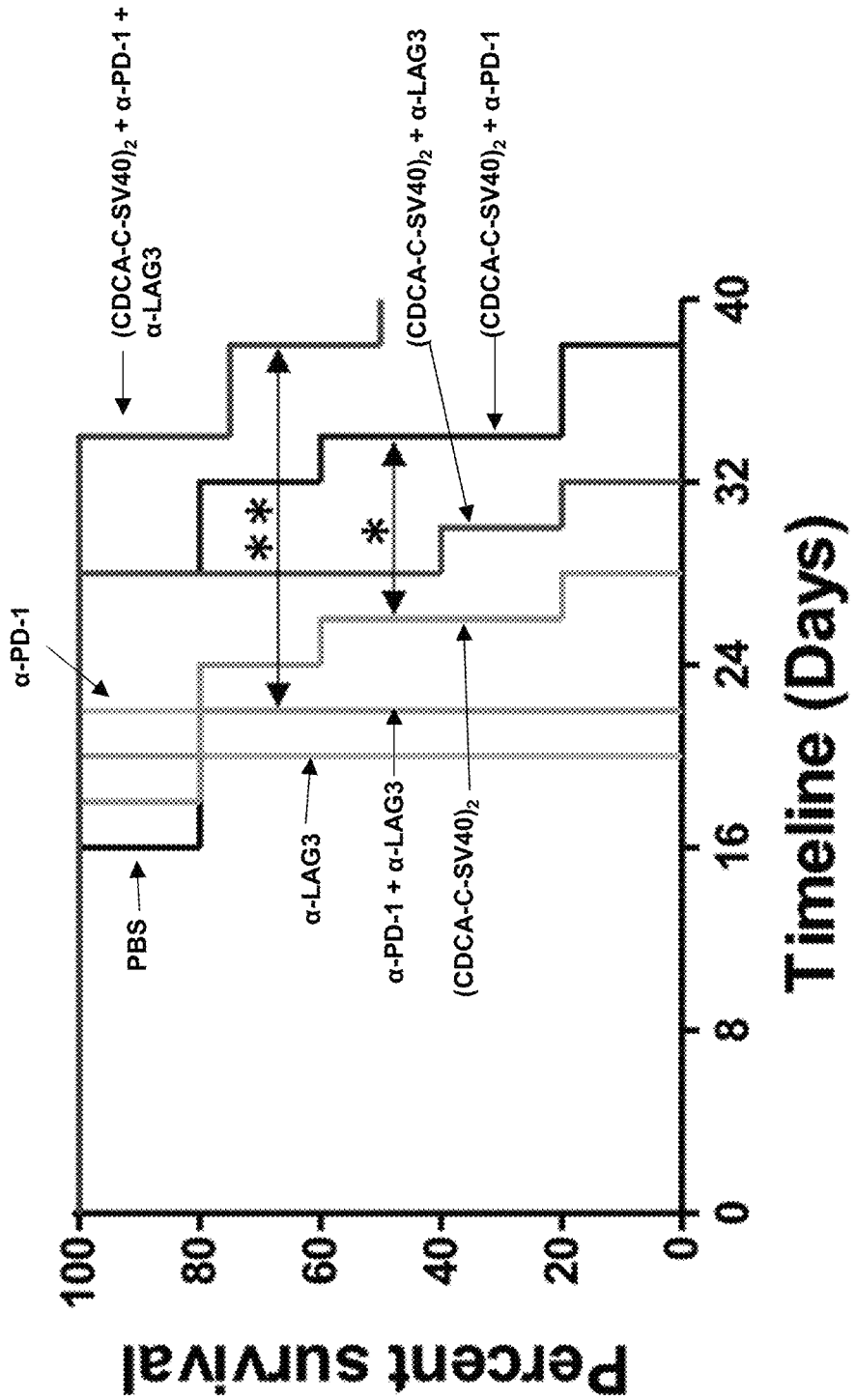

Example 14: Dimerized Steroid Acid-Peptide Conjugates Exhibit Anti-Tumor Activity in an In Vivo B16F10 Tumor Model Via Intertumoral Administration FIGS. 20A-20C show the results of intratumoral administration of (CDCA-C-SV40)$_2$ in an in vivo model of B16F10 tumor. Briefly, mice were transplanted subcutaneously with B16F10 tumor cells. Mice were then treated with (CDCA-C-SV40)$_2$ intratumorally either alone or in combination with anti-PD-1 and/or anti-LAG3 intraperitoneally according to the method describe in Example 1. FIG. 20A shows a schematic diagram of the experimental design and immunization scheme. FIG. 20A shows a schematic diagram of the experimental design and immunization scheme. For this experiment, (CDCA-C-SV40)$_2$ was delivered twice a week for a total of 6 injections (16 mg/kg). FIG. 20B shows the assessment of tumor volume overtime following treatment with PBS, anti-PD-1, anti-LAG3, anti-PD-1+anti-LAG3, (CDCA-C-SV40)$_2$, (CDCA-C-SV40)$_2$+anti-PD-1, (CDCA-C-SV40)$_2$+anti-LAG3, and (CDCA-C-SV40)$_2$+anti-PD-1+anti-LAG3. FIG. 20C shows Kaplan-Meier survival curve for the experiment in FIG. 20B. (CDCA-C-SV40)$_2$ intratumoral administration was shown to reduce the tumor volume, as well as enhance survival, in mice, as compared to control (PBS) and anti-PD-1 alone or anti-LAG3 alone. This effect was enhanced with the addition of either anti-PD-1 or anti-LAG3, as well as with the combination of anti-PD-1 and anti-LAG3.

These data further support the antitumoral effect of dimerized steroid acid-peptide conjugates, either alone or in combination with various immune checkpoint inhibitors.

REFERENCES

Beaudoin et al., (2016). ChAcNLS, a novel modification to antibody-conjugates permitting target cell-specific endosomal escape, localization to the nucleus and enhanced total intracellular accumulation. *Molecular Pharmaceutics,* 13(6): 1915-26.

Beck et al., (2017). Strategies and challenges for the next generation of antibody-drug conjugates. *Nature Reviews Drug Discovery,* 16: 315-337.

Hanafi et al., (2018). Overview of Bile Acids Signaling and Perspective on the Signal of Ursodeoxycholic Acid, the Most Hydrophilic Bile Acid, in the Heart. *Biomolecules,* 8(4): 159.

Lacasse et al., (2020). A Novel Proteomic Method Reveals NLS Tagging of T-DM1 Contravenes Classical Nuclear Transport in a Model of HER2-Positive Breast Cancer. *Molecular Therapy: Methods & Clinical Development,* 19: 99-119.

Murakami et al., (2020). Bile acids and ceramide overcome the entry restriction for GII.3 human norovirus replication in human intestinal enteroids. *Proceedings of the National Academy of Sciences USA.* 117(3):1700-1710.

Shivanna et al., (2014) The crucial role of bile acids in the entry of porcine enteric calicivirus. *Virology* 456-457, 268-278.

Shivanna et al., (2015). Ceramide formation mediated by acid sphingomyelinase facilitates endosomal escape of caliciviruses. *Virology,* 483, 218-228.

Sun et al., (2016). Factors influencing the nuclear targeting ability of nuclear localization signals. *Journal of Drug Targeting,* 24(10): 927-933.

Wang et al., (2020). HMGB1 in inflammation and cancer. *Journal of Hematology & Oncology,* 13:116.

WO/2022/126239

WO/2022/232945

```
SEQUENCE LISTING

Sequence total quantity: 25
SEQ ID NO: 1           moltype = AA  length = 13
FEATURE                Location/Qualifiers
MOD_RES                1
                       note = Cholic Acid (ChAc)
source                 1..13
                       mol_type = protein
                       organism = synthetic construct
SEQUENCE: 1
CGYGPKKKRK VGG                                                            13

SEQ ID NO: 2           moltype = AA  length = 7
FEATURE                Location/Qualifiers
source                 1..7
                       mol_type = protein
                       organism = synthetic construct
SEQUENCE: 2
PKKKRKV                                                                    7

SEQ ID NO: 3           moltype = AA  length = 19
FEATURE                Location/Qualifiers
source                 1..19
                       mol_type = protein
                       organism = synthetic construct
SEQUENCE: 3
CGWWGYGPKK KRKVGGWWG                                                      19

SEQ ID NO: 4           moltype = AA  length = 20
FEATURE                Location/Qualifiers
source                 1..20
                       mol_type = protein
                       organism = synthetic construct
SEQUENCE: 4
CSNFGPMKGG NFGGRSSGPY                                                     20

SEQ ID NO: 5           moltype = AA  length = 20
FEATURE                Location/Qualifiers
source                 1..20
                       mol_type = protein
                       organism = synthetic construct
SEQUENCE: 5
CSGYGKVSRR GGHQNSYKPY                                                     20

SEQ ID NO: 6           moltype = AA  length = 20
FEATURE                Location/Qualifiers
source                 1..20
                       mol_type = protein
                       organism = synthetic construct
SEQUENCE: 6
CNEKRKEKNI KRGGNRFEPY                                                     20

SEQ ID NO: 7           moltype = AA  length = 21
```

```
FEATURE                 Location/Qualifiers
source                  1..21
                        mol_type = protein
                        organism = synthetic construct
SEQUENCE: 7
CADREEGKER RHHRREELAP Y                                              21

SEQ ID NO: 8            moltype = AA  length = 34
FEATURE                 Location/Qualifiers
source                  1..34
                        mol_type = protein
                        organism = synthetic construct
SEQUENCE: 8
CNKRVCEEIA IIPSKKLRNK GSGRIQRGPV RGIS                                34

SEQ ID NO: 9            moltype = AA  length = 16
FEATURE                 Location/Qualifiers
source                  1..16
                        mol_type = protein
                        organism = synthetic construct
SEQUENCE: 9
CMGRVRTKTV KKAAGG                                                    16

SEQ ID NO: 10           moltype = AA  length = 20
FEATURE                 Location/Qualifiers
source                  1..20
                        mol_type = protein
                        organism = synthetic construct
SEQUENCE: 10
CNKRVCEEIA IIPSKKLRNK                                                20

SEQ ID NO: 11           moltype = AA  length = 20
FEATURE                 Location/Qualifiers
source                  1..20
                        mol_type = protein
                        organism = synthetic construct
SEQUENCE: 11
CSKKLRNKIA GYVTHLMKRI                                                20

SEQ ID NO: 12           moltype = AA  length = 15
FEATURE                 Location/Qualifiers
source                  1..15
                        mol_type = protein
                        organism = synthetic construct
SEQUENCE: 12
CGYGPAAKRV KLDGG                                                     15

SEQ ID NO: 13           moltype = AA  length = 22
FEATURE                 Location/Qualifiers
source                  1..22
                        mol_type = protein
                        organism = synthetic construct
SEQUENCE: 13
CGRFSPMGVD HMSGLSGVNV PG                                             22

SEQ ID NO: 14           moltype = AA  length = 15
FEATURE                 Location/Qualifiers
source                  1..15
                        mol_type = protein
                        organism = synthetic construct
SEQUENCE: 14
CGYGKLKIKR PVKGG                                                     15

SEQ ID NO: 15           moltype = AA  length = 21
FEATURE                 Location/Qualifiers
source                  1..21
                        mol_type = protein
                        organism = synthetic construct
SEQUENCE: 15
CAVKRPAATK KAGQAKKKKL D                                              21

SEQ ID NO: 16           moltype = AA  length = 8
FEATURE                 Location/Qualifiers
source                  1..8
                        mol_type = protein
                        organism = synthetic construct
SEQUENCE: 16
SIINFEKL                                                             8
```

```
SEQ ID NO: 17              moltype = AA   length = 13
FEATURE                    Location/Qualifiers
source                     1..13
                           mol_type = protein
                           organism = synthetic construct
MOD_RES                    1
                           note = Cholic Acid (ChAc)
SEQUENCE: 17
AGYGPKKKRK VGG                                                          13

SEQ ID NO: 18              moltype = AA   length = 7
FEATURE                    Location/Qualifiers
source                     1..7
                           mol_type = protein
                           organism = synthetic construct
SEQUENCE: 18
GGAANGG                                                                 7

SEQ ID NO: 19              moltype = AA   length = 18
FEATURE                    Location/Qualifiers
source                     1..18
                           mol_type = protein
                           organism = synthetic construct
VARIANT                    13
                           note = X is any AA or absent
VARIANT                    14
                           note = X is any AA or absent
SEQUENCE: 19
KRXXXXXXXX XXXXKRRK                                                     18

SEQ ID NO: 20              moltype = AA   length = 4
FEATURE                    Location/Qualifiers
source                     1..4
                           mol_type = protein
                           organism = synthetic construct
SEQUENCE: 20
GFGG                                                                    4

SEQ ID NO: 21              moltype = AA   length = 4
FEATURE                    Location/Qualifiers
source                     1..4
                           mol_type = protein
                           organism = synthetic construct
SEQUENCE: 21
GFWG                                                                    4

SEQ ID NO: 22              moltype = AA   length = 5
FEATURE                    Location/Qualifiers
source                     1..5
                           mol_type = protein
                           organism = synthetic construct
SEQUENCE: 22
GFWFG                                                                   5

SEQ ID NO: 23              moltype = AA   length = 4
FEATURE                    Location/Qualifiers
source                     1..4
                           mol_type = protein
                           organism = synthetic construct
SEQUENCE: 23
GWWG                                                                    4

SEQ ID NO: 24              moltype = AA   length = 6
FEATURE                    Location/Qualifiers
source                     1..6
                           mol_type = protein
                           organism = synthetic construct
SEQUENCE: 24
GWGGWG                                                                  6

SEQ ID NO: 25              moltype = AA   length = 5
FEATURE                    Location/Qualifiers
source                     1..5
                           mol_type = protein
                           organism = synthetic construct
SEQUENCE: 25
GWWWG                                                                   5
```

The invention claimed is:

1. A multimeric compound comprising two monomers covalently bound to one another via an intermolecular disulfide bond, each monomer comprising a bile acid-peptide conjugate, wherein the peptide comprised in the monomers comprises a nuclear localization signal (NLS), wherein the bile acid comprised in the monomers mediates endosomal escape of the multimeric compound.

2. The multimeric compound of claim 1, wherein the two monomers are covalently conjugated to one another via an intermolecular disulfide bond resulting from oxidation of thiol groups present in each monomer prior to multimerization.

3. The multimeric compound of claim 1, wherein the two monomers each comprise the same bile acid-peptide conjugate.

4. The multimeric compound of claim 1, wherein the bile acid is: cholic acid (CA), chenodeoxycholic acid (CDCA), deoxycholic acid (DCA), lithocholic acid (LCA), glycodeoxycholic acid (GDCA), glycocholic acid (GCA), taurocholic acid (TCA), glycochenodeoxycholic acid (GCDCA), taurodeoxycholic acid (TDCA), glycolithocholic acid (GLCA), taurolithocholic acid (TLCA), taurohyodeoxycholic acid (THDCA), taurochenodeoxycholic acid (TCDCA), ursocholic acid (UCA), tauroursodeoxycholic acid (TUDCA), ursodeoxycholic acid (UDCA), or glycoursodeoxycholic acid (GUDCA).

5. The multimeric compound of claim 1, wherein the bile acid is an analog of CA, CDCA, DCA, LCA, GDCA, GCA, TCA, GCDCA, TDCA, GLCA, TLCA, THDCA, TCDCA, UCA1, TUDCA, UDCA, or GUDCA, wherein the analog triggers ceramide accumulation on the inner leaflet of endosomes.

6. The multimeric compound of claim 1, wherein the bile acid is or comprises: CA or CDCA.

7. The multimeric compound of claim 1, wherein the NLS is a/an: SV40 NLS as set forth in SEQ ID NO: 1 or 2, GWG-SV40NLS comprising the sequence of SEQ ID NO: 3, hnRNPA1 M9 NLS as set forth in SEQ ID NO: 4, hnRNP D NLS as set forth in SEQ ID NO: 5, hnRNP M NLS as set forth in SEQ ID NO: 6, PQBP-1 NLS as set forth in SEQ ID NO: 7, NLS2-RG Domain RPS17 as set forth in SEQ ID NO: 8, NLS1 RPS17 as set forth in SEQ ID NO: 9, NLS2 RPS17 as set forth in SEQ ID NO: 10, NLS3 RPS17 as set forth in SEQ ID NO: 11, cMyc NLS as set forth in SEQ ID NO: 12, HuR NLS as set forth in SEQ ID NO: 13, Tus NLS as set forth in SEQ ID NO: 14, or Nucleoplasmin NLS as set forth in SEQ ID NO: 15.

8. The multimeric compound of claim 1, wherein the NLS is a/an hnRNPA1 M9 NLS as set forth in SEQ ID NO: 4, SV40 NLS as set forth in SEQ ID NO: 1 or 2} or hnRNP D NLS as set forth in SEQ ID NO: 5.

9. The multimeric compound of claim 1, wherein the multimeric compound is conjugated to a biocompatible carrier molecule.

10. The multimeric compound of claim 9, wherein the multimeric compound, or a monomer comprised therein, is releasably bound to the biocompatible carrier molecule via a cleavable linker.

11. The multimeric compound of claim 9, wherein the biocompatible carrier molecule is an antibody or receptor ligand.

12. The multimeric compound of claim 9, wherein the biocompatible carrier molecule is further bound to a cytotoxic agent or drug.

13. The multimeric compound of claim 1, wherein the bile acid comprises CA or CDCA, and the NLS is a/an hnRNPA1 M9 NLS as set forth in SEQ ID NO: 4, SV40 NLS as set forth in SEQ ID NO: 1 or 2 or hnRNP D NLS as set forth in SEQ ID NO: 5.

14. The multimeric compound of claim 1, further comprising an antigen admixed therewith or covalently conjugated thereto, wherein the admixture or covalent conjugation improves the immunogenicity of the antigen.

15. The multimeric compound of claim 13, further comprising an antigen admixed therewith or covalently conjugated thereto, wherein the admixture or covalent conjugation improves the immunogenicity of the antigen.

16. The multimeric compound of claim 1, which is comprised in a pharmaceutical composition at a cytotoxic or cytostatic concentration, free or bound to a biocompatible carrier molecule.

17. The multimeric compound of claim 13, which is comprised in a pharmaceutical composition at a cytotoxic or cytostatic concentration, free or bound to a biocompatible carrier molecule.

18. The multimeric compound of claim 1, wherein the bile acid comprises CDCA, and the NLS is an SV40 NLS as set forth in SEQ ID NO: 1 or 2.

19. The multimeric compound of claim 1, wherein the bile acid comprises CA, and the NLS is an hnRNPA1 M9 NLS as set forth in SEQ ID NO: 4.

* * * * *